US010772497B2

(12) United States Patent
Walsh et al.

(10) Patent No.: US 10,772,497 B2
(45) Date of Patent: Sep. 15, 2020

(54) MEDICAL INTERFACES AND OTHER MEDICAL DEVICES, SYSTEMS, AND METHODS FOR PERFORMING EYE EXAMS

(71) Applicant: Envision Diagnostics, Inc., El Segundo, CA (US)

(72) Inventors: Alexander C. Walsh, Los Angeles, CA (US); Paul G. Updike, Cerritos, CA (US); Richard Castro, Santa Monica, CA (US)

(73) Assignee: Envision Diagnostics, Inc., El Segundo, CA (US)

( * ) Notice: Subject to any disclaimer, the term of this patent is extended or adjusted under 35 U.S.C. 154(b) by 0 days.

(21) Appl. No.: 14/852,379

(22) Filed: Sep. 11, 2015

(65) Prior Publication Data
US 2017/0127932 A1 May 11, 2017

Related U.S. Application Data

(60) Provisional application No. 62/050,034, filed on Sep. 12, 2014, provisional application No. 62/050,676, (Continued)

(51) Int. Cl.
*A61B 3/00* (2006.01)
*A61B 3/10* (2006.01)
(Continued)

(52) U.S. Cl.
CPC ............ *A61B 3/0083* (2013.01); *A61B 3/102* (2013.01); *A61B 3/1225* (2013.01); *A61B 3/15* (2013.01);
(Continued)

(58) Field of Classification Search
CPC ......... A61B 3/102; A61B 3/14; A61B 3/1005; A61B 3/113; A61B 3/12; A61B 5/04842;
(Continued)

(56) References Cited

U.S. PATENT DOCUMENTS 3,538,754 A 11/1970 Grolman et al.
4,150,443 A 4/1979 McNeilly
(Continued)

FOREIGN PATENT DOCUMENTS

CA 2595324 7/2006
CA 2678506 8/2008
(Continued)

OTHER PUBLICATIONS

US 8,979,269 B2, 03/2015, Walsh et al. (withdrawn)
(Continued)

*Primary Examiner* — Thomas K Pham
*Assistant Examiner* — Alberto J Betancourt
(74) *Attorney, Agent, or Firm* — Knobbe, Martens, Olson & Bear, LLP

(57) ABSTRACT

A mask for performing an eye exam of a subject includes one or more optically transparent sections for transmitting an incident light beam therethrough and incident on the subject's eye. In some embodiments, the one or more optically transparent sections are coated with an anti-reflective coating configured to reduce reflection of the incident light beam by the one or more optically transparent sections. In some embodiments, the one or more optically transparent sections may have a portion thereof that is tilted with respect to the incident light beam when the mask is optically interfaced with the docking portion of an ophthalmic instrument, such that the incident light beam forms a finite angle of incidence with respect to the corresponding portion of the optically transparent sections.

19 Claims, 33 Drawing Sheets

Related U.S. Application Data filed on Sep. 15, 2014, provisional application No. 62/051,237, filed on Sep. 16, 2014.

(51) Int. Cl.
- *A61B 3/12* (2006.01)
- *A61B 5/00* (2006.01)
- *A61B 3/15* (2006.01)

(52) U.S. Cl.
CPC .......... *A61B 5/0066* (2013.01); *A61B 5/6803* (2013.01); *A61B 2562/247* (2013.01)

(58) Field of Classification Search
CPC ....... A61B 3/0083; A61B 5/6803; A61B 3/18; A61B 3/185; A61B 90/00; A61B 46/00–20; A61B 2046/201–205; A61B 46/23; A61B 46/27; A61B 46/30; A61B 46/40; A61B 50/00; A61B 5/0066; A61B 3/15; A61B 3/1225; A61B 2562/247; G01B 9/02091; A41D 13/11; A61F 2250/0003; A61F 9/026; A61F 9/04–06; G01L 39/02091
USPC ............ 351/206, 208, 200, 159.75; 356/511; 600/558, 300, 398, 452; 2/206, 6.3, 15, 2/431, 440, 442

See application file for complete search history.

(56) References Cited

U.S. PATENT DOCUMENTS

| | | | |
|---|---|---|---|
| 4,154,114 A | 5/1979 | Katz et al. | |
| 4,237,901 A | 12/1980 | Taenzer | |
| 4,393,366 A | 7/1983 | Hill | |
| 4,479,931 A | 10/1984 | Lambrecht et al. | |
| 4,740,072 A * | 4/1988 | Griffin | A61B 3/024 351/239 |
| 4,764,006 A | 8/1988 | Hamano et al. | |
| H574 H | 2/1989 | Merkel | |
| 4,848,340 A | 7/1989 | Bille et al. | |
| 4,872,217 A | 10/1989 | Kitayama | |
| 4,930,512 A | 6/1990 | Henriksen et al. | |
| 5,005,966 A | 4/1991 | Handler et al. | |
| 5,056,522 A | 10/1991 | Matsumura et al. | |
| 5,061,058 A * | 10/1991 | Guilino | G02B 9/00 351/159.52 |
| 5,129,109 A * | 7/1992 | Runckel | A63B 33/002 2/426 |
| 5,140,997 A * | 8/1992 | Glassman | A61B 46/00 128/849 |
| 5,141,302 A | 8/1992 | Arai et al. | |
| 5,214,455 A | 5/1993 | Penney et al. | |
| 5,345,946 A * | 9/1994 | Butterworth | A61B 46/00 128/853 |
| 5,369,454 A | 11/1994 | Reinstein et al. | |
| 5,442,412 A | 8/1995 | Frey et al. | |
| 5,467,104 A | 11/1995 | Furness, III et al. | |
| 5,491,524 A | 2/1996 | Hellmuth et al. | |
| 5,493,109 A | 2/1996 | Wei et al. | |
| 5,543,866 A | 8/1996 | Van de Velde | |
| 5,557,350 A | 9/1996 | Yano | |
| 5,644,642 A | 7/1997 | Kirschbaum | |
| 5,776,068 A | 7/1998 | Silverman et al. | |
| 5,838,424 A | 11/1998 | Wawro et al. | |
| 5,914,772 A | 6/1999 | Dyer | |
| 6,019,103 A * | 2/2000 | Carroll | A61F 9/026 128/858 |
| 6,086,205 A | 7/2000 | Svetliza | |
| 6,112,114 A | 8/2000 | Dreher | |
| 6,293,674 B1 | 9/2001 | Huang et al. | |
| 6,345,621 B1 * | 2/2002 | Chandler | A61B 46/00 128/849 |
| 6,367,932 B1 | 4/2002 | Donaldson | |
| 6,439,720 B1 | 8/2002 | Graves et al. | |
| 6,450,643 B1 | 9/2002 | Wilson | |
| 6,592,223 B1 | 7/2003 | Stern et al. | |
| 6,609,794 B2 | 8/2003 | Levine | |
| 6,619,799 B1 | 9/2003 | Blum et al. | |
| 6,634,237 B2 | 10/2003 | Neubert | |
| 6,656,131 B2 | 12/2003 | Alster et al. | |
| 6,687,389 B2 | 2/2004 | McCartney et al. | |
| 6,692,436 B1 | 2/2004 | Bluth et al. | |
| 6,705,726 B2 | 3/2004 | Tanassi et al. | |
| 6,820,979 B1 | 11/2004 | Stark et al. | |
| 6,939,298 B2 | 9/2005 | Brown et al. | |
| 7,008,116 B2 | 3/2006 | Kobayashi et al. | |
| 7,203,425 B1 | 4/2007 | Keller et al. | |
| 7,219,996 B2 | 5/2007 | Ichikawa | |
| 7,233,312 B2 | 6/2007 | Stern et al. | |
| 7,237,898 B1 | 7/2007 | Hohla et al. | |
| 7,347,548 B2 | 3/2008 | Huang et al. | |
| 7,350,921 B2 | 4/2008 | Ridings | |
| 7,370,966 B2 | 5/2008 | Fukuma et al. | |
| 7,384,146 B2 | 6/2008 | Covannon et al. | |
| 7,445,335 B2 | 11/2008 | Su et al. | |
| 7,458,685 B2 | 12/2008 | Liang et al. | |
| 7,549,752 B2 | 6/2009 | Peyman et al. | |
| 7,614,747 B2 | 11/2009 | Foster | |
| 7,618,372 B2 | 11/2009 | dela Houssaye | |
| 7,744,221 B2 | 6/2010 | Wei et al. | |
| 7,815,310 B2 | 10/2010 | Su et al. | |
| 7,884,945 B2 | 2/2011 | Srinivasan et al. | |
| 7,982,881 B2 | 7/2011 | Fercher et al. | |
| 7,997,728 B2 | 8/2011 | Huang et al. | |
| 8,002,410 B2 | 8/2011 | Shea | |
| 8,079,711 B2 | 12/2011 | Stetson et al. | |
| 8,100,530 B2 | 1/2012 | Zhou et al. | |
| 8,348,429 B2 | 1/2013 | Walsh et al. | |
| 8,372,411 B2 | 2/2013 | Meinke et al. | |
| 8,381,729 B2 | 2/2013 | Freitag et al. | |
| 8,820,931 B2 | 9/2014 | Walsh et al. | |
| 8,931,903 B2 | 1/2015 | Inoue | |
| 9,125,724 B2 | 9/2015 | Berdahl et al. | |
| 9,149,182 B2 | 10/2015 | Walsh et al. | |
| 9,226,856 B2 | 1/2016 | Walsh et al. | |
| 9,492,079 B2 | 11/2016 | Walsh et al. | |
| 9,848,773 B2 | 12/2017 | Wei | |
| 10,165,941 B2 | 1/2019 | Walsh et al. | |
| 2001/0025226 A1 | 9/2001 | Lavery | |
| 2001/0033410 A1 | 10/2001 | Helsel et al. | |
| 2002/0021411 A1 | 2/2002 | Wilson | |
| 2002/0052551 A1 | 5/2002 | Sinclair et al. | |
| 2002/0080329 A1 | 6/2002 | Kasahara | |
| 2002/0099305 A1 | 7/2002 | Fukushima et al. | |
| 2002/0159030 A1 * | 10/2002 | Frey | A61B 3/1015 351/212 |
| 2003/0065636 A1 | 4/2003 | Peyrelevade | |
| 2003/0090172 A1 | 5/2003 | Lee et al. | |
| 2003/0232015 A1 | 12/2003 | Brown et al. | |
| 2004/0019032 A1 | 1/2004 | North et al. | |
| 2004/0036838 A1 | 2/2004 | Podoleanu et al. | |
| 2004/0141152 A1 | 7/2004 | Marino et al. | |
| 2004/0196432 A1 | 10/2004 | Su et al. | |
| 2004/0254154 A1 | 12/2004 | Ashton | |
| 2004/0260183 A1 | 12/2004 | Lambert et al. | |
| 2005/0001980 A1 | 1/2005 | Spector | |
| 2005/0018133 A1 | 1/2005 | Huang et al. | |
| 2005/0041200 A1 | 2/2005 | Rich | |
| 2005/0105044 A1 | 5/2005 | Warden et al. | |
| 2005/0128735 A1 | 6/2005 | Atkins et al. | |
| 2005/0140981 A1 | 6/2005 | Waelti | |
| 2006/0062442 A1 | 3/2006 | Arnaud | |
| 2006/0077347 A1 | 4/2006 | Liang et al. | |
| 2006/0077348 A1 | 4/2006 | Gorin | |
| 2006/0092376 A1 | 5/2006 | Baek et al. | |
| 2006/0109423 A1 | 5/2006 | Wang | |
| 2006/0119858 A1 | 6/2006 | Knighton et al. | |
| 2006/0135859 A1 | 6/2006 | Iliff | |
| 2006/0158655 A1 | 7/2006 | Everett et al. | |
| 2006/0187462 A1 | 8/2006 | Srinivasan et al. | |
| 2006/0195076 A1 | 8/2006 | Blumenkranz et al. | |
| 2006/0203195 A1 | 9/2006 | Squire et al. | |

(56) References Cited

U.S. PATENT DOCUMENTS

| | | |
|---|---|---|
| 2006/0257451 A1 | 11/2006 | Varner et al. |
| 2006/0284813 A1 | 12/2006 | Yamamoto et al. |
| 2006/0290885 A1 | 12/2006 | Covannon et al. |
| 2007/0008116 A1 | 1/2007 | Bergman et al. |
| 2007/0024868 A1 | 2/2007 | Izatt et al. |
| 2007/0030450 A1 | 2/2007 | Liang et al. |
| 2007/0032782 A1 | 2/2007 | Youssefi et al. |
| 2007/0055222 A1 | 3/2007 | Hohla et al. |
| 2007/0073113 A1 | 3/2007 | Squilla et al. |
| 2007/0081165 A1 | 4/2007 | Kilic et al. |
| 2007/0081166 A1 | 4/2007 | Brown et al. |
| 2007/0153233 A1 | 7/2007 | Campin et al. |
| 2007/0159597 A1 | 7/2007 | Fukuma et al. |
| 2007/0177104 A1 | 8/2007 | Lacombe et al. |
| 2007/0195269 A1 | 8/2007 | Wei et al. |
| 2007/0216909 A1 | 9/2007 | Everett et al. |
| 2007/0263171 A1 | 11/2007 | Ferguson et al. |
| 2007/0273831 A1 | 11/2007 | Liang et al. |
| 2007/0282313 A1 | 12/2007 | Huang et al. |
| 2007/0287932 A1 | 12/2007 | Huang et al. |
| 2007/0291228 A1 | 12/2007 | Huang et al. |
| 2007/0291277 A1 | 12/2007 | Everett et al. |
| 2008/0007694 A1 | 1/2008 | Wei et al. |
| 2008/0049186 A1 | 2/2008 | MacDougal et al. |
| 2008/0106696 A1 | 5/2008 | Buckland et al. |
| 2009/0141240 A1 | 6/2009 | Weitz et al. |
| 2009/0153796 A1 | 6/2009 | Rabner |
| 2009/0180074 A1 | 7/2009 | Benyamini et al. |
| 2009/0180169 A1 | 7/2009 | Moidu et al. |
| 2010/0033678 A1 | 2/2010 | Foster |
| 2010/0100238 A1 | 4/2010 | Torian |
| 2010/0110377 A1 | 5/2010 | Maloca et al. |
| 2010/0277668 A1* | 11/2010 | Frank ............ B32B 3/30 349/62 |
| 2010/0280315 A1 | 11/2010 | Pan |
| 2011/0047682 A1 | 3/2011 | Hedayat |
| 2011/0099718 A1 | 5/2011 | iEilers et al. |
| 2012/0075584 A1 | 3/2012 | Stetson |
| 2012/0133888 A1* | 5/2012 | Gray ............ A61B 3/1025 351/206 |
| 2012/0184845 A1 | 7/2012 | Ishikawa et al. |
| 2012/0222185 A1* | 9/2012 | Erikson ............ A61F 9/04 2/11 |
| 2012/0257166 A1 | 10/2012 | Francis et al. |
| 2012/0274897 A1 | 11/2012 | Narasimha-Iyer et al. |
| 2013/0010259 A1 | 1/2013 | Carnevale |
| 2013/0194545 A1* | 8/2013 | Ono ............ A61B 3/0091 351/206 |
| 2013/0265537 A1* | 10/2013 | Bottieri ............ G02C 1/10 351/90 |
| 2013/0300653 A1 | 11/2013 | Lewis et al. |
| 2013/0308099 A1 | 11/2013 | Stack |
| 2014/0009741 A1 | 1/2014 | Levien et al. |
| 2014/0046193 A1* | 2/2014 | Stack ............ A61B 3/113 600/476 |
| 2014/0185012 A1* | 7/2014 | Kanazawa ............ A61B 3/18 351/237 |
| 2015/0138503 A1 | 5/2015 | Walsh et al. |
| 2015/0204650 A1 | 7/2015 | Erlich |
| 2016/0213250 A1 | 7/2016 | Wei |
| 2016/0270656 A1 | 9/2016 | Samec et al. |
| 2016/0278630 A1 | 9/2016 | Walsh et al. |
| 2017/0049318 A1 | 2/2017 | Walsh et al. |
| 2017/0119247 A1 | 5/2017 | Walsh et al. |
| 2017/0206657 A1 | 7/2017 | Nozato et al. |
| 2017/0215723 A1 | 8/2017 | Sakurada et al. |
| 2017/0311796 A1 | 11/2017 | Walsh et al. |
| 2017/0332899 A1 | 11/2017 | Walsh et al. |
| 2018/0084994 A1 | 3/2018 | Wei |
| 2018/0279870 A1 | 10/2018 | Walsh |
| 2019/0090733 A1 | 3/2019 | Walsh et al. |

FOREIGN PATENT DOCUMENTS

| | | |
|---|---|---|
| CN | 1593329 A | 3/2005 |
| CN | 200 980 154 Y | 11/2007 |
| CN | 201 491 234 U | 5/2010 |
| DE | 10 2005 05822 | 6/2007 |
| EP | 0 697 611 | 2/1996 |
| EP | 1 775 545 | 4/2007 |
| EP | 1 858 402 | 11/2007 |
| EP | 1 864 608 | 12/2007 |
| EP | 2 124 713 | 12/2009 |
| EP | 2 796 088 | 10/2014 |
| EP | 2 967 320 | 1/2016 |
| FR | 2 690 329 | 10/1993 |
| IL | 242605 | 11/2015 |
| JP | S 57-29204 | 6/1982 |
| JP | 05-220113 | 8/1993 |
| JP | 11-225958 | 8/1999 |
| JP | 2005-803954 | 3/2005 |
| JP | 2012-161595 | 8/2012 |
| WO | WO 1995/18563 | 7/1995 |
| WO | WO 1998/22016 | 5/1998 |
| WO | WO 1999/57507 | 11/1999 |
| WO | WO 2002/088684 | 11/2002 |
| WO | WO 2004/002298 | 1/2004 |
| WO | WO 2005/079655 | 9/2005 |
| WO | WO 2006/078802 | 7/2006 |
| WO | WO 2007/065493 | 6/2007 |
| WO | WO 2007/139927 | 12/2007 |
| WO | WO 2007/142960 | 12/2007 |
| WO | WO 2008/101359 | 8/2008 |
| WO | WO 2009/095473 | 8/2009 |
| WO | WO 2009/128912 | 10/2009 |
| WO | WO 2009/131701 | 10/2009 |
| WO | WO 2003/073922 | 9/2013 |
| WO | WO 2014/074590 | 5/2014 |
| WO | WO 2014/158658 | 10/2014 |
| WO | WO 2014/191031 | 12/2014 |
| WO | WO 2017/048873 | 3/2017 |
| WO | WO 2017/190071 | 11/2017 |
| WO | WO 2017/190097 | 11/2017 |

OTHER PUBLICATIONS

US 10,357,153 B2, 07/2019, Walsh et al. (withdrawn)
"3D OCT-1000 | Topcon," Press Release Mar. 31, 2008, available from internet at http://www.topcon.co.jp/news/20080331-508.html, site visited Apr. 14, 2015.
"A New Level for Retinal Imaging: Topcon's 3D OCT-1000," Vision Care Product New Nov./Dec. 2007 pp. 1-2.
"American National Standard Occupational and Educational Personal Eye and Face Protection Devices," available from internet at https://law.resource.org/pub/us/cfr/ibr/002/ansi.z87.1.2003.html, apparently available Jun. 2003, site visited Nov. 23, 2015.
"Topcon Medical Systems Releases 3D OCT-1000 TrueMapTM Software Version 2.12," Topcon Press Release Feb. 8, 2008, pp. 1-2.
Bachmann, et al., Heterodyne Fourier domain optical coherence tomography for full range probing with high axial resolution; Optics Express; vol. 14; Issue No. 4; pp. 1487-1496, Feb. 20, 2006.
Bigelow, et al., Compact multimodal adaptive-optics spectral-domain optical coherence tomography instrument for retinal imaging; J.Opt. Soc., Am. A.; vol. 24; Issue No. 5; pp. 1327-1336, May 2007.
Bowd, C., et al., "Bayesian Machine Learning Classifiers for Combining Structural and Functional Measurements to Classify Healthy and Glaucomatous Eyes," Investigative Ophthalmology & Visual Science, Mar. 2008, 49(3): 945-953.
Boyer, K.L., et al. "Automatic Recovery of the Optic Nervehead Geometry in Optical Coherence Tomography," IEEE Transactions on Medical Imaging, May 2006, 25(5): 553-570.
Brochure for Optical Coherence Tomography 3D OCT-1000 Mark II, in 12 pages.
Brochure for Optical Coherence Tomography 3D OCT-1000 Mark II, in 11 pages. Copyright 2008.

(56) References Cited

OTHER PUBLICATIONS

Bu, et al., Full-range parallel Fourier-domain optical coherence tomography using sinusoidal phase-modulating interferometry; Journal of Optics A: Pure and Applied Optics; vol. 9; pp. 422-426, Mar. 2007.
Burgansky-Eliash, et al., Optical Coherence Tomography Machine Learning Classifiers for Glaucoma Detection: A Preliminary Study, Investigative Ophthalmology & Visual Science; vol. 46; No. 11; pp. 4147-4152, Nov. 2005.
Chang, et al.; New developments in optical coherence tomography for glaucoma, Current Opinion in Ophthalmology; vol. 19; Issue No. 2; pp. 127-135; Mar. 2008.
Drexler, et al., State-of-the-art retinal optical coherence tomography; Progress in Retinal and Eye Research; vol. 27; Issue 1; pp. 45-88; Jan. 2008.
Fernandez, Delineating Fluid-Filled Region Boundaries in Optical Coherence Tomography Images of the Retina; IEEE Transactions on Medical Imaging; vol. 24; Issue No. 8; pp. 929-945, Aug. 2005.
Ghosn, et al., Nondestructive Quantification of Analyte Diffusion in Cornea and Sclera Using Optical Coherence Tomography; investigative Ophthalmology & Visual Science; vol. 48, No. 6, pp. 2726-2733, Jun. 2007.
Guo et al., "En face optical coherence tomography" a new method to analyse structural changes of the optic nerve head in rat glaucoma, British Journal of Ophthalmology, Sep. 2005, vol. 89, Issue 9, pp. 1210-1216.
Huang, et al., Development and Comparison of Automated Classifiers for Glaucoma Diagnosis Using Stratus Optical Coherence Tomography; Investigative Ophthalmology & Visual Science; vol. 46; Issue No. 11; pp. 4121-4129, Nov. 2005.
Joeres, et al.: "Reproducibility of Quantitative Optical Coherence Tomography Subanalysis in Neovascular Age-Related Macular Degeneration," IOVS, Sep. 2007, vol. 48., No. 9.
Keystone View; Computer Controlled vision Screeners. http://www.keystoneview.com?p=cv&id=39, 2 pages, 2003.
Koizumi et al: "Three-Dimensional Evaluation of Vitreomacular Traction and Epiretinal Membrane Using Spectral-Domain Optical Coherence Tomography" American Journal of Ophthalmology, Ophthalmic Publ, Chicago, IL, US, vol. 145, No. 3, Jan. 11, 2008, pp. 509-517.e1.
Koozekanani, et al., Retinal Thickness Measurements from Optical Coherence Tomography Using a Markov Boundary Model. IEEE Transactions on Medical Imaging; vol. 20; No. 9; pp. 900-916, Sep. 2001.
Lavanya, et al, Screening for Narrow Angles in the Singapore Population: Evaluation of New Noncontact Screening Methods; vol. 115; Issue No. 10, pp. 1720-1727e2, Oct. 2008.
Manassakorn, et al., Comparison of Retinal Nerve Fiber Layer Thickness and Optic Disk Algorithms with Optical Coherence Tomography to Detect Glaucoma; Am J Ophthalmol; vol. No. 141; pp. 105-115; Jan. 2006.
Parikh, M.D., et al., Diagnostic Capability of Optical Coherence Tomography (Stratus OCT 3) in Early Glaucoma; American Academy of Ophthalmology; vol. 114, Issue No. 12; pp. 2238-2243, Dec. 2007.
Prevent Blindness America. SureSight Vision Screener. Prevent Blindness Tri-State. http://www.preventblindness.org/tristate/suresight.html, 2 pages, 2006.
Sadda, Srinivas R., et al., Automated Detection of Clinically Significant Macular Edema by Grid Scanning Optical Coherence Tomography. American Academy of Ophthalmology, vol. 113, No. 7, pp. 1187 e.1-1187 e.12, Jul. 2006.
Sandhu, et al.: "Correlation of optical coherence tomography, with or without additional colour fundus photography, with stereo fundus fluorescein angiography in diagnosing choroidal neovascular membranes," downloaded from gttp://bjo.bmj.com/ on Nov. 27, 2016. Br J Ophthalmol 2005; 89:967-970.
Sarunic et al., "New Imaging Device Can Detect Glaucoma Risk", Duke Medicine News and Communications, Jun. 2008.

Shields, et al.: "Photoreceptor Loss Overlying Congenital Hypertrophy of the Retinal Pigment Epithelium by Optical Coherence Tomography," Ophthalmology vol. 113, No. 4, Apr. 2006.
Stein, et al., A new quality assessment parameter for optical coherence tomography; British Journal of Ophthalmology; vol. 90, Issue No. 2; pp. 186-190; Feb. 2006.
Stereo Optical Co., Inc. The Optec® 5500/5500 P-Industry Standard for Visual Screening and Vision Testing Devices. http://www.stereooptical.com/html/optec-5500.html, 3 pages, 2007.
Stereo Optical Co., Inc. The Optec® Functional Vision Analyzer$^{TM}$ Contrast Sensitivity Tests with Two Glare Levels Under Four Testing Conditions. http://www.stereooptical.com/html/functional_vision_analyzer.html, 3 pages, 2007.
Stratus OCT$^{TM}$ Software version 4.0 Real Answers in Real Time. [Online] Jan. 2006, XP002530105 Retrieved from the Internet: URL: http://www.meditec.zeiss.com/88256DE3007B916B/0/C26634DOCFF04511882571Bl005DECFD/$file/stratusocLen.pdf>[retrieved on May 28, 2009] the whole document.
Topcon Medical Systems Receives FDA Clearance to Market the 3D OCT-1000, the World's First Combination of Fourier Domain OCT and a Color Non-Mydriatic Retinal Camera, Topcon Press Release Jul. 2, 2007, pp. 1-2.
Topcon Optical Coherence Tomography 3D OCT-1000 Brochure, 7 pages, 2008.
Vakhtin, et al, Common-path interferometer for frequency-domain optical coherence tomography; Applied Optics; vol. 42, Issue No. 34; pp. 6953-6958, 2003.
Vakhtin, et al., Demonstration of complex-conjugate-resolved harmonic Fourier-domain optical coherence tomography imaging of biological samples; Applied Optics; vol. 46; Issue No. 18; pp. 3870-3877, Jun. 20, 2007.
Van de Moere, et al.: "Correlation of optical coherence tomography and fundus fluorescein angiography following photodynamic therapy for choroidal neovascular membranes," downloaded from http://bjo.bmj.com/ on Nov. 27, 2016. Br J. Ophthalmol 2006; 90:304-306.
Walsh, A. "3D-OCT in the Evaluation of Retinal Disease," Highlights of Ophthalmology, Jul. 2006, 34(3): 9-10.
Walsh, A. M.D., "Next-generation OCT: What to Look for in a Fourier Domain OCT Instrument," Retinal Physician, pp. 1-6, May 1, 2007.
Xu, et al., Anterior Chamber Depth and Chamber Angle and Their Associations with Ocular and General Parameters: The Beijing Eye Study. American Journal of Ophthalmology, vol. 145, pp. 929-936.e1, May 2008.
Yasuno, et al., One-shot-phase-shifting Fourier domain optical coherence tomography by reference wavefront tilting; Optics Express; vol. 12; Issue No. 25; pp. 6184-6191, Dec. 13, 2004.
Zhang, et al., Full range polarization-sensitive Fourier domain optical coherence tomography; Optics Express; vol. 12; Issue No. 24; pp. 6033-6039, Nov. 29, 2004.
Zhang, et al.: "Optical Coherence Tomography Reader Agreement in Neovascular Age-related Macular Degeneration," American Journal of Ophthalmology, vol. 144, No. 1, Jul. 2007, pp. 37-44.e1.
Zhou et al., "Biometric measurement of the mouse eye using optical coherence tomography with focal plane advancement", Vision Research, Apr. 2008, vol. 48, pp. 1137-1143.
Office Action dated Apr. 24, 2015 in U.S. Appl. No. 13/802,727.
Preliminary Amendment of U.S. Appl. No. 13/802,727, dated Jun. 24, 2013.
Amendment in U.S. Appl. No. 13/802,727 dated Jul. 24, 2015.
Notice of Allowance in U.S. Appl. No. 13/802,727 dated Aug. 24, 2015.
Preliminary Amendment in U.S. Appl. No. 14/984,035 dated Jun. 15, 2016.
International Search Report and Written Opinion, re PCT/US2014/019150, dated Dec. 4, 2014.
International Report on Patentability and Written Opinion, re PCT/US2014/019150, dated Sep. 15, 2015.
International Search Report and Written Opinion, re PCT/US2016/051778, dated Jan. 5, 2017.
International Search Report and Written Opinion, re PCT/US2017/030263, dated Jul. 11, 2017.

(56) References Cited

OTHER PUBLICATIONS

International Preliminary Report on Patentability, re PCT/US2016/051778, dated Mar. 20, 2018.
Hoffman, et al., "Resonant bixial 7-mm MEMS mirror for omnidiretiona scanning," SPIE MOEMS-MEMS, 2013, San Francisco CA. Mar. 13, 2013. Abstract.
Katayev, MD, et al., "Establishing Reference Intervals for Clinical Laboratory Test Results," Am J Clin Pathol 2010; 133:180-186.
Katayev, MD, et al., "Reference Intervals Data Mining," Am J Clin Pathol Jan. 2015;143:134-142.
Sandner, et al., "Quasi-static Microscanner with Linearized Scanning for an adaptive 3D-Lascercamer," AMA Conferences 2013—Sensor 2013, OPTO 2013, IRS 2 2013.
Sandner, et al., "Application specific Micro Scanning Mirror," Sensor+Test Conferences 2011 Sensor Proceedings.

* cited by examiner

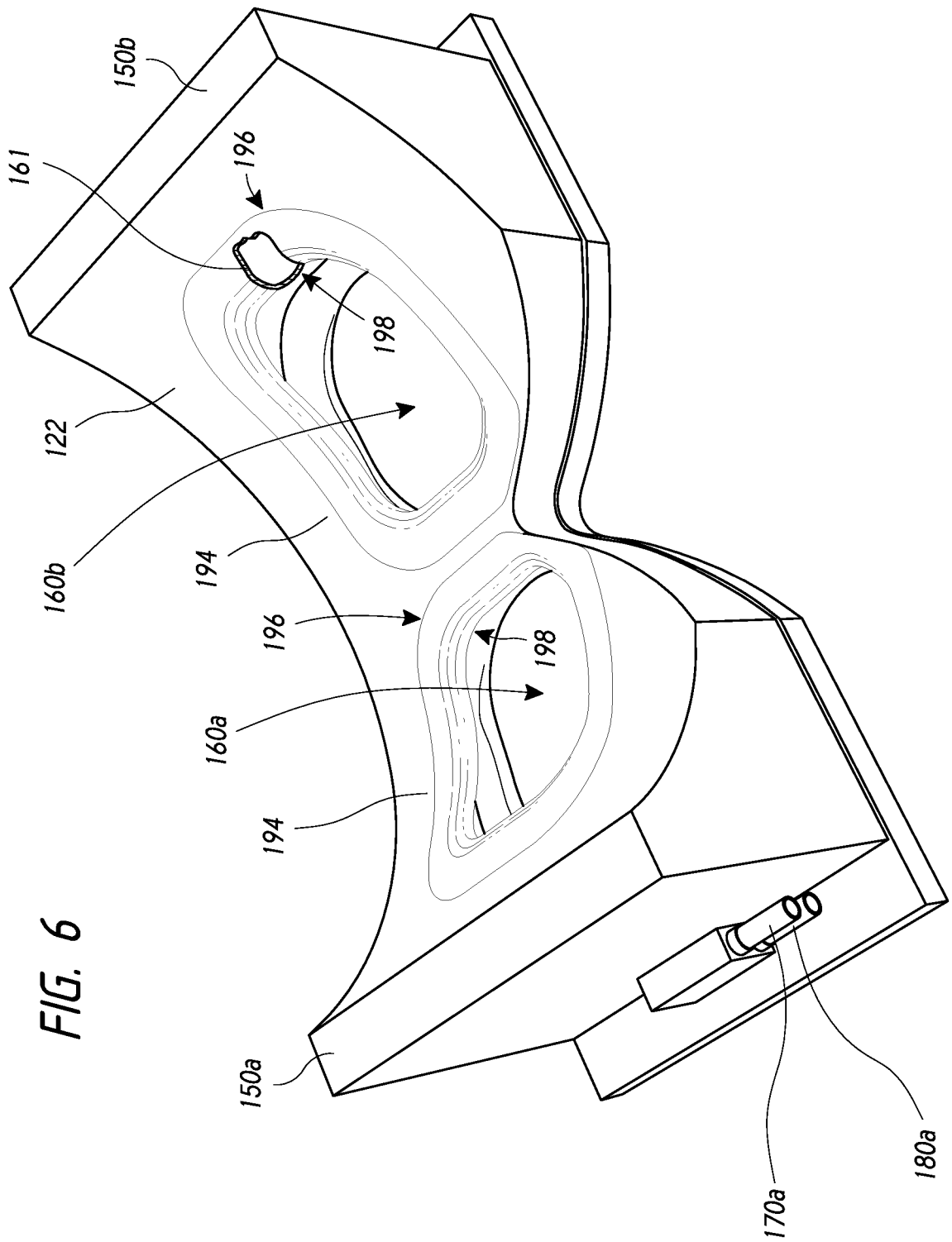

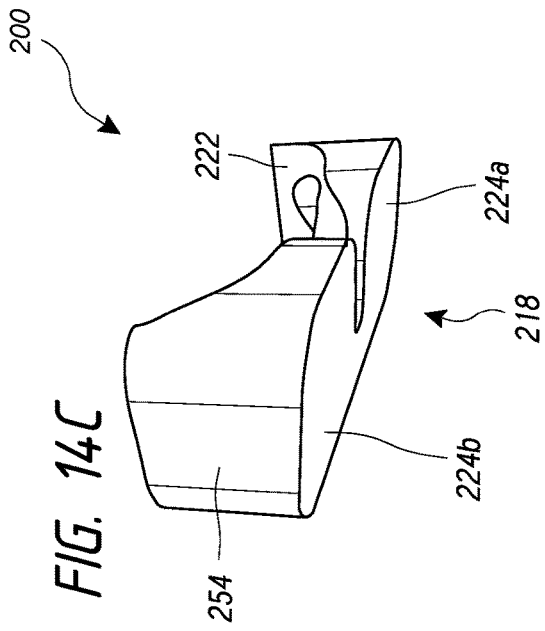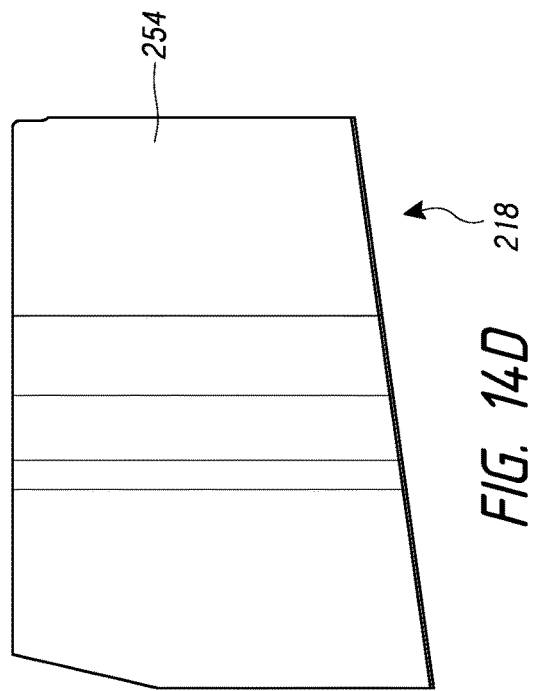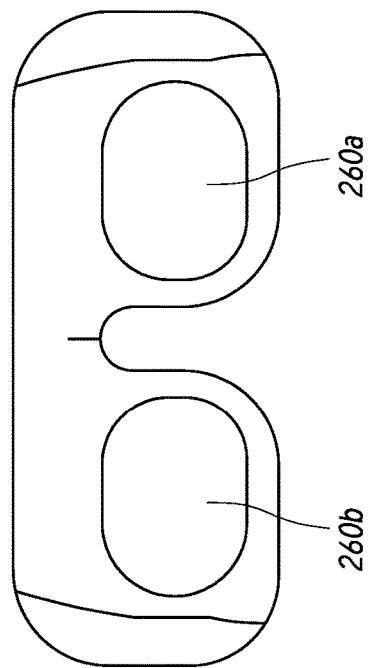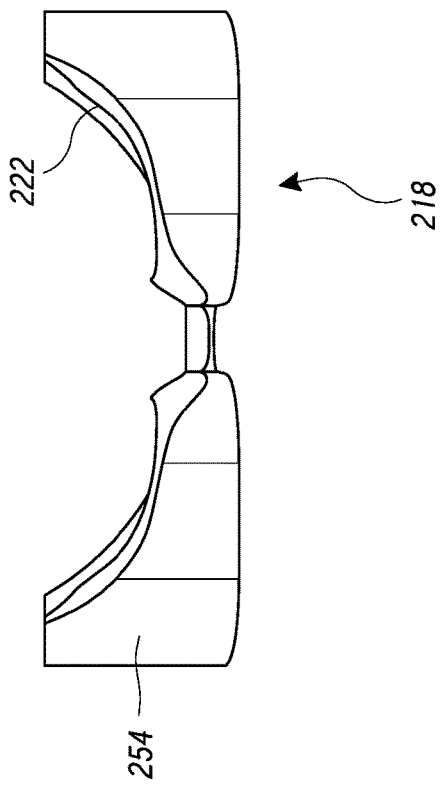

Offset angle Δ reduces back-reflection into beam steering mirror

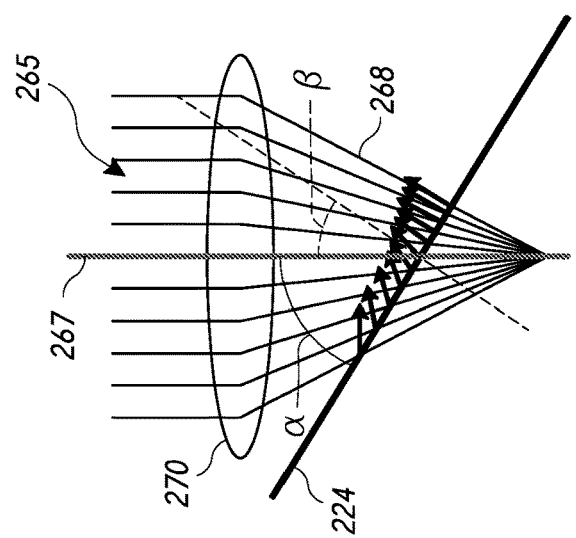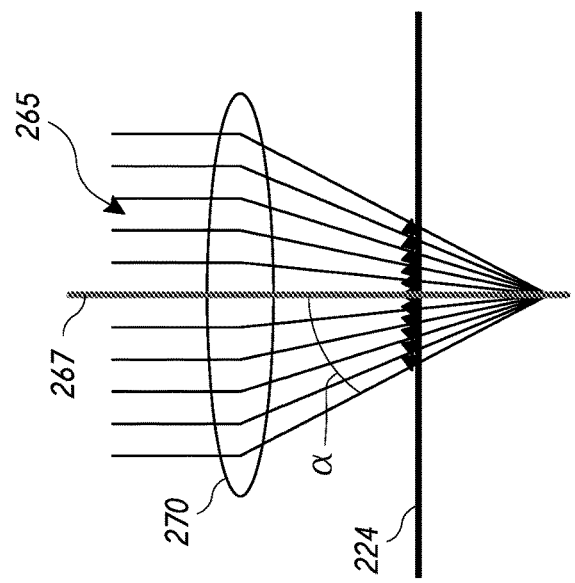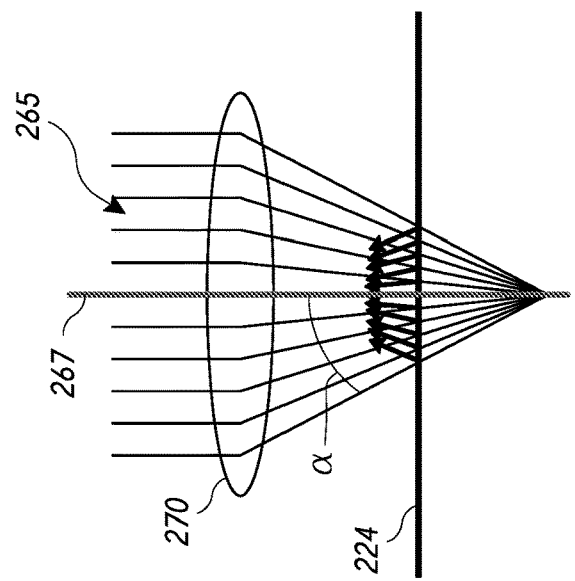

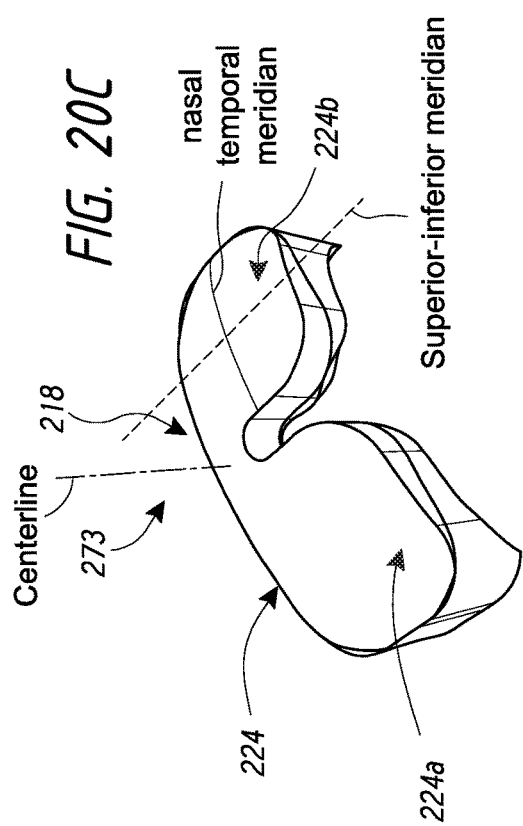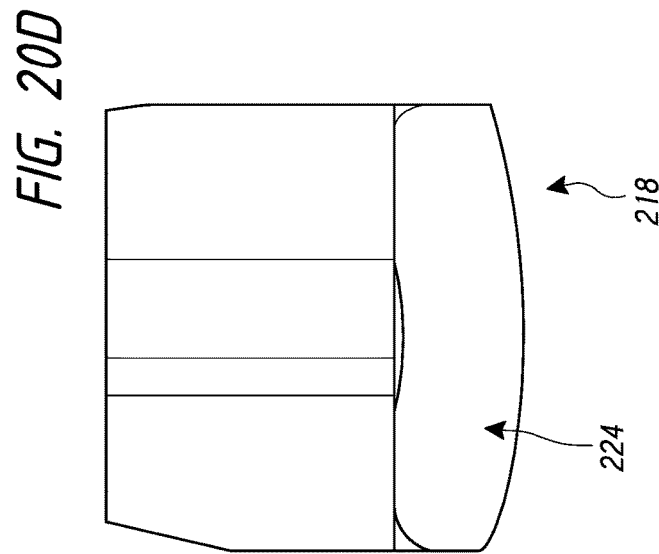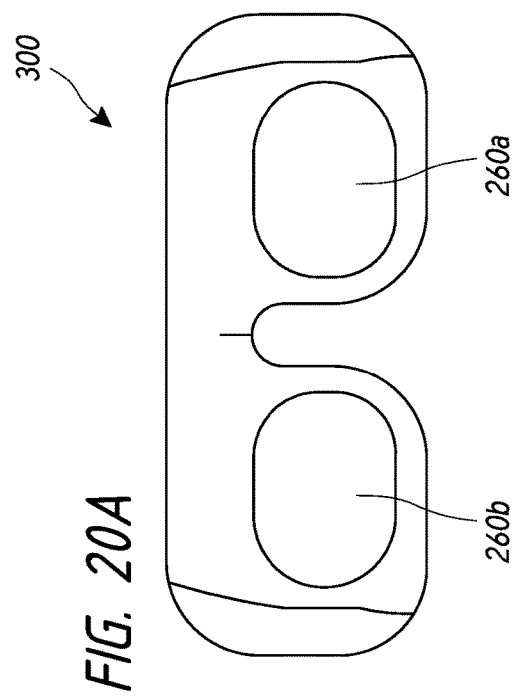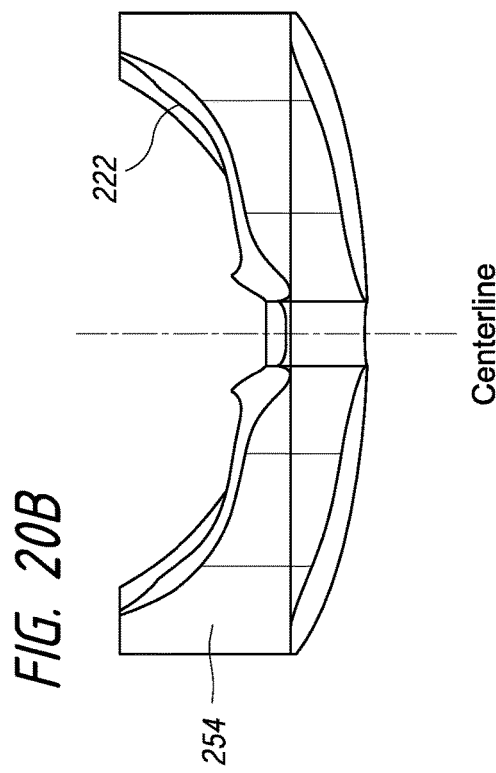

FIG. 28A
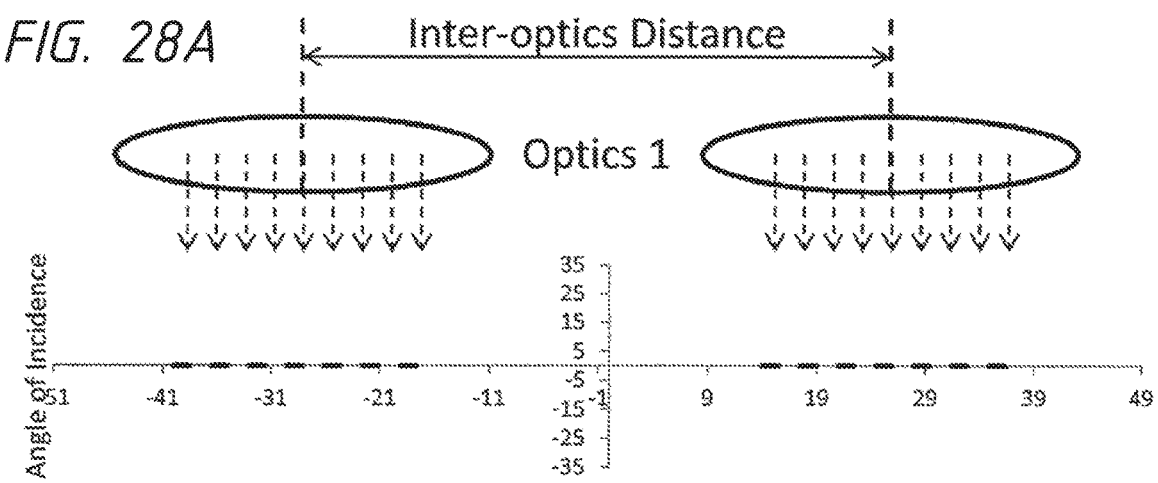
FIG. 28B
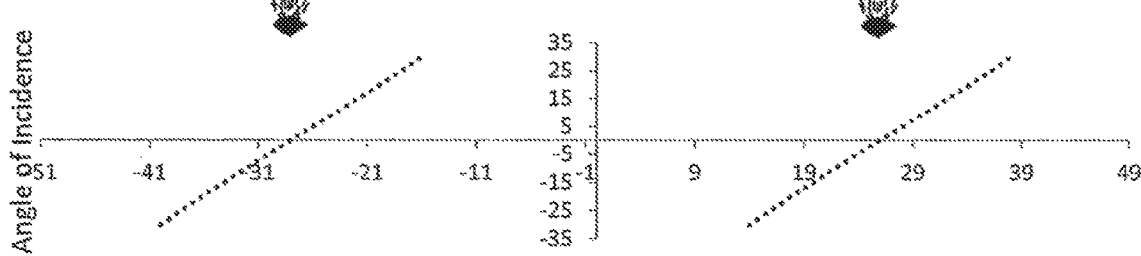
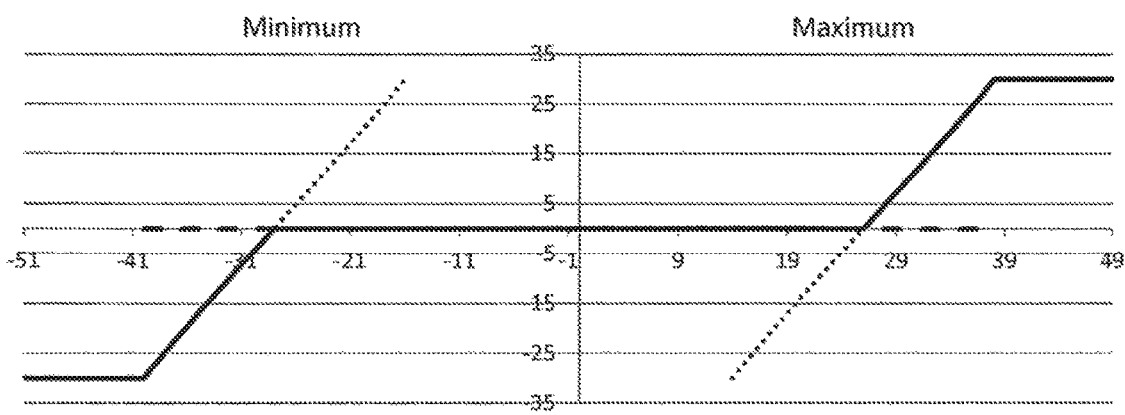
FIG. 28C

MEDICAL INTERFACES AND OTHER MEDICAL DEVICES, SYSTEMS, AND METHODS FOR PERFORMING EYE EXAMS

RELATED APPLICATIONS

This application claims priority benefit under 37 C.F.R. 119(e) to U.S. Provisional Patent Application No. 62/051,237, filed Sep. 16, 2014, U.S. Provisional Patent Application No. 62/050,034, filed Sep. 12, 2014, as well as U.S. Provisional Patent Application No. 62/050,676, filed Sep. 15, 2014. Each of these above-referenced applications are incorporated herein by reference in their entirety.

BACKGROUND

Field

Embodiments of the present disclosure relate to the field of healthcare, including for example, devices, systems, methods of automating the provision of diagnostic healthcare services to a patient as part of an examination meant to detect disorders or diseases. In some but not all instances, these healthcare services may apply only to eye care encounters, exams, services and eye diseases.

Description of the Related Art

Many people visiting medical offices often use the same equipment. Cross-contamination has become a problem of increasing concern, especially during certain periods such as flu season. As the provision of healthcare becomes more automated, fewer office personnel may be present to clean devices between uses. Accordingly systems and methods for improving hygiene are desirable.

SUMMARY

A wide range of embodiments are described herein. In some embodiments, a mask may comprise a distal sheet member having one or more substantially optically transparent sections and a proximal inflatable member having a rear concaved surface that may face a first patient's face when in use. The rear concaved surface may be configured to conform to contours of the first patient's face. The inflatable member may have two cavities therein. The two cavities may be generally aligned with the one or more substantially optically transparent sections, and may extend from the rear concaved surface toward the distal sheet member such that the cavities define two openings on the rear concave surface. The rear concave surface may be configured to seal against the first patient's face such that the first patient's eyes align with the two cavities, so that the rear concave surface forms seals around a peripheral region of the first patient's eye sockets that inhibit flow of fluid into and out of the cavities. The mask may further comprise an ocular port providing access to at least one of the two ocular cavities for fluid flow into and out of the at least one of the two ocular cavities and an inflation port providing access to inflate the inflatable member.

In various embodiments, the rear concaved surface may be configured to conform to the contours of the first patient's face with inflation of the inflatable member via the inflation port. The inflatable member may be underinflated and the rear concaved surface may be configured to conform to the contours of the first patient's face with inflation of the underinflated inflatable member via the inflation port. The rear concaved surface may be configured to conform to the contours of the first patient's face with application of negative pressure to the inflatable member via the inflation port. The mask may further comprise particulate matter disposed within the inflatable member. The particulate matter may be configured to pack together with application of a negative pressure to the inflatable member via the inflation port, so that the rear concaved surface conforms to the contours of the first patient's face.

In various embodiments, the rear concaved surface may be configured to conform to contours of a second patient's face, wherein a contour of the second patient's face is different from a contour of the first patient's face. The seals may be air-tight. The mask may further comprise a lip extending into at least one of the two cavities from a perimeter of at least one of the two openings, the lip having distal ends curving toward the distal sheet member in a default position, the distal ends configured to move rearwardly such that the lip seals against the user's face upon introduction of positive pressure into the at least one of the two cavities. The inflatable member may be opaque.

In various embodiments, the distal sheet may be configured to interface with a medical device, which may be an eye exam device. The mask may be configured to couple with a docking portion on a medical device. The mask may be configured to couple with the docking portion via a flange that slides into a slot of the docking portion. The inflation port and the ocular port of the mask may be configured to couple with conduit ends on a medical device. The ocular port and the inflation port may include a male portion, wherein the conduit ends on the medical device include a female portion configured to slidably receive the male portion. The ocular port and the inflation port may be configured to couple with the conduit ends on the medical device substantially simultaneously.

Some embodiments relate to the utilization of devices that replace, augment or enhance human laborers in a clinical health care setting. These devices may be used alone or in conjunction with other devices used in exams such as exams of the eye.

For purposes of this summary, certain aspects, advantages, and novel features of the invention are described herein. It is to be understood that not necessarily all such aspects, advantages, and features may be employed and/or achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which:

FIG. 6 schematically illustrates a perspective view of another embodiment of a mask with a seal around the ocular cavities.

FIGS. 14A-D schematically illustrate a mask having optically transparent sections that are tilted or sloped upward or downward and include an anti-reflection (AR) coating to reduce retro-reflection of light from an incident probe beam from an optical coherence tomography instrument back into the instrument.

FIGS. 15C-E schematically illustrate the effect of a tilted or sloped window on a mask on the light reflected from an incident OCT probe beam and how tilting or sloping the window beyond the angle of the steepest ray of light from the probe beam can reduce retro-reflection into the optical coherence tomography instrument.

FIGS. 20A-D schematically illustrate a mask having an optical window having wrap as well as curvature in the superior-inferior meridian to reduce retro-reflection of light from the optical coherence tomography instrument back into the OCT instrument.

FIGS. 28A-D schematically illustrate design considerations in determining the slope of the window at different distances from the centerline through the mask.

DETAILED DESCRIPTION OF THE PREFERRED EMBODIMENT

Some embodiments disclosed herein provide an inflatable mask that can interface with medical devices, such as medical diagnostic devices, such as optical coherence tomography ("OCT") devices. The inflatable mask can serve a variety of purposes, including maintaining a barrier between the patient and the medical device to ensure cleanliness and hygiene, providing comfort to the patient, and stabilizing the patient's location with respect to the machine. In some embodiments, the inflatable mask can form air-tight ocular cavities around the patient's eyes, allowing for pressurization of the ocular cavities, in order to obtain ocular measurements. Additionally, various embodiments of an automatic portal system and an automated eye examination are disclosed herein.

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may comprise several novel features, no single one of which is solely responsible for its desirable attributes or which is essential to practicing the embodiments of the inventions herein described.

Inflatable Medical Interface

Figure 1:
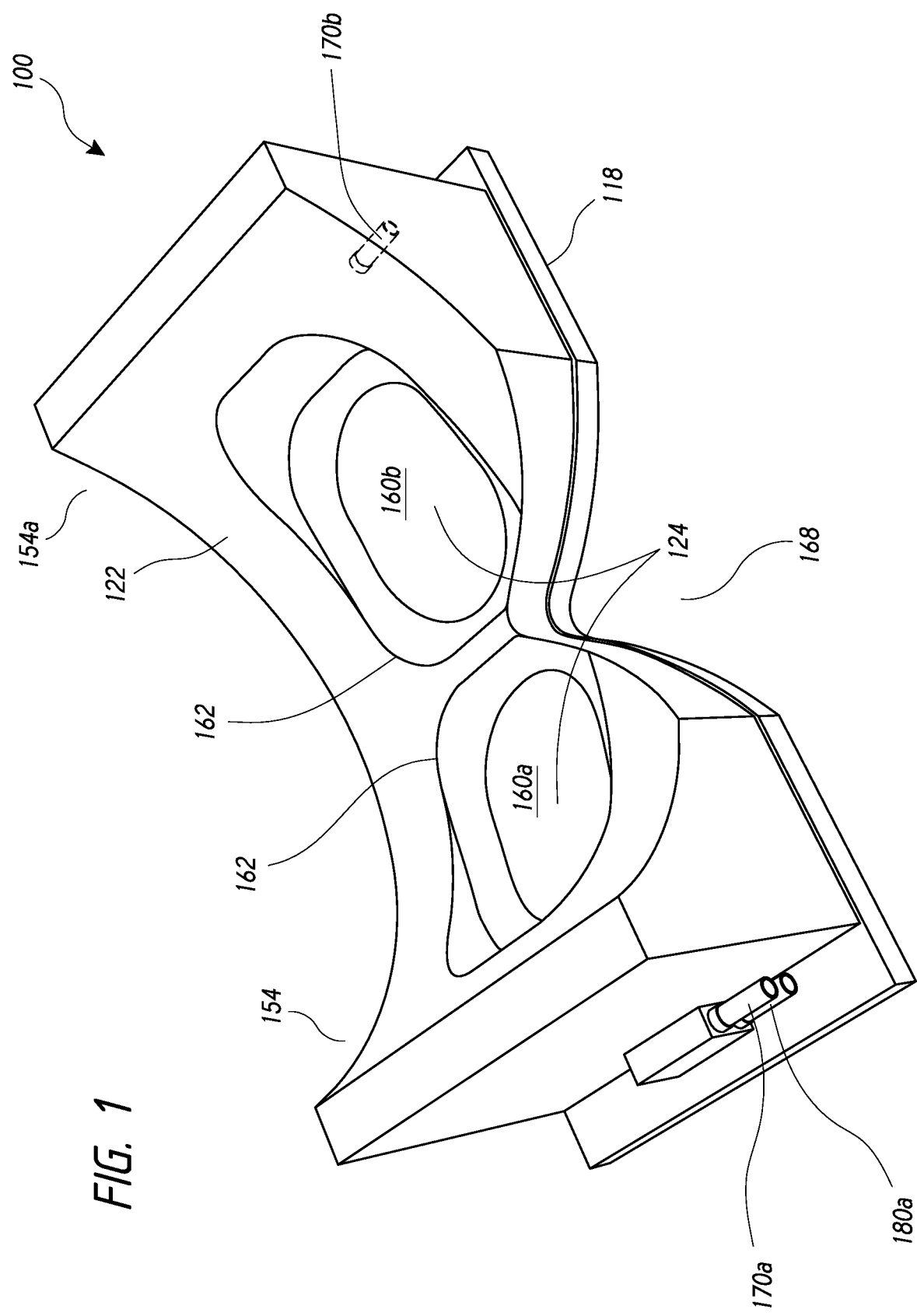
FIG. 1 schematically illustrates a perspective view of one embodiment of a mask which is inflatable and includes a framework that forms two cavities for the oculars.

Referring to FIG. 1, in one embodiment, a mask 100 includes a distal sheet member (distal portion) 118 which has optically transparent sections 124, and a proximal inflatable member (proximal portion) 154 having a generally concaved rear surface 122. In use, the rear concaved surface 122 faces the patient's face and conforms to the patient's face, according to some embodiments. As used herein the terms "user" or "patient" or "subject" or "wearer" may be used interchangeably. Still Referring to FIG. 1, the inflatable member 154 can have two cavities 160a, 160b which are aligned with the optically transparent sections 124. In some embodiments, the cavities 160a, 160b extend from a distal sheet 118 to the rear concave surface 122 and define two openings 162 on the rear concave surface 122. In use, the patient's eyes align with the two cavities 160a, 160b, so that the rear concave surface 122 forms seals around the patient's eye sockets or face, e.g. forehead and cheeks, inhibiting flow of fluid into and out of the cavities 160a, 160b. In addition, the mask 100 can include ports 170a-b, 180a-b which provide access to control flow of fluid (e.g. air) into and out of the cavities 160a, 160b.

Figure 2A:
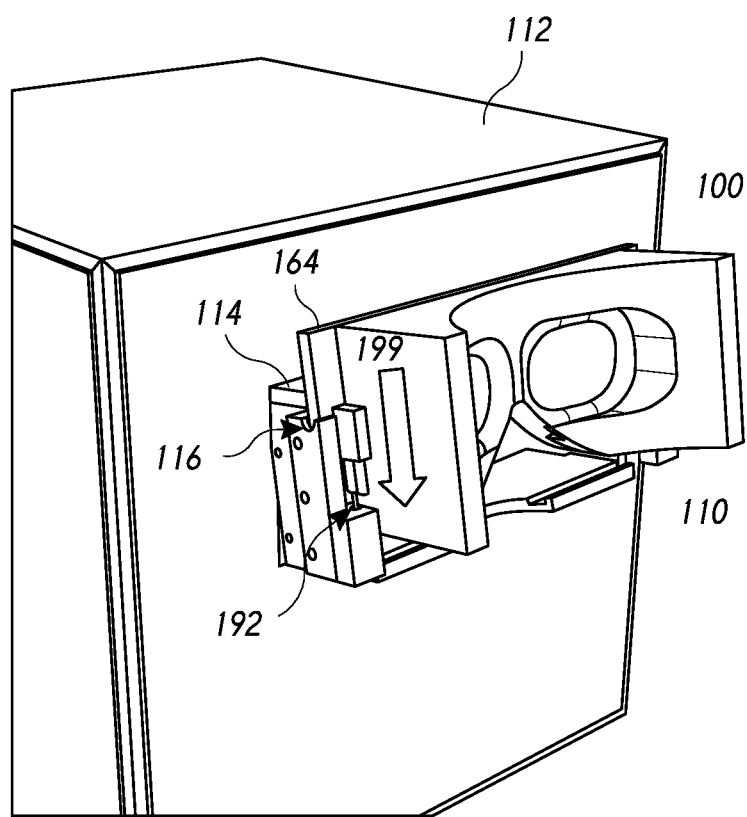
FIGS. 2a-2b schematically illustrates a mask removably attached to a medical device.
Figure 2B:
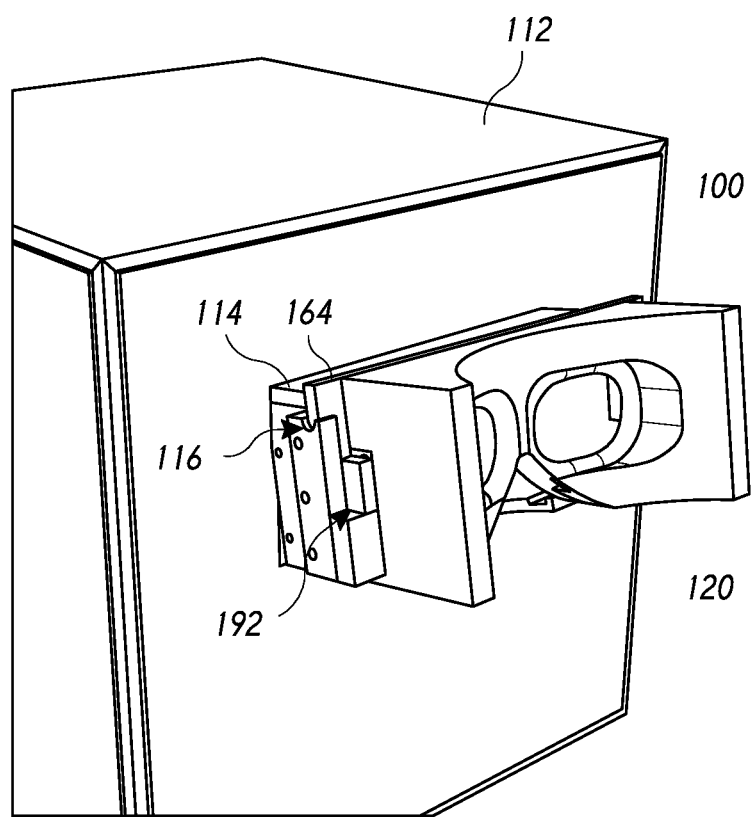

In some embodiments, the mask 100 can interface with a medical device. With reference to FIGS. 2a-2b, there is illustrated one embodiment whereby the mask 100 is placed on a separate device 112. In some embodiments, the separate device 112 is a medical device, such as a diagnostic or therapeutic device. In some embodiments, the separate device 112 is an ophthalmic device, such as a device for the eye, and may be an optical coherence tomography device ("OCT") that may contain a housing and instrumentation contained therein. The mask 100 may be used with a wide range of medical devices 112, such as for example an OCT device such as disclosed herein, as well as other OCT devices and other medical devices 112. In some embodiments, the medical device 112 can receive and removably connect to the mask 100. The mask 100 can be configured to connect to the medical device 112, adhere to one or more surfaces of the medical device 112, or be mechanically fixed to the medical device 112, or be secured to the medical device 112 in any other way (e.g. clamps, straps, pins, screws, hinges, elastic bands, buttons, etc.), such that the mask 100 is removable from the medical device 112 without damaging the mask 100.

In one embodiment, a docking portion 114, which may include an optical interface such as for example a plate, can be included on the medical device 112. The docking portion 114 can also include a slot 116 for receiving a mask 100. In some embodiments, the mask 100 includes a flange 164 that extends laterally outward past a side of the inflatable member 154 on the distal sheet 118 for slideably engaging with the slot 116. The mask 100 can be inserted into the slot 116 and slide down to a final locking position 120. In another embodiment, the flange 164 can be on the medical device 112 and the slot 116 can be on the mask 100.

Figure 3:
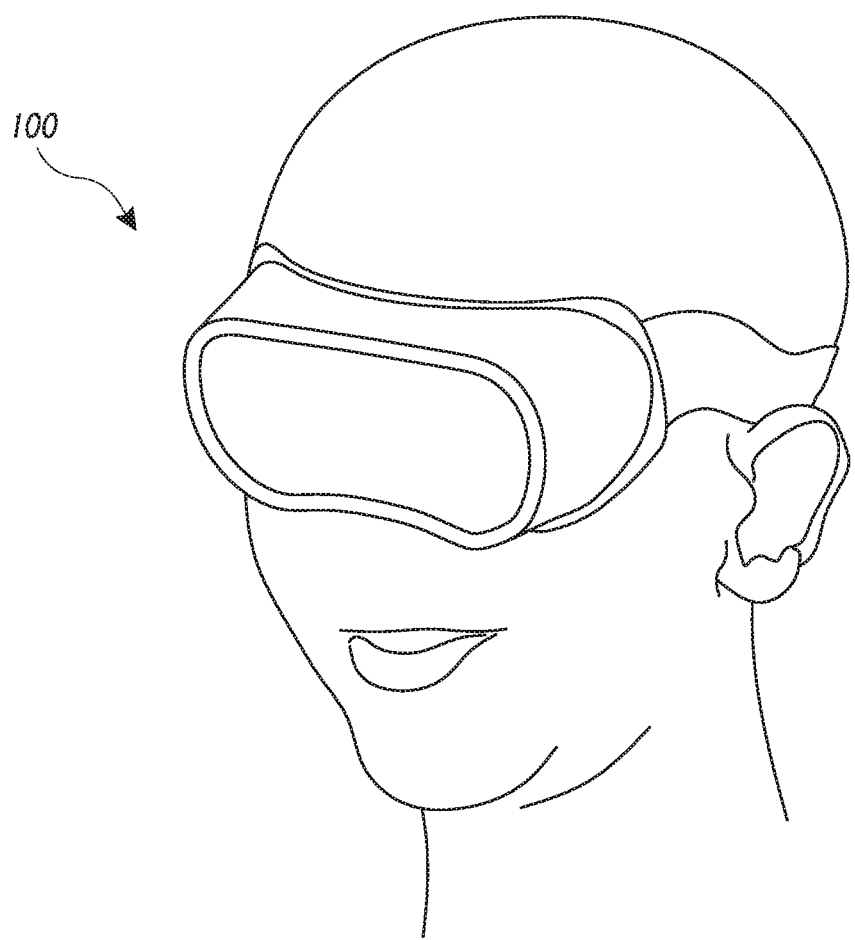
FIG. 3 schematically illustrates a user wearing a mask that provides, for example, an interface to a medical device such as a diagnostic device that is used by many patients.

With reference to FIG. 3, there is illustrated an example of a mask 100 worn by a user over the user's eyes. In various embodiments, the mask 100 may be removably attached to the wearer with an adhesive, an elastic band, a Velcro band, a strap, a buckle, a clip, and/or any other suitable fastener or mechanism. In some embodiments, the mask 100 can include mechanisms for both attaching to the wearer and attaching to the medical device 112. In other embodiments, a patient may use the mask 100 without any straps, bands, etc. that attach to the user. For example, referring to FIGS. 2a-b, the patient may simply move his/her face in alignment and in contact with the mask 100, which is secured to the medical device 112. In another embodiment, a patient who has a mask 100 secured to his/her face may position himself/herself properly with respect to the medical device 112, so that the distal sheet 118 interfaces with the medical device, 112, and the medical device 112 can take readings.

Figure 4:
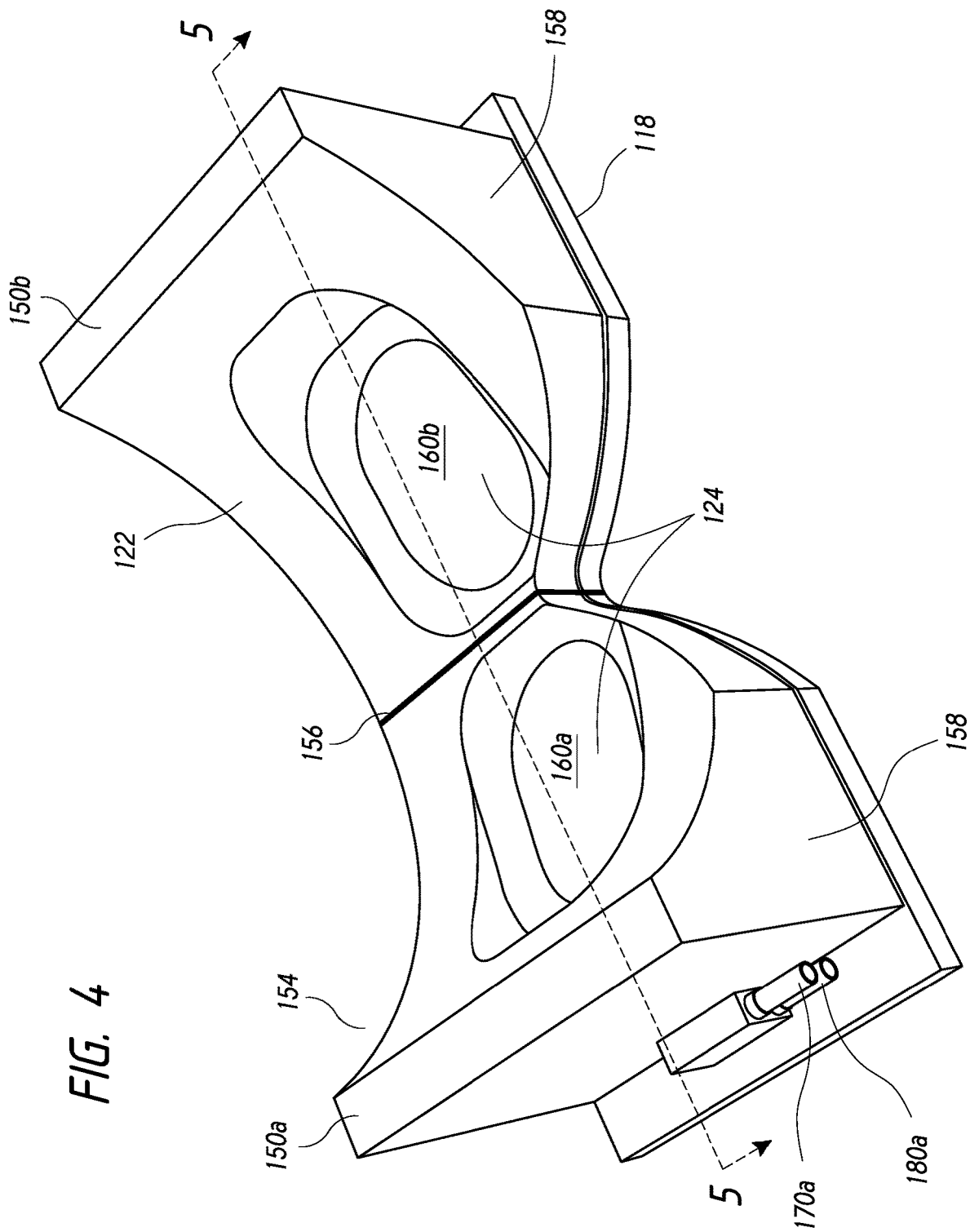
FIG. 4 schematically illustrates a perspective view of another embodiment of a mask with an inflatable framework that is partitioned into two separately inflatable sections.

Returning to FIG. 1, one embodiment of the mask 100 comprises an inflatable framework 154 having an inflatable chamber 154a, two cavities 160a, 160b, a frontward surface formed by a distal sheet member 118, and a rearward surface 122. It will be understood that "inflatable," as used herein, can include "deflatable," and vice versa. Thus, in some embodiments, an "inflatable" framework 154 or chamber 154a can be deflatable, and a "deflatable" framework 154 or chamber 154a can be inflatable. Referring to FIG. 1, cavities 160a, 160b may extend between the distal sheet member 118 and the rearward surface 122. In some embodiments, the frontward member 118 includes a window member 124, which can be substantially optically transparent in some embodiments, with minimal to no effects on the optics of a medical device 112 (e.g. an OCT device) which can interface with the mask 100, although some embodiments may introduce optical effects. In some embodiments, the distal sheet member 118 can be rigid. In some embodiments, the distal sheet member 118 can be made of polycarbonate, poly (methyl methacrylate), or glass. Other materials can be used. In other embodiments, the distal sheet member 118 can be flexible. The distal sheet member 118 can have a thickness of less than 0.1 mm, 0.1 mm, 0.5 mm, 1 mm, 2 mm, 4 mm, or more. In one embodiment, the window member 124 may be adjacent to the inflatable framework 154. Thus, the window member 124 may form a frontward surface of a cavity 160a, 160b. Further, the window member 124 may be aligned with the cavities 160a, 160b. In addition, the cavities 160a, 160b can define openings on the rearward surface, defined by perimeters 162. Referring to FIG. 4, the inflatable framework 154 can have two separately inflatable chambers 150a, 150b. Still referring to FIG. 4, in one embodiment, one inflatable chamber 150a can have a cavity 160a therein, and another inflatable chamber 150b can have another cavity 160b therein.

The distal sheet member 118 may be substantially flat and the rearward surface 122 may be generally curved and concave according to one embodiment. Referring to FIG. 4, in one embodiment the thickness of the mask 100 is thinnest at the center 156 and thickest toward the outer edges 158, with the thickness decreasing from the outer edges 158 toward the center 156, thereby defining a curved and concave rearward surface 122.

During use, a patient's face is brought in contact with the rearward surface 122 of the mask, such that the patient's eyes are aligned with the cavities 160a, 160b, and the patient "sees" into the cavities 160a, 160b. Thus in some embodiments, the cavities 160a, 160b may be referred to as ocular cavities 160a, 160b. In one embodiment, only the portion of the distal sheet member 118 that aligns with the patient's eyes may be optically transparent, with other portions opaque or non-transparent.

In some embodiments, the rear concaved surface 122 of the mask 100 can seal against a patient's face around the general area surrounding the patient's eyes sockets, thereby forming a seal around the patient's eye sockets. The seal may be air-tight and liquid-tight according to some embodiments. In some embodiments, a seal may be formed between the user and the mask 100 without the need for assistance from additional personnel. In some embodiments, various portions of the patient's face can form the seal around the ocular cavities 160a, 160b. For example, the patient's forehead, cheekbones, and/or nasal bridge (e.g. frontal bone, supraorbital foramen, zygomatic bone, maxilla, nasal bone) can form a seal around the ocular cavities 160a, 160b. As used herein, reference to a "peripheral region" around the eye socket shall refer to any combination of the above.

Figure 5:
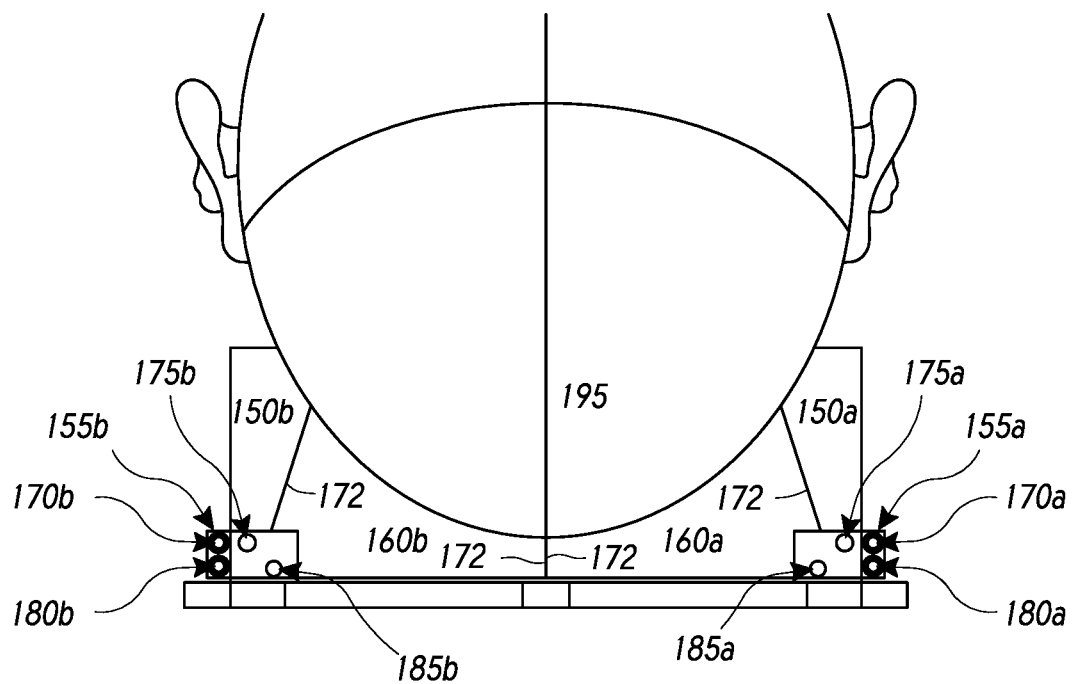
FIG. 5 schematically illustrates a cross section of the mask in FIG. 4 taken along the lines 5-5.

FIG. 5 illustrates a top view of a patient wearing a mask 100. The mask 100 in FIG. 5 is a cross-section of the mask 100 taken along line 5-5 in FIG. 4. Referring to FIG. 5, as seen from the view of the patient, the mask 100 comprises a right cavity 160b, such as a right ocular right cavity, a left cavity 160a, such as a left ocular cavity, a right inflatable chamber 150b, and a left inflatable chamber 150b. The walls 172 of the ocular cavities 160a, 160b, the window members 124, and the head of the user 195 may form an air-tight enclosed area. The head of the user 195 (e.g. the peripheral region around the user's eye sockets) forms a seal with the rearward perimeters 162 of the cavities 160a, 160b, thus allowing the cavities 160a, 160b to hold air or fluid. This seal may be capable of holding air or fluid pressures of, for example, 0.5 psi, 1 psi, or 5 psi or pressures therebetween. Higher or lower pressures are also possible.

Still referring to FIG. 5, some embodiments include inlet assemblies 155a, 155b. The inlet assemblies may include ports 170a-b, 180a-b, allowing access to the inflatable chambers 150a, 150b, and/or the cavities 160a, 160b.

Air, fluid, and/or other substances can be introduced into the ocular cavities 160a, 160b, via ports 180a, 180b, 185a, 185b. Air may be introduced into the left ocular cavity 160a by supplying an air source (e.g. via a pump) to the port at 180a. Thus, following the path of the air, the air may enter the port at 180a, then exit the port at 185a and into the leftocular cavity 160a (180a and 185b represent two ends of the same path). Similarly, regarding the right ocular cavity 160b, air may enter the port at 180b, then exit the port at 185b and into the right ocular cavity 160b.

Accordingly, in some embodiments, pressure inside the ocular cavities 160a, 160b may be controlled by adjusting the amount of air into and out of the ports 180a, 180b. Further, the air tight seal formed between the patient's face and the mask 100 can prevent unwanted leaks into or out of the ocular cavities 160a, 160b. This can be advantageous when air or fluid is used to challenge or test a body function. For example, air pumped into sealed air chamber cavities 160a, 160b in front of the eye can create positive pressure which can be used to press on the eye for the purposes of measuring the force of globe retropulsion or measuring intraocular pressure. In addition, air can be directed to the cornea, which is imaged with OCT. In some embodiments, air is pumped into the ocular cavities 160a, 160b to achieve a pressure of up to 1-2 psi. In some embodiments, the air supplied to the ocular cavities 160a, 160b is supplied by ambient surroundings, such as the ambient air in a clinical room using for example a pump.

In some embodiments, chamber ports 170a, 170b, 175a, 175b provide access to inflatable chambers 150a, 150b for inflating or deflating the chambers 150a, 150b. The chambers 150a, 150b may be inflated by introducing an air source (e.g. via a pump) to the ports at 170a, 180a. Thus, for example, following the path of the air, the air may enter the port at 170a, then exit the port at 175a and into the left inflatable chamber 150a, thereby inflating that chamber 150a. The right chamber 150b may be inflated in a similar manner. Negative pressure (e.g. a vacuum) can be applied to the ports 170a, 170b connected to the inflatable chambers 150a, 150b, thereby deflating the chambers 150a, 150b. As used herein, "deflating" shall include applying negative pressure.

In some embodiments, inflating the chambers 150a, 150b can cause the mask 100 to conform to the contours of a user's face. In addition, deflating the chambers 150a, 150b can cause the mask 100 to conform to the contours of a user's face. Further, inflating or deflating the chambers 150a, 150b can adjust a thickness of the mask 100, thus changing the distance between a user (who may face the rear concaved surface 122) and a medical device 112 (which may be interfaced with the distal sheet member 118).

In various embodiments, a port 170a-b, 180a-b is provided for each chamber 150a, 150b and cavity 160a, 160b. For example, referring to FIG. 5, there is illustrated a port 185b for the right cavity, a port 175b for the right inflatable chamber 150b, a port 185a for the left cavity 160a, and a port 175a for the left inflatable chamber 150a.

In one embodiment, two ports may be provided for one inflatable framework 154. For example, returning to FIG. 1, one port 170b is provided on the right side of the inflatable framework 154, and another port 170a is provided on the left side of the inflatable framework 154. Providing two ports for one chamber 154 can help to equalize the distribution of substances (e.g. air or fluid) in the chamber 154 by allowing access to the chamber 154 at different regions. In one embodiment, the inflatable framework 154 does not include any ports. For example, the inflatable framework 154 may be pre-formed as desired, by filling it with a desired volume of fluid or air. Ports 170a-b, 180a-b may be added, removed, arranged, or configured in any suitable manner.

In some embodiments, the mask 100 advantageously can conform to a patient's face, thereby allowing the formation of a complete air-tight seal between the peripheral region around a user's eye sockets and the rear concaved surface 122 around the ocular cavities 160a, 160b. Accordingly, the rearward perimeter 162 of the cavities 160a, 160b can be configured to sealingly engage a periphery of a patient's eye socket. In some embodiments, the mask 100 includes a recess 168 (see e.g. FIGS. 1, 4, 6), allowing room for a patient's nose, so that the mask 100 forms a seal against the parts of a patient's face with a lower degree of curvature, increasing the surface area of the patient's face to which the mask 100 conforms.

In one embodiment, the air-tight seal can be formed by inflating the inflatable framework 154. In some embodiments, the inflatable framework 154 can resemble a bag. In some embodiments, a mask 100 with a relatively deflated framework 154 is provided to a patient. Because the bag 154 is deflated, it may exhibit some "slack." The patient's face may be brought in contact with the mask 100, and then the bag 154 may be inflated, causing the bag 154 to inflate around the contours of the patient's face and thereby conform to the patient's face. Accordingly, a complete air-tight seal can be formed between the patient's face and the rear concaved surface 122 around the ocular cavities 160a, 160b. The bag 154 may be inflated by introducing air, gas, fluid, gel, or any other suitable substance. In addition, the bag 154 can be deflated, causing the mask 100 to disengage from the patient's face, according to one embodiment.

In one embodiment, an air-tight seal is formed by applying a vacuum to the inflatable framework 154. In some embodiments, when the framework 154 is filled with particulate matter, such as coffee grounds, a plasmoid transformation to a semi-solid but form-fitting filler can be achieved by subjecting the particulate matter to a vacuum. For example, the framework 154 can be molded into shape easily when particulate matter is loosely contained in the framework 154, similar to a bean bag. A patient's face may then be brought into contact with the mask 100. Applying a vacuum to the bag 154 causes the particulate matter to pack tightly, thereby causing the bag 154 to conform to the contours of a patient's face. The tightly packed particulate matter can thus undergo a plasmoid transformation to a solid, while still allowing the framework 154 to conform to the patient's face and create an air-tight seal.

To facilitate the seal between a patient and the cavities 160a, 160b, the mask 100 can be configured with a lip 194 around the perimeter 162 of a cavity 160a, 160b, as illustrated in FIG. 6. FIG. 6 illustrates a lip 194 with a cut-away portion 161 showing the curvature of the lip 194. In one embodiment, the lip 194 comprises a first end 196 attached to the perimeter 162 of the cavity 160a, 160b and a second end 198 extending partially into the cavity 160a, 160b. In one embodiment, the edge 198 of the lip 194 may extend more or less and curl inward, as illustrated in FIG. 6. In one embodiment, the first end 196 and second end 198 define a curve, such that the lip 194 curls inwardly partially into the cavity 160a, 160b. Further, the lip 194 can be flexible and configured to extend in a rearward direction (e.g. toward the rearward surface 122). Thus, when pressure is introduced inside the cavity 160a, 160b, and pressure exerts a force in a rearward direction, the lip 194 can move rearwardly. When the inflatable framework 154 is sealed with a peripheral region around a user's eye socket, and the lip 194 moves rearwardly, the lip 194 can seal against the user's eye socket, preventing pressure from escaping.

In some embodiments, the mask 100 can be configured to be comfortable by filling the chambers 160a, 160b with soft gel fillers, particulate fillers such as foam beads or sand, or air fillers.

In one embodiment, the mask 100 can be custom made to fit the specific patient using it. For example, the mask 100 may be molded for a specific patient in a clinic. Thus, the mask 100 can be uniquely customized for a particular patient according to one embodiment. In another embodiment, the mask 100 is a "one size fits all" mask 100. Other embodiments are possible, including differential sizing based on age, height or facial structure. In some embodiments, the mask 100 is pre-inflated. In addition, air-tight seals can be formed between the rear curved surface 122 of the mask around the ocular cavities 160a, 160b and the peripheral region around a patient's eye sockets (e.g. via a lip) when the mask 100 is pre-inflated.

Figure 7A:
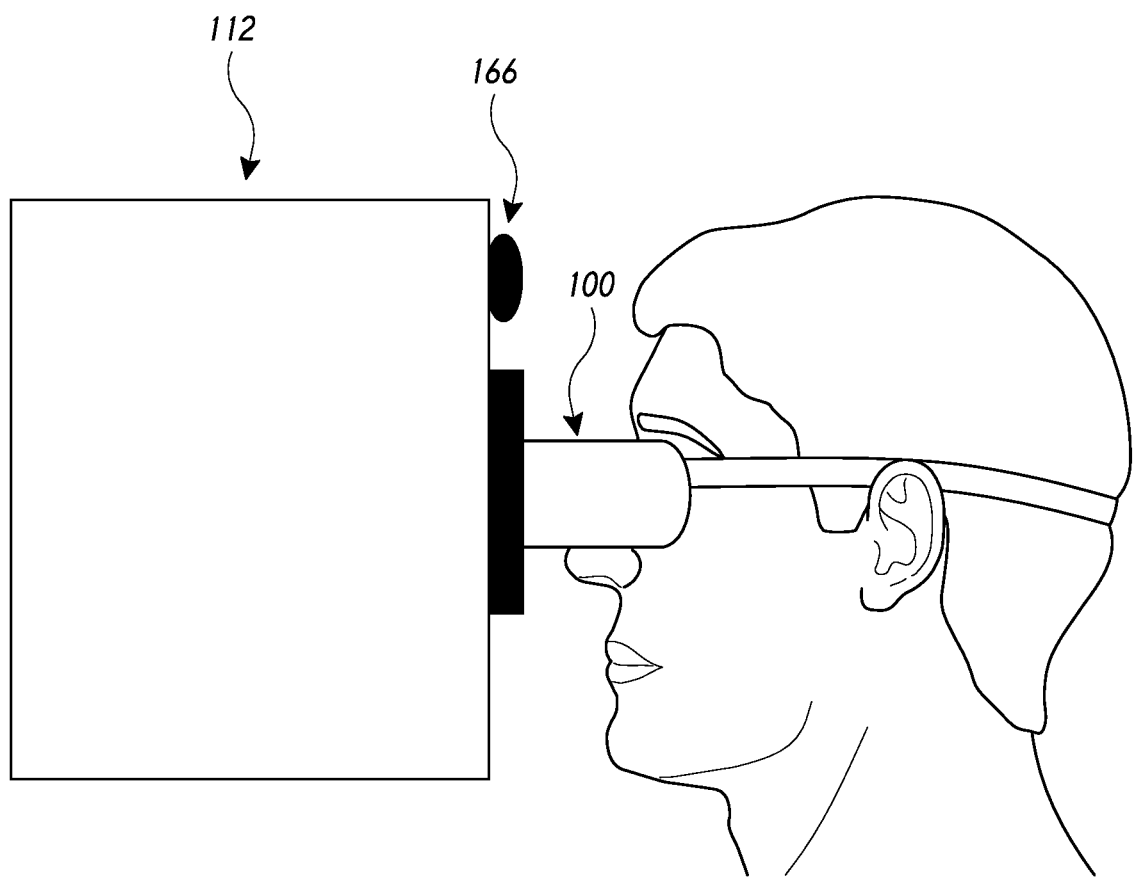
FIG. 7a schematically illustrates a side view of one embodiment of a mask displaced a first distance from a medical device.
Figure 7B:
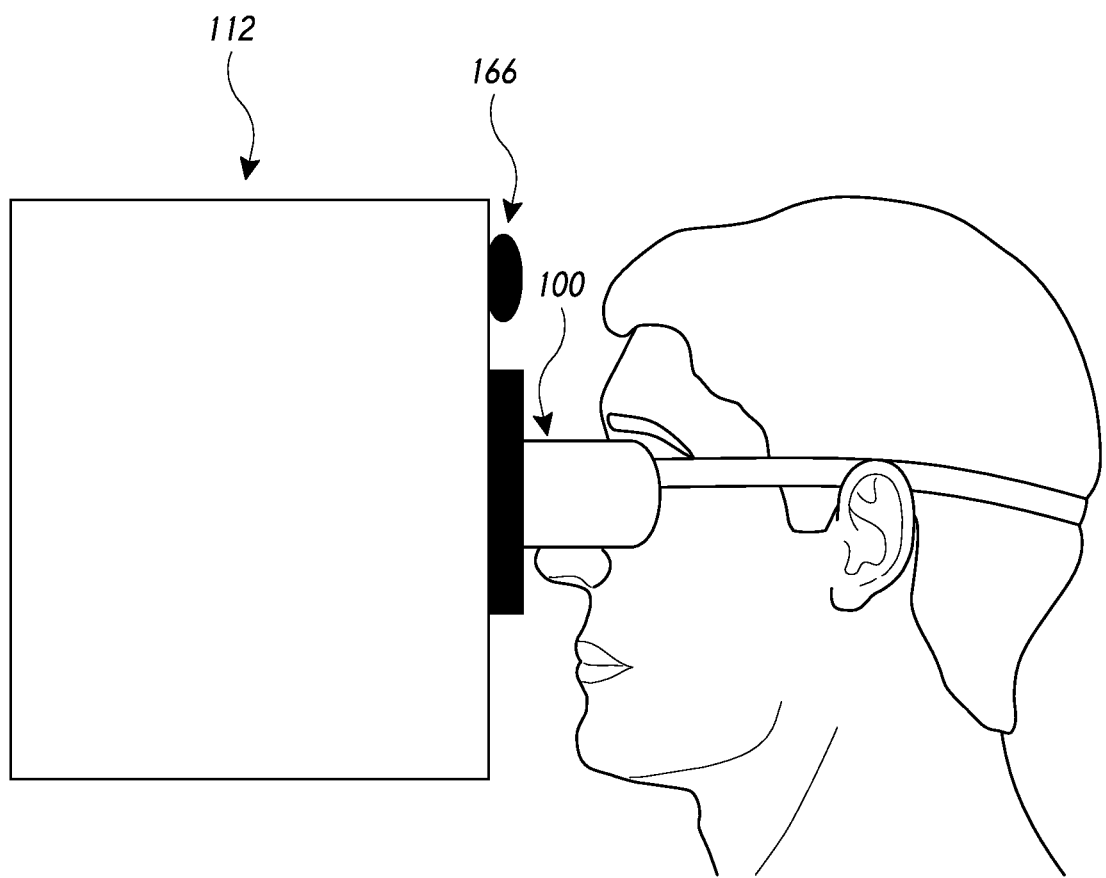
FIG. 7b schematically illustrates a side view of another embodiment of a mask displaced a second distance from the medical device.

FIGS. 7a-7b illustrate side views of a user with a mask 100 being examined or treated by a medical device 112 according to one embodiment.

It will be appreciated that the FIGS. 7a-7b are schematic drawings and may possibly exaggerate the variation in size for illustrative purposes. The medical device 112 shown in FIGS. 7a-7b can be an OCT device. Inflating the mask 100 can increase the thickness of the mask 100, so that the mask 100 can move the patient toward or away from the device 112 when it is deflated or inflated respectively. For example, FIG. 7a illustrates a relatively deflated mask 100, with a user relatively close to the device 112. FIG. 7b illustrates a relatively inflated mask 100, with the user relatively farther from the mask 100. "Inflating" or "inflated" may include a mask 100 in a fully inflated state, or a mask 100 in a less than fully inflated state, but still in a state that is more inflated relative to a previous state (e.g. a deflated state) or at least partially inflated. Similarly, "deflating" or "deflated" may include a mask 100 in a fully deflated state, or a mask 100 in a less than fully deflated state, but still in a state that is more deflated relative to a previous state (e.g. an inflated state) or at least partially deflated.

A patient location sensor 166 can be included in order to detect how close or how far the user is from the medical device 112. If the user is not at a desired distance from the device 112, the framework 154 on the mask 100 can be inflated or deflated to bring the user to the desired distance. Any variety of sensors 166 can be used to detect the distance between the user and the medical device 112, according to sensors known in the art. In one embodiment, a patient location sensor 166 can be included with the medical device 112 in alignment with the user's forehead, as illustrated in FIGS. 7a-7b. Thus, the location sensor 166 can measure, for example, the distance or relative distance from the forehead to the medical device 112. In one embodiment, the sensor 166 can be a switch, which can be actuated (e.g. activated or depressed) when the user's forehead presses against the switch when the user is close to the medical device 112. In addition, other types of sensors in different locations could measure the distance between the user and the medical device 112. In one embodiment, the location sensor 166 is not placed on the medical device 112, but is placed in a location that can still detect the distance between the user and the medical device 112 (e.g. on the walls of a room in which the medical device 112 is located). In one embodiment, the information regarding the distance between the user and the medical device 112 is provided by an OCT device.

Figure 8:
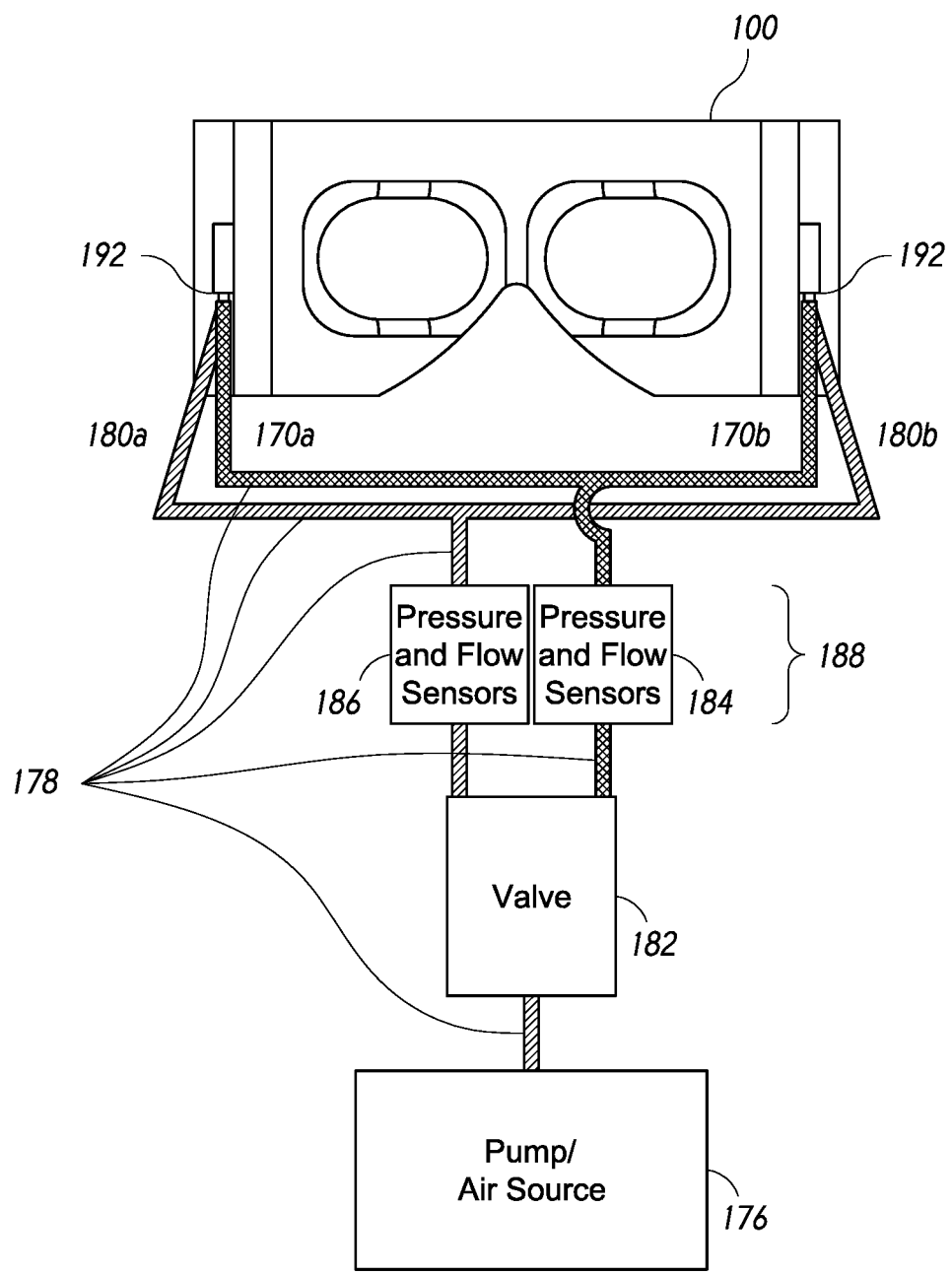
FIG. 8 schematically illustrates a schematic diagram of a system for controlling, monitoring, and providing fluid to a mask.

FIG. 8 illustrates a system 174 for controlling, monitoring, and providing air to the inflatable mask 100. The system 174 can be used to control a patient's distance from the medical device 112, the patient's movement to and from the medical device 112, the seal between the mask 100 and the patient's face, and/or pressure in the ocular cavities 160a, 160b of the mask 100.

Referring to FIG. 8, the system 174 can include pumps 176, an air source 176, conduits 178, valves 182, pressure sensors 188, flow sensors 188 and/or processors (not shown). In addition, air into and out of the inflatable chambers 150a, 150b and/or cavities 160a, 160b can be controlled by similar components. Referring to FIG. 7b, the air source/pump 176, valves 182, sensors 188, and the mask 100 can be in fluid communication with each other via conduits 178. In addition, the air source/pump 176, valves 182, and sensors 188 can be in electronic communication with a processor. Further, the processor can be in communication with electronics associated with a medical device 112, such as an OCT device.

In some embodiments, the air source/pump 176, conduits 178, valves 182, sensors 188, and processors can be contained within a single unit, such as a medical device 112. In other embodiments, the components may be spread out across several devices external to a medical device 112.

Referring to FIG. 8, the mask 100 can be connected to an air source/pump 176, which can comprise compressed air, ambient air from the environment of the mask (e.g. in a clinical room), a reservoir, a sink (e.g. for providing water to the mask 100), an automatic pump, manual pump, hand pump, dispenser, or any other suitable air source/pump.

Valves 182 can also be included in the system 174 for increasing, decreasing, stopping, starting, changing the direction, or otherwise affecting the flow of air within the system 174. In some embodiments, the valves 182 can direct air to an exhaust port, in order to vent air in the cavities 160a, 160b or inflatable chambers 150a, 150b. In some embodiments, valves 182 are not included in the ports 170a-b, 180a-b of the mask 100, and are external to the mask 100. In some embodiments, valves 182 can be included in the ports 170a-b, 180a-b of the mask 100.

In some embodiments, the system can also include an ocular pressure sensor 186 to sense the pressure inside the ocular cavities 160a, 160b. Readings from the pressure sensor 186 can be used for intraocular pressure and retropulsion measurements. In addition, the system 174 can include a chamber pressure sensor 184. In some embodiments, the chamber pressure sensor 184 can be used to determine whether a patient is pressing their face against the mask 100, or how hard the patient is pressing their face against the mask 100.

A flow sensor 188 can also be provided to measure the volume of flow into and out of the ocular cavities 160a, 160b and inflatable chambers 150a, 150b. Flow sensors 188 may be useful when, for example, the inflatable chamber 150a, 150b is underinflated such that the pressure inside the inflatable chamber equals atmospheric pressure. In such a case, pressure sensors 188 may not be useful but a flow sensor 188 can measure the volume of fluid pumped into the inflatable chamber 150a, 150b. In some embodiments, one set of sensors can be provided for the ocular cavities 160a, 160b, and another set of sensors can be provided for the inflatable chambers 150a, 150b.

Referring to FIG. 8, the conduits 178 can convey the flow of air (or gas, liquid, gel, etc.) between the pump/air source 176, valves 182, sensors 188, and the mask 100. In some embodiments, the valves 182 can be downstream of the pump/air source 176, the sensors 188 can be downstream of the valves 182, and the mask 100 can be downstream of the sensors 188.

In some embodiments, the conduit 178 terminates at conduit ends 192, shown in FIGS. 2a-2b. The conduit ends 192 can be designed to couple with the ports 170a-b, 180a-b of the mask 100. Referring to FIGS. 2a-b, in some embodiments, the ports 170a-b, 180a-b of the mask 100 can include a male portion (e.g. a luer lock taper connector), and the conduit ends 192 can include a female portion.

In some embodiments, the ports 170a-b, 180a-b of the mask 100 can include a female portion, and the conduit ends 192 can include a male portion. In addition, the conduit ends 192 and the ports 170a-b, 180a-b can contain flanges, tubings, or any other mechanism for coupling with each other. When the ports 170a-b, 180a-b are coupled to the conduit ends 192, an air-tight seal for fluid flow between the mask 100 and the system can be created.

Referring to FIG. 2a, in some embodiments, one movement (e.g. pressing the mask 100 down in the direction of the arrow 199) can connect all four ports 170a-b, 180a-b to the conduit ends 192 at the same time. In some embodiments, the conduit ends 192 extend to the exterior of the medical device 112, and the conduits 178 can be connected to the exterior ports 170a-b, 180a-b one at a time. In some embodiments, the conduits ends 192 are located on the medical device 112, and a separate conduit piece can connect the conduit ends 192 to the external ports 170a-b, 180a-b.

In some embodiments, the system 174 can be used in clinical settings, such as during a medical visit (e.g. a medical examination). The components can be utilized in a variety of different ways and combinations during the medical treatment.

For example, during a medical diagnostic or treatment, referring to FIG. 2a, the mask 100 can be interfaced with the medical device 112 by aligning the ports 170a-b, 180a-b of the mask 100 with the conduit ends 192 in the medical device 112, and pushing down on the mask 100.

The patient's head can be brought into contact with the rear concaved surface 122 of the mask 100, and system 174 can inflate or deflate the inflatable chambers 150a, 150b, so that the mask 100 conforms to the patient's face, thereby forming an air-tight seal around the ocular cavities 160a, 160b.

During the procedure, the system 174 can change the pressure in the air-tight ocular cavities 160a, 160b by a desired amount depending on the medical examination being taken. The pressure sensor 186 can sense the amount of pressure in the ocular cavities 160a, 160b, and send that data to the processor. In addition, the system 174 can vary the pressure in the ocular cavities 160a, 160b during the procedure. For example, the processor can increase the pump 176 speed or change the valve state 182 so that flow is restricted.

Other components in the medical device 112 can also take measurements, such as ocular measurements, which can be combined with the data sent by the pressure sensors. For example, optical imaging components can measure changes in curvature or position of the anterior of the eye and in some embodiments, compare those changes to changes in the position or curvature of posterior of the eye. In addition, changes in the locations and distances of tissues, such as in the eye, can be imaged based on the pressure in cavities 160a and 160b sensed by the pressure sensors. Thus various pieces of data can be analyzed and processed into meaningful medical information.

Further, during the procedure, the system 174 may receive data from a patient location sensor 166 (see e.g. FIG. 7a-7b) indicating the distance between the patient and the medical device 112. The processor may determine that the patient should be positioned closer to or farther away from the medical device 112, in order to obtain more accurate and precise readings. Thus, the processor may use the location of the patient to modulate the inflation or deflation of the mask 100 more or less (e.g. by changing pump speed, changing valve state, etc.), in order to bring the patient closer to or farther away from the medical device 112.

In some embodiments, the processor can switch on the pump/air source 176 and open the valves 182 to introduce air into the ocular cavities 160a, 160b or inflatable chambers 150a, 150b according to a preset pressure or flow volume goal. In addition, flow in the system can be reversed to deflate the inflatable chambers 150a, 150b.

The mask 100 may include a mechanism for easily identifying a patient according to one embodiment. For example, the mask 100 may include an RFID tag, bar code or QR code, or other physical embodiment, to identify the wearer to other devices. Thus, for example, when a patient with a certain mask 100 nears the medical device 112, the system can determine who the patient is, and execute instructions tailored for the patient (e.g. how much air is needed to properly inflate the framework 154, how much pressure should be applied to the ocular cavities 160a, 160b, what readings the medical device 112 should take, etc.)

The mask 100 can be made of a material, such as plastic (e.g. polyethylene, PVC), rubber paper, or any other suitable material. In various embodiments, the mask 100 can be configured to be disposable by making it out of inexpensive materials such as paper, rubber or plastic. In various embodiments, the mask 100 can be configured to be reusable and easily cleaned either by the wearer or by another person.

In some embodiments, the mask 100 can provide a barrier between the patient and the medical device 112, increasing cleanliness and serving hygienic purposes.

In one embodiment, the mask 100 can be configured to create a barrier to external or ambient light, such as by constructing the mask 100 out of opaque materials that block light transmission. Accordingly, the mask 100 can prevent ambient light from interfering with medical examination measurements, such as optical devices, and ensure the integrity of those measurements.

Although examples are provided with reference to "air" (e.g. introducing air into the inflatable chamber, introducing air into the ocular cavities), it will be appreciated that other substances besides air can be used, such as gas, fluids, gel, and particulate matter.

Although examples are provided with reference to a mask 100 for a binocular system, it will be appreciated that the embodiments disclosed herein can be adapted for a monocular system. Thus, in one embodiment, the mask 100 includes an inflatable framework 154 defining one cavity instead of two, and that cavity can form a seal against the periphery of one eye socket. Further, while examples are provided with reference to eye sockets and eye examinations, it will be appreciated that the embodiments disclosed herein can be used with other tissues and medical applications.

In other embodiments, an inflatable device may cover different body tissues such as gloves for the hands, stockings for the feet or a hat for the head. In various embodiments, the inflatable device may include a cavity similar to the ocular cavity in the mask and may have at least one port to provide access to the cavity and change pressure therein or inflow gas therein or outflow gas therefrom, as well as a port to inflate the inflatable devices.

The inflatable mask can be used in a wide variety of clinical settings, including medical examinations and encounters that may be assisted by automated systems. Various embodiments of an automatic encounter portal are described below.

Electronic Encounter Portal

Medical encounters can be commonly comprised of administrative tasks, collection of examination data, analysis of exam data, and formation of an assessment and plan by the healthcare provider. In this context, a healthcare provider may be a licensed healthcare practitioner, such as a medical doctor or optometrist, allowed by law or regulation to provide healthcare services to patients. Examinations may be comprised of numerous individual tests or services that provide information for a healthcare provider to use to make a diagnosis, recommend treatment, and plan follow-up. The data from these tests that are collected for use by healthcare providers can be broken down into three rough categories: historical data, functional data and physical data.

Historical data can be collected in many ways including as a verbal person-to-person interview, a written questionnaire read and answered by the patient, or a set of questions posed by an electronic device either verbally or visually. Typical categories of historical information that are obtained in medical exams can include but are not limited to a chief complaint, history of present illness, past medical history, past ocular history, medications, allergies, social history, occupational history, family history, sexual history and a review of systems.

Functional data can be collected through individual tests of function and can be documented with numbers, symbols or categorical labels. Examples of general medical functions can include but are not limited to measurements of blood pressure, pulse, respiratory rate, cognitive ability, gait and coordination. Ophthalmic functions that may be tested during an exam can include but are not limited to measurements of vision, refractive error, intraocular pressure, pupillary reactions, visual fields, ocular motility and alignment, ocular sensation, distortion testing, reading speed, contrast sensitivity, stereoacuity, and foveal suppression.

Physical data can capture the physical states of body tissues and can be collected in many forms, including imaging, descriptions or drawings, or other physical measurements. This may be accomplished with simple measurement tools such as rulers and scales. It may also be accomplished with imaging devices, such as color photography, computed tomography, magnetic resonance imaging, and optical coherence tomography (OCT). Other means to measure physical states are possible. Physical measurements in general medical exams can include height, weight, waist circumference, hair color, and organ size. Ophthalmic structural measurements can include but are not limited to slit lamp biomicroscopy, retinal OCT, exophthalmometry, biometry, and ultrasound.

Currently, almost all of the individual tests that make up a medical examination are conducted by a human laborer often through the operation of a device. Whether this person is a healthcare provider or an allied healthcare professional, these laborers can be expensive, can often produce subjective results, and can have limitations on their working capacity and efficiency. Given the labor intensive nature of exams, healthcare care practices (which may also be referred to herein as "clinics" or "offices") and in particular eye care practices often employ numerous ancillary staff members for every healthcare provider and dedicate large areas of office space for waiting rooms, diagnostic equipment rooms and exam rooms. All combined, these overhead costs make healthcare expensive, inefficient and often prone to errors.

Automation is a well-known way of improving efficiency and capacity as well as reducing unit costs. Patient-operated or entirely operator-less devices may be preferable as labor costs increase and the need for objective, reproducible, digital, quantitative data increases.

Figure 9:
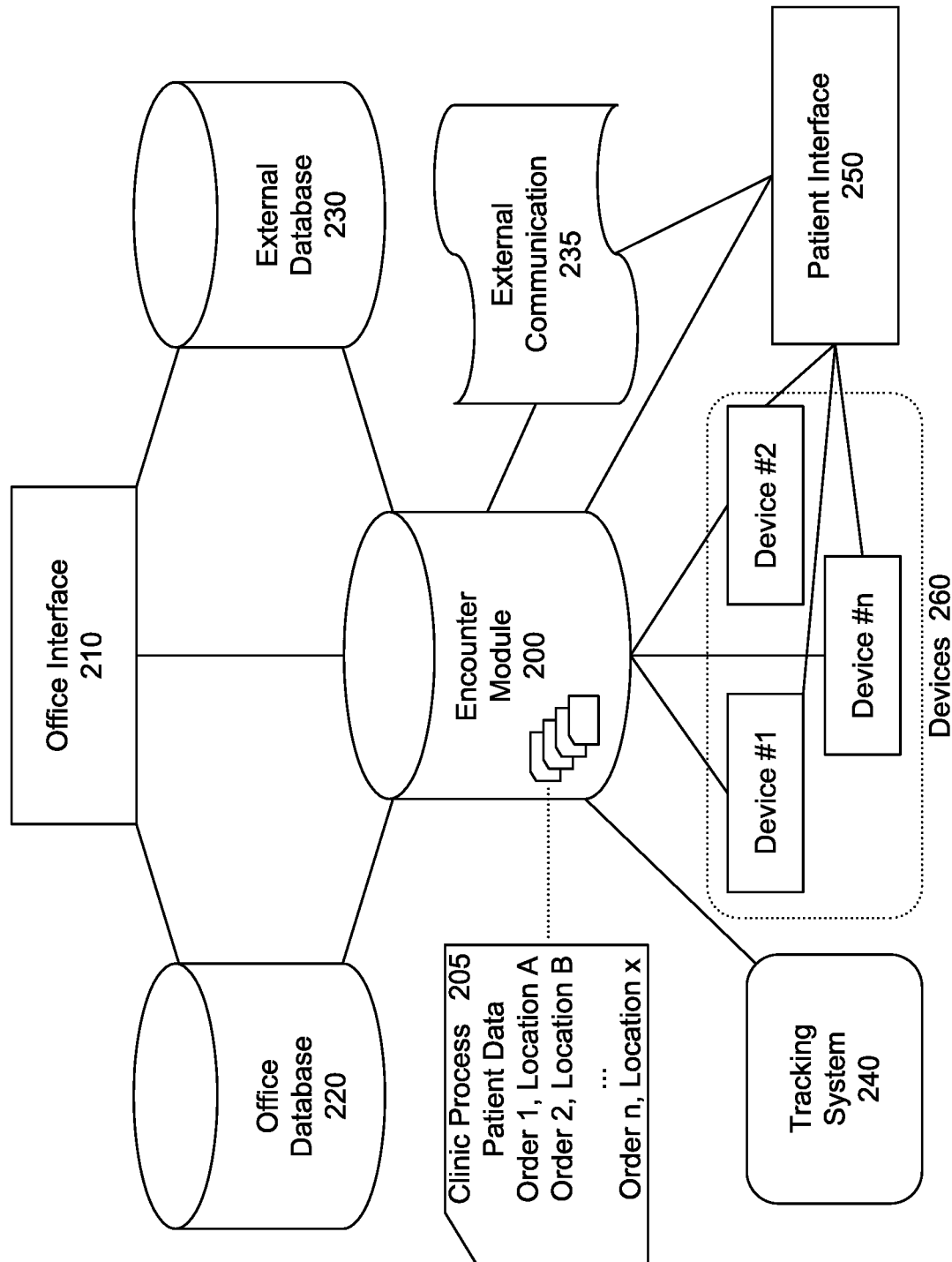
FIG. 9 schematically illustrates a schematic diagram an electronic exam portal.

With reference to FIG. 9, there is illustrated one embodiment of an electronic encounter portal. The encounter module 200 can be an electronic device that may be comprised of, for example, data storage, communication, or computer code execution capabilities and may contain information on patients registered for a healthcare encounter in an office.

The office interface 210 can be comprised of software that may be used by people to interact with the encounter module 200. Other software may also be included in the office interface 210. In one embodiment, the office interface 210 also can be comprised of an electronic device, such as a computer, tablet device or smartphone. In various embodiments, office staff can use the office interface 210 to, for example, create records or enter patient data into the encounter module 200 for patients who register in the clinic. This data entry can be enabled in many ways, including for example, manual entry, entry by copying previously-entered data from an office database 220, or entry using a unique identifier that can be compared to an office database 220 or external database 230, such as an Internet or cloud-based database, to retrieve pre-entered data for a patient matching that unique identifier. In one embodiment, registration can be completed with a code, such as an encounter code, in a fashion similar to checking in for an airline flight at an airport. This code could, for example, by linked to patient or provider information required for registration purposes.

The office database 220 can be configured to store data from past encounters, as well as other types of data. The external database 230 can be also configured to store at least data from past encounters, as well as other types of data. The encounter module 200 can be configured, for example, to access, copy, modify, delete and add information, such as patient data, to and from the office database 220 and external database 230. The external database 230 can be configured to, for example, receive, store, retrieve and modify encounter information from other offices.

In one embodiment, patients may self-register or check into the clinic by using the office interface 210 to, for example, create an encounter record, enter encounter information manually, select their information from a pre-populated office database 220, or enter a unique identifier that can be compared to an office 220 or external database 230 to retrieve their other associated data.

The encounter module 200 can be configured to contain patient records which may also contain clinic processes 205. A clinic process 205 can be comprised of, for example, orders from the healthcare provider for the patient's care. In one embodiment, the orders may indicate the sequence of evaluations and care. For example, a provider may indicate that a given patient should undergo a medical history followed by an examination with various medical devices followed by an assessment by the provider.

In one embodiment, the clinic process 205 can be configured to enable alteration of the orders, the order sequence or both the orders and their sequence by, for example, office staff or the provider. Examples of this could include insertion of an educational session about a given disease prior to a discussion with the provider, deletion of a treatment denied by a patient, or switching the sequence of two test procedures.

In some embodiments, the prescribed orders themselves may contain lists of prescribed tests to be performed on a given device. For example, as part of a technician work-up order, a provider may prescribe blood pressure and pulse measurement testing to be performed on a patient using a device in the clinic. The order and prescription of these tests may change throughout the encounter having been altered by office staff, the provider, or electronic devices.

In one embodiment, a diagnosis or medical history of a patient from the encounter module 200 can be included in the clinic process 205 and may be used, for example, to determine or alter the clinic process 205. For example, a history of past visits and evaluations may alter the tests that are ordered or the devices that are used during an encounter.

In one embodiment of an electronic encounter portal, a tracking system 240 can be configured to enable a component of an electronic encounter system to determine the physical location or position of, for example, patients, providers and staff in the office space. In one embodiment, a component of the electronic encounter system can use data from the tracking system 240 to monitor the progress of patients through a clinic process 205. In one embodiment, this tracking system 240 can be comprised of a sensing technology, such as a compass, radiofrequency antenna, acoustic sensor, imaging sensor, or GPS sensor that determines the position of the sensor in relation to known objects such as office walls, positioning beacons, WiFi transmitters, GPS satellites, magnetic fields or personnel outfitted with radiofrequency ID tags.

The tracking system 240 may also be configured to perform mathematical calculations, such as triangulation, to analyze signals from the sensors. The tracking system may also compare signals from the sensors to databases of known signals collected at a prior date, such as comparing a measured magnetic field to a database of known magnetic fields at every position in the clinic. In some embodiments, this tracking system 240 can also be comprised of an emission technology such as a radiofrequency beacon, to indicate the position of an object in the office space.

The tracking system 240 may also be configured to localize the position of a person or object using a known map of the office space as shown in FIG. 3. Knowledge of the position of sensors, patients or personnel in an office space map may enable the tracking system 240 to provide information to the encounter module 200 regarding the location of patients, providers or other office personnel in an office space.

The tracking system 240 can also be configured to provide position information to other components of the electronic encounter system, such as the office interface 210 or the patient interface 250, either directly or via an intermediate component such as the encounter module 200. An example of how this information might be used is to provide status information to a user as to the progress or status of other people in the office.

In one embodiment, office personnel can use the office interface 210 to monitor the location or progress of, for example, providers, staff or patients within the office space. This monitoring may include calculation of, for example, time spent in a given location, progress through a clinic process 205, or current status of activity, such as waiting, working or occupied. This monitoring ability can be advantageous so that office staff can, for example, monitor delays in the provision of patient care or identify recurrent patient flow bottlenecks that can be reduced through optimization of clinic flow.

The patient interface 250 can be comprised of software that may be used by patients to interact with the encounter module 200. In one embodiment, the patient interface 210 can also comprise an electronic device, such as a computer, tablet device or smartphone which can be supplied by the clinic or be supplied by the patient. For the purpose of clarity, in one embodiment, the patient interface 250 may be the patient's own electronic device, such as a smartphone or computer, that can be configured with patient interface 250 software. In other embodiments, the office interface 210 and the patient interface 250 may be the same device, such as with a mobile tablet computer or smartphone, that can be configured to allow a patient to perform actions of both an office interface 210, such as registration, and actions of a patient interface 250, such as viewing patient data or asking electronic questions of office personnel.

The encounter module 200 and the patient interface 250 can be configured to interface with various devices 260 in the clinic. These devices 260 can include but are not limited to diagnostic instruments, such as blood pressure monitors, imaging devices or other measurement instruments, or therapeutic devices, such as lasers or injection apparatuses. The encounter module and the patient interface 250 can be configured to send and receive data with these devices 260. Communication with these devices 260 can be enabled by but is not limited to wired connections, wireless connections and printed methods, such as bar codes or QR codes.

With reference to FIG. 3, there is illustrated a map of a healthcare office. In one embodiment, the patient can register for a healthcare encounter at the office entrance 300. In other embodiments, the patient may register for a healthcare encounter at a place other than entrance 300. In one embodiment, encounter registration can be completed by a human receptionist who may enter information into the encounter module 200 through the office interface 210. In another embodiment, registration may be completed by the patient for exemplary using an assisted or self-service kiosk configured with an office interface 210.

A kiosk may, for example, be comprised of a location where an untrained user can perform a task or tasks, such as checking in for an appointment or performing a requested test. This kiosk may be comprised of electronics or computer equipment, may be shielded from the view of other people in the same room, may be comprised of seating, and may provide a material result to a user. Other kiosk configurations are possible.

In another embodiment, the patient may register for the encounter with an office interface 210, such as a tablet computer, that is supplied by the clinic and may have been configured with software to interface with the encounter module 200. In still another embodiment, the user may register for the encounter with their own portable device, such as a mobile phone or tablet computer, that can be configured with software that can allow it to act as either or both an office interface 210 or as a patient interface 250.

In various embodiments, orders or steps in an electronic encounter system can include, for example, asking a patient to sit in waiting area 310, asking a patient to proceed to testing area 320 or asking a patient to go to clinic area 330. These orders can be conveyed to the patient by, for example, the patient interface 250 or by office personnel. In one embodiment, the desired disposition for a patient can be determined by a clinic process 205 that may have been entered into the encounter module 200 and communicated to the patient via the patient interface 250 or office personnel.

In one embodiment, the patient interface 250 can be configured to use information from the tracking system 240 for example, to determine the location of the patient in the clinic, to determine the next planned location for a patient from a clinic process 205 in the encounter module 200, or to communicate directions to a patient using the patient interface 250.

Figure 10:
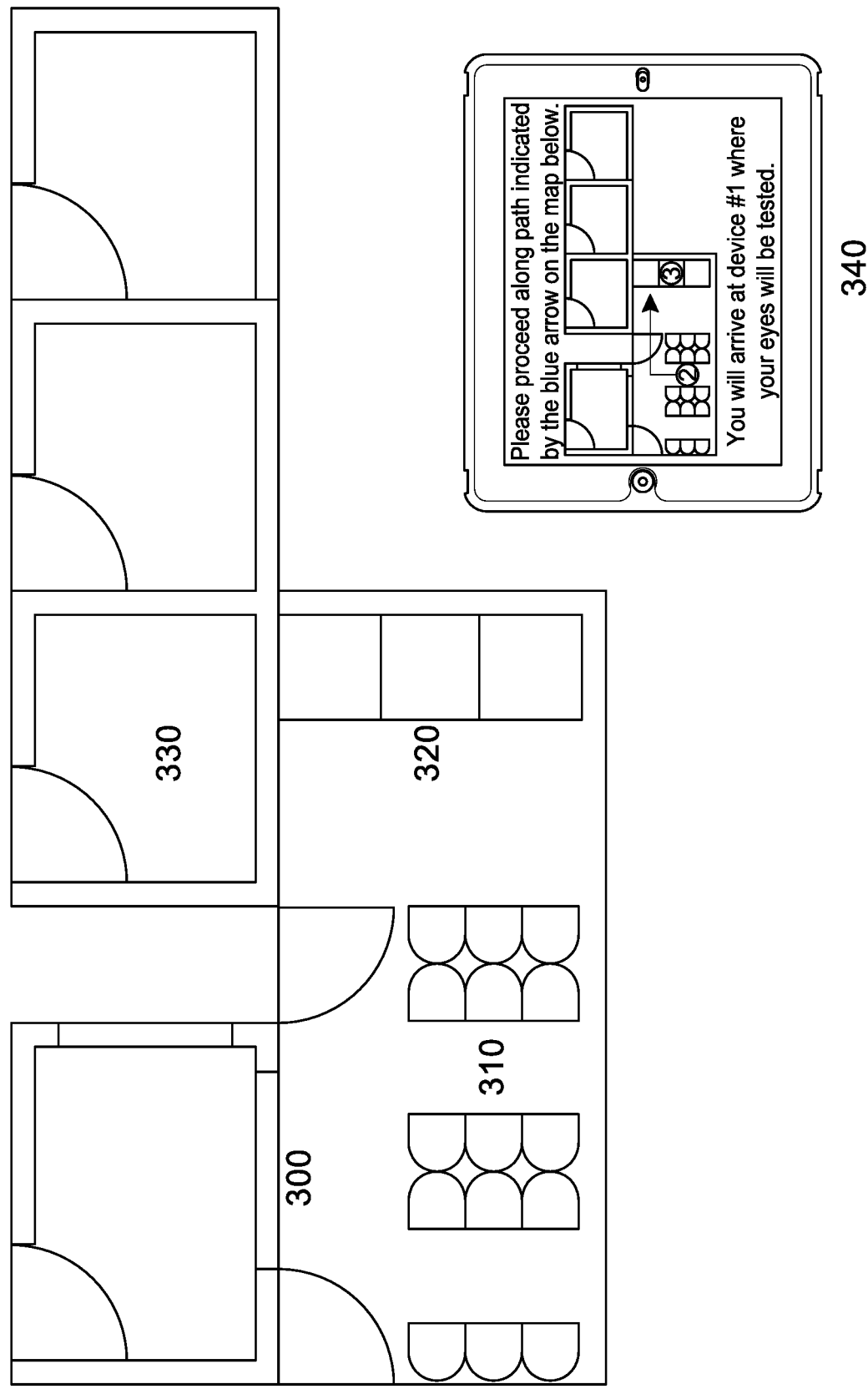
FIG. 10 schematically illustrates a healthcare office map.

Referring to FIG. 10, in one embodiment 340, a line can be drawn on a schematic map of the clinic space on patient interface 250 to show the patient how to walk to their next destination in the clinic. In another embodiment, the patient interface 250 can be configured to communicate directions verbally, such as by text-to-speech software.

In one embodiment, the encounter module 200 may be configured to monitor which rooms and devices in an office are "in use" based on information provided by the tracking system 240. In one embodiment, the encounter module 200 may be configured to select a next location for a patient based on which rooms or devices 260 may be free to use. For example, if the encounter module 200 determines that a device 260 required for the next stage of a clinic process 205 is occupied or busy, the encounter module 200 can be configured to alter the clinic process 205 by inserting, for example, a waiting room order that, for example, can be removed from the clinic process 205 when the required device is free for use.

In one embodiment, the encounter module 200 can be configured to monitor utilization of a device 260 or clinic area that may be required for the next stage of a clinic process 205 and may be configured to insert an order for a patient to move to that device 260 or clinic area when it becomes free for use.

In another embodiment, the encounter module 200 can be configured to monitor the list of patients waiting for a provider and also to determine which providers have the shortest waiting lists or waiting times based on, for example, the number of patients in a waiting patient list and the average time the provider spends with each patient. The encounter module 200 can be configured to use this information, for example, to assign patients to providers with the shortest wait times so as to improve clinic flow. Numerous other embodiments of device decisions based on dynamic knowledge of device and space utilization within an office space are possible.

Figure 11:
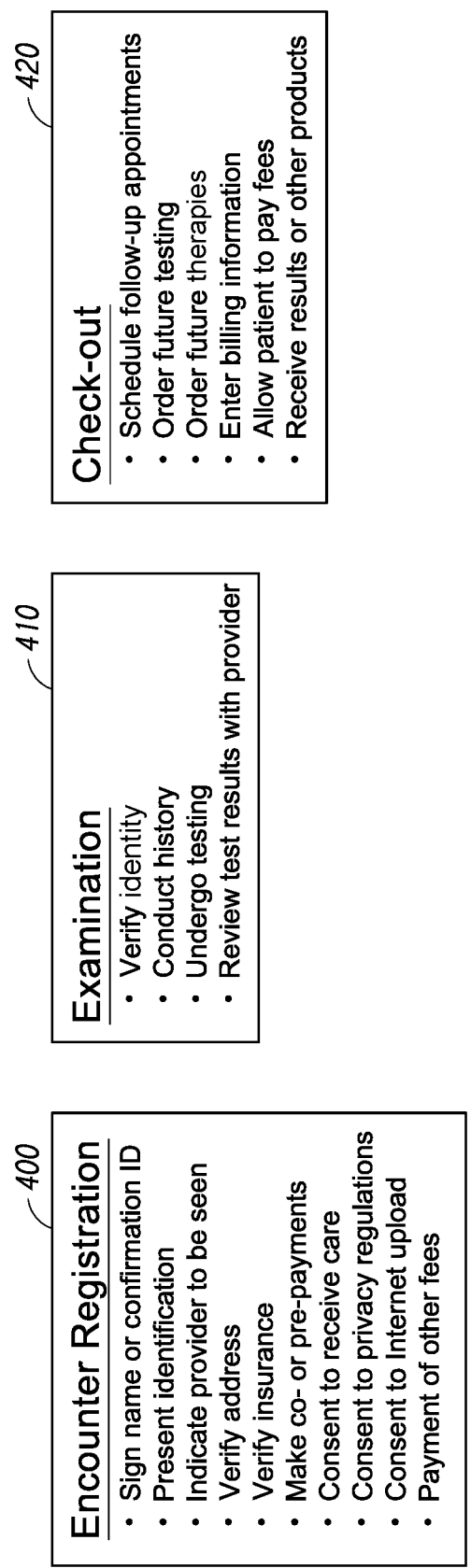
FIG. 11 schematically illustrates a block diagram of a sample healthcare encounter.

An example of a healthcare encounter is shown in FIG. 11. In one embodiment, the first step in the encounter may be registration 400 which can be completed, for example, by office staff or by the patient using, for example, an office interface 210. Encounter registration 400 may be comprised of many steps such as signing the patient's name and address, presenting identification, verifying insurance status, paying co-payments due prior to the encounter, consenting to be seen by the provider, consent to privacy regulations or payment of other fees. In other embodiments, the user may skip registration 400 and may proceed to other steps, such as examination 410.

In one embodiment, one step in an automated healthcare encounter can be verification of the user's identity. This may be accomplished, for example, as part of registration 400, as part of examination 410, prior to using any device 260, or at other times in the encounter. A mobile patient interface 250 may be advantageous since it can verify the user's identity once and then communicate this identity to, for example, the encounter module 200, to providers, or to subsequent devices used throughout the encounter, such as devices 260.

In various embodiments, the patient interface 250 can be configured to verify the user's identity through biometrics, such as through recognition of the patient's face, voice, fingerprint or other unique physical aspects of the subject. In other embodiments, the patient interface 250 can be configured to verify the user's identity through confirmation of a user's unique data, such as their names, date of birth, addresses, mother's maiden name, or answers to questions only known to the user. In another embodiment, the patient interface 250 can be configured to verify the user's identity through confirmation of code, such as a password or secret code known only to the user. In still another embodiment, the patient interface 250 can be configured to verify the user's identity through coupling of a device carried only by the user, such as a key, electronic device, bar code or QR code.

In one embodiment of an electronic healthcare encounter, the user may complete the history portion of their examination as part of their overall encounter. As discussed previously, in various embodiments, the history portion of the encounter can be collected, for example, by office staff or by the patient themselves. Office staff may use the patient interface 250 or the office interface 210 to conduct or enter results from a patient history. In other embodiments, the patient may use the patient interface 250 to complete their own history without interacting with office staff.

In various embodiments, the questions can be configured in a form that facilitates responses using written, mouse-based, tablet-based or voice entry such as multiple choice, true or false, or pull-down menu selections. In other embodiments, the questions may require free entry such as by writing, voice dictation, or keyboard entry. In these examples, the patient interface 250, the office interface 210 or the encounter module 200 may be configured to interpret electronic forms of these inputs, such as electronic writing or voice dictation.

In one embodiment, the history portion of the encounter may be comprised of a standard series of questions. In another embodiment, the series of questions may be based on, for example, a preference specified by the provider, the patient's diagnosis, the patient's symptoms or some other unique aspect of the encounter.

In still another embodiment, the history portion of the encounter can be comprised of questions from a database whereby the next question to be asked can be determined, for example, based on an answer to a previous question. This dynamically-traversed database of questions may use answers from a question to determine subsequent questions to ask or to determine sets of questions to ask based on a tree organization of questions in the database. For example, if a patient reports color vision loss, the system can be configured to add a series of questions related to color vision loss to its list of questions even if they were not previously included in the set of questions to be asked. In later questioning, it the patient reports pain on eye movement, the system can be configured to add, for example, questions related only to pain on eye movement or questions related to pain on eye movement and color vision loss. The dynamic allocation of new questions based on answers to previous questions can be configured such that a provider can allow or disallow such a feature.

In one embodiment, a dynamically-traversed electronic questionnaire can be configured to assign priority values to each question so that certain questions can be asked before other questions. In still another embodiment, the system can provide a running count of the total number of questions to be asked to the patient along with an estimated total time to completion. In related embodiments, the system can be configured to allow users or providers to shorten the questionnaire, such as by excluding lower priority questions, based on aspects of the dynamic questionnaire such as it taking too much time or involving too many questions and answers.

In another embodiment, the patient interface 250 can be configured to allow the user to change display parameters, such as size, color and font type, used to display questions with the patient interface 250. In other embodiments, the patient interface 250 can be configured to read questions aloud, for example using a text-to-speech system or pre-recorded voices, or to ensure privacy by providing a headphone jack where the user can connect headphones.

In one embodiment, the encounter module 200 can be configured to direct devices 260 to perform tests and store results associated with the clinic process 205 and the patient's information contained within the encounter module 200. The encounter module 200 can be configured to communicate with these devices 260 using a direct wired connection, such as a USB, Ethernet or serial connection, a wireless connection, such as Bluetooth® or 802.11, an intermediate electronic device, such as a USB key, memory card or patient interface 250, or a physical coded embodiment such as a bar code or QR code.

In one embodiment, the encounter module 200 or patient interface 250 can be configured to alter the list of tests requested for an encounter based on answers to history questions or results from testing on devices 260. The encounter module 200 or the patient interface 250 can also be configured to direct a device 260 to conduct a new test or tests in addition to or in place of the old test or tests. Alteration of the clinic process 205 by the encounter module 200 or patient interface 250 can be allowed or disallowed by a provider either globally or specifically, such as based on answers to specific questions or categories of questions, using, for example, the office interface 210.

In one embodiment, the encounter module 200 or the patient interface 250 can be configured to initiate operation of a device 260, such as an instrument to measure vision. In another embodiment, the encounter module 200 or the patient interface 250 can be configured to allow the user to initiate operation of a device 260, such as by saying "ready", pushing a button or pressing a pedal that may be attached to the patient interface 250. In still another embodiment, the encounter module 200 or the patient interface can be configured to allow the user to initiate operation of the device 260, such as by saying "ready", pushing a button or pressing a pedal, through the device 260.

As discussed previously, the encounter module 200 or the patient interface 250 can be configured to receive data, such as examination results, from devices, such as the tracking system 240, the patient interface 250 or devices 260. As discussed above, the encounter module 200 can be configured to communicate with these other components using, for example, a wired connection, a wireless connection, an intermediate electronic, or using a physical embodiment.

Collection of data from numerous devices by the patient interface 250 or encounter module 200 can be particularly advantageous by reducing transcription or sorting errors that can occur when human laborers are involved in these processes or by centralizing all encounter data in one location.

Various components in the electronic encounter system, such as the encounter module 200, can be configured to compile encounter data into a digital package or packages that can be uploaded to, for example, an electronic health record system either in the office, such as the office database 220, or outside the office via secure external communication 235, transmitted to other individuals on a patient's health-care team via secure external communication 235, reviewed directly by the provider on a patient interface 250 or office interface 210, or stored on an accessible external database 230. The external database 230 can be configured to be accessible remotely, such as via the Internet, for example, to facilitate sharing of exam data between providers or to facilitate access by the patient to their own healthcare data.

As discussed previously, the encounter module 200 can be configured to track both patients and clinic personnel using the tracking system 240. The encounter module 200 can be configured to store tracking information such that it, for example, can be viewed or analyzed using an office interface 210. By tracking a patient's location over time, the encounter module 200 can be configured to develop clinic patient flow maps that may enable staff to identify both acute and chronic problems with clinic flow. For instance, identification of a patient by the encounter module 200 who has been waiting longer than a pre-defined threshold value stored in a clinic process 205 can alert the staff, for example via an office interface 210, to address problems with that patient's encounter that might be leading to this delay. Identification of chronic bottlenecks and waiting points across numerous encounters can allow practices to optimize their workflow.

Providers can be tracked in several ways. In one embodiment, mobile office interfaces 210 can be configured with tracking systems 240 to identify the location and identity of providers carrying them. In another embodiment, the patient interface 250 can be configured to require providers to log in whenever they are consulting with a patient. In still another embodiment, the tracking system 240 can be configured to monitor the location or identity of providers wearing identifiers, such as RFID tags. In other embodiments, the encounter module 200 could be configured to communicate updates to patients, such as by using the patient interface 250, to, for example, estimate the approximate wait times until the provider sees them or to convey how many patients still need to be seen by the provider before they are seen by the provider.

The electronic encounter portal can also be configured to provide entertainment or education to a patient. For example, the patient interface 250 can be configured to provide Internet access 235, access to previous encounter records stored on the encounter module 200, or access to previous encounter records stored on the external database 230. The patient interface 250 can also be configured to provide access by the patient to educational resources, potentially targeted toward the diagnosis or future treatments for a patient, that may be stored on components such as the encounter module 200. In one embodiment, the provider can use a patient interface 250 or an office interface 210 to enter orders for an educational program into a clinic process 205.

In another embodiment, the patient interface 250 can be used to inform a patient about clinic resources, such as clinical trials, support programs, therapeutic services, restrooms, refreshments, etc. based on information stored on the encounter module 200. The encounter module 200 can also be configured to direct patients to these resources, such as restrooms, based on information from the tracking system 240 and requests from the patients using the patient interface 250. The encounter module 200 can also be configured to manage communications between patients, using a patient interface 250 and office staff, such as by using an office interface 210.

In one embodiment, the patient interface 250 can be configured to store data from devices and, in an embodiment that is mobile such as a tablet or smartphone, can allow the patient to transport encounter data through the clinic process 205 for review by or with the provider. In another embodiment, the office interface 210 can be configured to enable data to be uploaded for review by the provider. Both the patient interface 250 and the office interface 210 can be configured to access and use prior visit data from the encounter module 200 to enhance assessments of a patient's healthcare status. Similarly, both the patient interface 250 and the office interface 210 can be configured to access prior data from the external database 230 to enhance assessments of a patient's healthcare status.

In related embodiments, the encounter module 200 and the external database 230 can be configured to act as common locations for encounter data that can be accessed by both patients and providers. The external database 230 can be configured to allow remote access to encounter data by both providers and patients when they are outside of the office. Similarly, the external database 230 can be configured to receive data from devices 260 at locations outside of the described office and share these results with the encounter module 200 for example, to enable automated remote healthcare encounters.

In one embodiment of an electronic encounter portal, a check-out procedure 420 may be the last order or step in a clinic process 205. In various embodiments, the office interface 210 or the patient interface 250 can be configured to allow providers to enter orders for future encounters such as testing or therapies. In other embodiments, the office interface 210 can be configured to enable the provider to enter billing information to be submitted for insurance reimbursement or directly charged to the patient. In still another embodiment, the office interface 210 can be configured to allow the provider to recommend a follow-up interval for the next encounter. In a related embodiment, the office interface 210 or the patient interface 250 can be configured to allow the patient to select the best time and data for a follow-up encounter. In another embodiment, the office interface 210 can be configured to allow the provider to order educational materials or educational sessions for the patient that may occur after the encounter concludes.

Accordingly, various embodiments described herein can reduce the need for clinic personnel to perform these tasks. In addition, various embodiments enable users to conduct their own complete eye exams.

Automated Eye Examination

Figure 12:
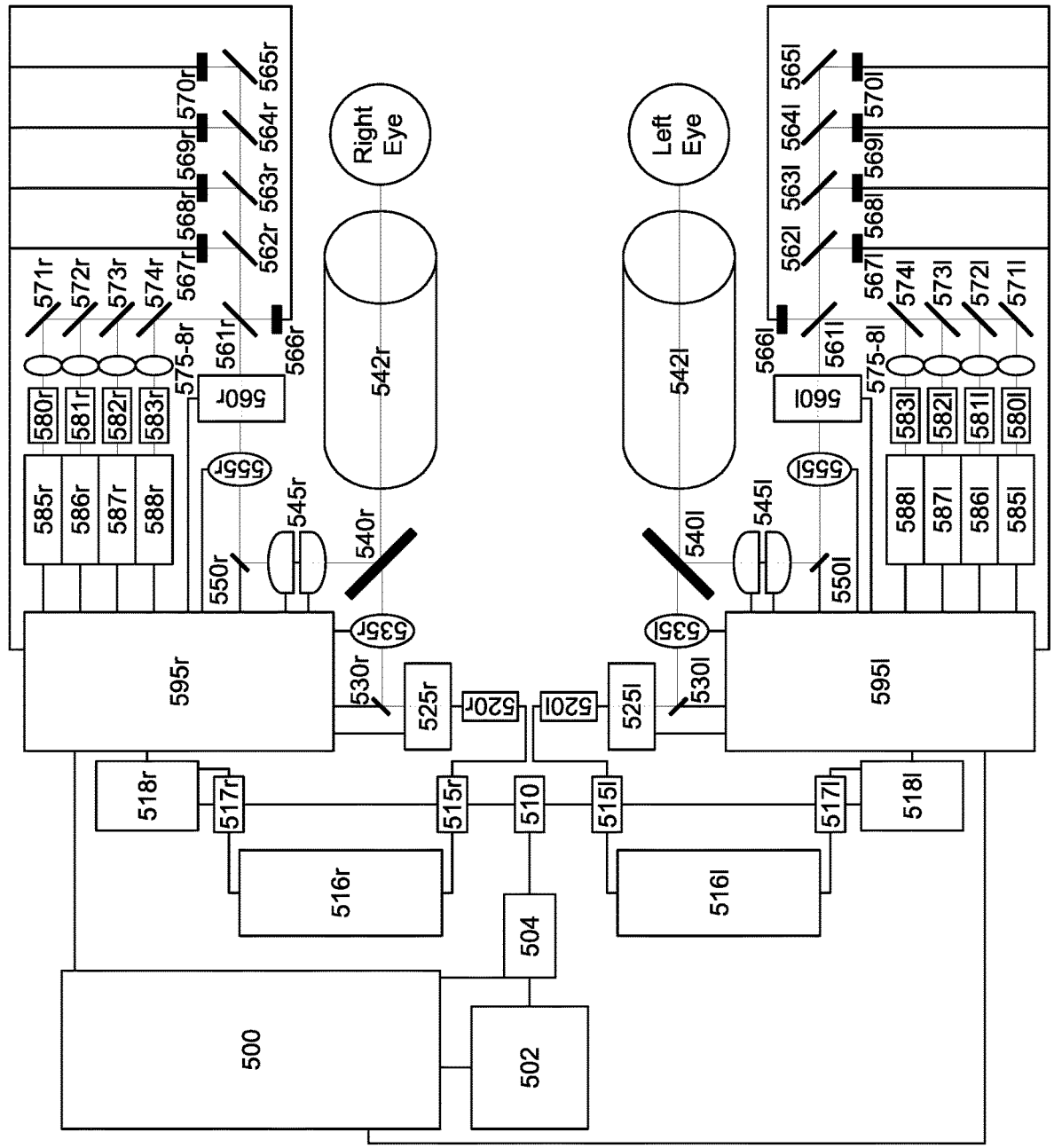
FIG. 12 schematically illustrates a binocular eye examination system based on optical coherence tomography.

FIG. 12 shows an example of a binocular eye examination system based on optical coherence tomography. Component 500 may be comprised of the main electronics, processors, and logic circuits responsible for control, calculations, and decisions for this optical coherence tomography system. Light can be output from light source 502 which may be controlled at least in part by component 500. The light source may be comprised of a broadband light source such as a superluminescent diode or tunable laser system. The center wavelength for light source 502 can be suitable for optical coherence tomography of the eye, such as 840 nm, 1060 nm, or 1310 nm. The light source 502 may be electronically controlled so that it can be turned on, off or variably attenuated at various frequencies, such as 1 Hz, 100 Hz, 1 kHz, 10 kHz or 100 kHz. In one embodiment, light from light source 502 can travel through interferometer 504, which may be comprised of a Mach Zender or other type of interferometer, where a k-clock signal can be generated. This electronic signal can be transmitted to electronics on component 500 or other components in the system and can be captured on a data acquisition system or used as a trigger for data capture.

The k-clock signal can be used as a trigger signal for capturing data from balanced detectors 518r and 518l. Alternatively, the k-clock signal can be captured as a data channel and processed into a signal suitable for OCT data capture. This k-clock signal can be captured all of the time, nearly all of the time or at discrete times after which it would be stored and recalled for use in OCT capture. In some embodiments, various parameters of the k-clock signal, such as frequency or voltage, can be modified electronically, such as doubled or quadrupled, to enable deeper imaging in eye tissues. In various embodiments with light sources that sweep in a substantially linear fashion, the k-clock can be removed and a regular trigger signal may be employed. In various embodiments, the trigger signals used by electronics 595r and 595l may be synchronized with other components of the system, such as mirrors, variable focus lenses, air pumps and valves, pressure sensors and flow sensors.

Most of the light, such as 90% or 95%, that enters the interferometer 504 can be transmitted through interferometer 504 to a beam splitter or coupler 510. As used herein, "coupler" may include splitters as well as couplers. Beam coupler 510 can split the light from interferometer 504 or light source 502 to two output optical paths, specifically right and left, that lead directly to couplers 515r and 515l. Henceforth, designation of a device or component with a suffix of 'r' or 'l' will refer to two devices that may be of the same type but are located in different optical paths. For example, one component may be located in the optical path of the right eye, designated as 'r,' and the other is located in the optical path of the left eye, designated as 'l.'

The optical paths in this system may be comprised of fiber optics, free space optics, a mixture of free space and fiber optics. Other combinations are also possible. The split ratio of coupler 510 can be a predefined ratio, such as 50/50 or 70/30. Light from coupler 510 can travel to couplers 515r and 515l. Couplers 515r and 515l may also split light from coupler 510 with a predefined split ratio such as a 50/50, 70/30, or 90/10. The split ratios for couplers 510, 515r and 515l may be the same or different split ratios.

One portion of light from couplers 515r and 515l, such as 70%, can travel to a so-called 'reference arm' for each of the right and left optical paths. The reference arm of a light path is distinguished from the so-called sample arm of the light path since light in the reference arm of the system does not interface with eye tissue directly whereas light in the sample arm is intended to contact eye tissue directly.

The main component in the reference arm may be an optical delay device, labeled as 516r and 516l in the right and left optical paths of the system. Optical delay devices can introduce a delay, such as 1 picosecond, 10 picoseconds or 100 picoseconds, into a light path to enable matching of the overall path length of one optical path to the optical path length of another light path. In various embodiments, this optical delay may be adjustable, such as with an adjustable free light path between two collimating optical devices, a fiber stretcher that increases or decreases the length of a fiber optic, or a fiber Bragg grating that delays light based on changes in the angle of incidence of light.

In other embodiments, this optical delay line can include variable attenuators to decrease or increase the transmission of light, optical switches or mechanical shutters to turn the light off or on. Although pictured in the reference arm of this system, an optical delay line can also be entirely included in the sample arm optical path for each eye or contained in both the reference and sample arm light paths. Other combinations of sample and reference light paths are also possible.

In one embodiment, light from optical delay devices 516r and 516l can travel to couplers 517r and 517l where it may be combined with light from the sample arm that has been transmitted from couplers 515r and 515l. Couplers 517r and 517*l* may combine light from two light paths with a predefined ratio between paths such as a 50/50, 70/30, or 90/10. Light from couplers 517*r* and 517*l* may travel through two outputs from couplers 517*r* and 517*l* to balanced detectors 518*r* and 518*l* where the light signal can be transformed into an electrical signal, for example through the use of photodiodes configured to detect the light input from couplers 517*r* and 517*l*.

The electrical signal generated by balanced detectors 518*r* and 518*l* can be in various ranges, including but not limited to −400 mV to +400 mV, −1V to +1V, −4V to +4V and have various bandwidths, including but not limited to 70 MHz, 250 MHz, 1.5 GHz. The electrical signal from balanced detectors 518*r* and 518*l* may travel via an electrical connection, such as a coaxial cable, to electronics 595*r* and 595*l* where it can be captured by a data acquisition system configured to capture data from balanced detector devices. Although not pictured here, a polarization sensitive optical component can be disposed before balanced detectors 518*r* and 518*l* to split two polarities of light in a single light path into two optical paths. In this embodiment, two optical paths leading to balanced detectors 517*r* and 517*l* would be split into a total of four optical paths which would lead to two balanced detectors on each side.

One portion of light from couplers 515*r* and 515*l*, such as 30% or 50%, can travel to a so-called sample arm of each of the right and left optical paths. In various embodiments, the system may be configured to transmit the light through fiber optic cable or through free space optics. Light from couplers 515*r* and 515*l* can travel to optics 520*r* and 520*l* which may be collimators configured to collimate the light from couplers 515*r* and 515*l*. Light from optics 520*r* and 520*l* can travel to lens systems 525*r* and 525*l* which may be comprised of fixed focus or variable focus lenses.

In various embodiments, these lenses can be fabricated from plastic or glass. In other embodiments, these lenses may be electrowetting lenses or shape-changing lenses, such as fluid-filled lenses, that can vary their focal distance based on internal or external control mechanisms. In one embodiment, variable focus lenses in lens systems 525*r* or 525*l* may have their focal length modified by electrical current or voltage applied to lens systems 525*r* or 525*l*. This control may come from electrical components 595*r* and 595*l* and the parameters of this control may be based on pre-determined values or may be derived during operation of the system based on input received from other components of the system.

The lenses in lens systems 525*r* and 525*l* can be configured to have anti-reflective coatings, embedded temperature sensors, or other associated circuitry. Lens systems 525*r* and 525*l* may be comprised of a single lens or multiple lenses. The lenses comprising systems 525*r* and 525*l* may be present at all times or may be mechanically moved in and out of the light path such as by an attached motor and drive circuit under electrical control from components 595*r* and 595*l*. Configuration of lens systems 525*r* and 525*l* to be moveable can enable imaging at different depths in an eye tissue by introducing and removing vergence in the optical system.

Light from lens systems 525*r* and 525*l* can travel to movable mirrors 530*r* and 530*l*. Movable mirrors 530*r* and 530*l* may be comprised of MEMS (microelectromechanical systems) mirrors, controlled by galvanometers, or moved by other means. Movable mirrors 530*r* and 530*l* can be comprised of a single mirror that reflects light across 2 axes, such as X and Y, can be comprised of a single mirror that reflects light across one axis only, or can be comprised of two mirrors that each reflect light across one axis only said axes being substantially perpendicular to each other.

Electrical control of mirrors 530*r* and 530*l*, which may control each axis of reflection independently, can be provided by components 595*r* and 595*l*. The electronic control of mirrors 530*r* and 530*l* may be configured to enable variable amplitude deflections of mirrors 530*r* and 530*l*. For example, for a given drive frequency in a given axis, the current or voltage applied to mirrors 530*r* and 530*l* may enable larger or smaller amplitude deflections of the mirror surface, thus creating a zoom effect where the created image can be made smaller or larger.

Light that has been reflected from movable mirrors 530*r* and 530*l* can travel to lens systems 535*r* and 535*l*. Lens systems 535*r* and 535*l* may be fixed or variable focus lenses that are located in the optical light path at all times or only part of the time. Electrical control of lenses 535*r* and 535*l*, can be conducted by components 595*r* and 595*l* and may include for example moving these lenses in and out of the light path or changing their focal lengths. Other actions are also possible.

Light from lens systems 535*r* and 535*l* can travel to optics 540*r* and 540*l* which may be comprised of dichroic mirrors or couplers. Optics 540*r* and 540*l* may be configured to transmit light from lens systems 535*r* and 535*l* and combine it with light from lens systems 545*r* and 545*l*. Light from optics 540*r* and 540*l* can travel to eye pieces 542*r* and 542*l* before being transmitted to the right and left eye tissues.

Eye pieces (or oculars) 542*r* and 542*l* can be configured as multi-element lens systems such as Ploessel-type eyepieces, Erfle-type eyepieces, telescopes or other designs. In some embodiments, optics 540*r* and 540*l* may be configured to be part of or inside of eyepieces 542*r* and 542*l*. In other embodiments, variable focus lenses or polarization-sensitive optics and beam splitters can be configured inside eyepieces 542*r* and 542*l* to enable wider axial focusing ranges in eye tissues or simultaneous focusing of light from two axial locations in eye tissues. Eyepieces 542*r* and 542*l* may be configured with optical components without any refractive power, such as optical windows, that may be physically attached or separate from the other lenses in the system.

Light entering the right and left eyes can be reflected back through each optical path to enable optical coherence tomography. In one embodiment, the path of backreflected light originating from light source 502 can travel from each eye to eyepiece 542 to optics 540 to lens system 535 to movable mirror 530 to lens system 525 to optics 520 to coupler 515 to coupler 517 to balanced detector 518. Various calculations and logic-based processes can be completed by components 595*r* and 595*l* based on data contained in signals received from balanced detectors 518*r* and 518*l*.

As discussed previously, timing of capture of the signals received by components 595*r* and 595*l* may be controlled by other inputs, such as the k-clock input, dummy clock input, or other electrical signal. Electronics 500, 595*r*, and 595*l* may be configured to have digital signal processors (DSPs), field-programmable gate arrays (FPGAs), ASICs or other electronics to enable faster, more efficient or substantially real-time processing of signals received by components 595*r* and 595*l*. Electronics 500, 595*r*, and 595*l* may be configured with software, such as a real-time operating system, to enable rapid decisions to be made by said components.

In various embodiments not illustrated here, the eye tissues may be replaced by calibration targets that, for example, occlude the eyepieces, dispose a mirror target at various distances in front of the eyepieces, or provide an open air space for calibration. Electronics 500 may be configured to control the introduction of these non-tissue targets, such as when the eyes are not present in the optical system. In other embodiments, electronics 500 may be configured to dispose powered or moveable components of the system to various states, such as "off," "home," or "safety" at various times, such as the beginning, middle and end of a test.

Components 595r and 595l can also be configured to control light sources 585r-588r and 585l-588l which may be comprised of various light sources such as for example, laser diodes, light emitting diodes, or superluminescent diodes. In the illustrated embodiment, only four light sources 585r-588r and 585l-588l are shown. In various embodiments, different numbers of light sources 585r-588r and 585l-588l may be used and different wavelengths of light sources may be used. In one embodiment, one each of a blue-colored, green-colored, red-colored and near infrared diode can be included in the light source groups 585r-588r and 585l-588l.

In other embodiments, light sources 585r-588r and 585l-588l may be comprised of tunable light sources capable of producing numerous spectra of light for the purposes of hyperspectral imaging. For example, employing various light sources in the visible spectrum capable of producing narrow bands of light centered at characteristic peaks of absorption or reflectivity for oxyhemoglobin and deoxyhemoglobin can be used to enable hyperspectral imaging. Similarly, numerous individual light sources can be used to achieve the same effect as a light source with a tunable wavelength.

These light sources can be configured to be controlled by components 595r and 595l using, for example, pulse-width modulation, current modulation, voltage modulation, or other electrical control means. In one embodiment, the modulation frequency of at least one light source can be modified to correct for chromatic aberration from the optics between the light sources and the eye. For example, the modulation frequency of the red channel could be variably increased or decreased in different mirror positions to account for lateral chromatic spread between the red light source and other colors such as blue or green.

Light from light sources 585r-588r and 585l-588l can travel to optics 580r-583r and 580l-583l which may, for example, be focusing optics. Light from optics 580r-583r and 580l-583l can then travel to optics 575r-578r and 575l-578l which may, for example, be focusing optics. Each path of light can contain a single frequency of light, such as 450 nm, 515 nm, 532 nm, 630 nm, 840 nm, or 930 nm or multiple frequencies of light.

Each path of light from light sources 585r-588r and 585l-588l may be reflected off optics 571r-574r and 571l-574l which may, for example, be dichroic mirrors or couplers and may be specifically configured to reflect and transmit light based on their position in the optical path. For example, one optic may be configured to transmit light with a wavelength less than 500 nm and reflect light with a wavelength greater than 500 nm.

Optics 571r-574r and 571l-574l can be configured to join together light from different light sources 585r-588r and 585l-588l into a single, substantially coaxial beam of light that can travel to optics 561r and 561l. Optics 561r and 561l may be dichroic mirrors or couplers and may be configured to have a pre-defined split ratio of light entering from different directions or having different wavelengths, such as 90/10, 50/50, and 10/90.

A portion of light from optics 571r-574r and 571l-574l can be transmitted through optics 561r and 561l to sensors 566r and 566l which may, for example, be photodiodes or other components capable of sensing light. Signals from sensors 566r and 566l can be configured to be transmitted along electrical connections between sensor 566r and electrical component 595r on the right side and sensor 566l and electrical component 595l on the left side. In one embodiment, sensors 566r and 566l can be configured to monitor the total light power being emitted by light sources 585r-588r and 585l-588l.

The portion of light reflected off optics 561r and 561l from optics 571r-574 and 571l-574l can travel to lens systems 560r and 560l. Lens systems 560r and 560l may be comprised of fixed focus or variable focus lenses. In various embodiments, these lenses can be fabricated from plastic or glass. In other embodiments, these lenses may be electrowetting lenses or shape-changing lenses, such as fluid-filled lenses, that may vary their focal distance based on internal or external control mechanisms.

In one embodiment, variable focus lenses in lens systems 560r and 560l may have their focal length modified by electrical current or voltage applied to the lens systems. This control may be under the direction of electrical components 595r and 595l and it may be based on pre-determined values or be derived during operation of the system based on input received from other components of the system.

The lenses in lens systems 560r and 560l can be configured to have anti-reflective coatings, embedded temperature sensors, or other associated circuitry. Lens systems 560r and 560l may be comprised of a single lens or multiple lenses. The lenses comprising systems 560r and 560l may be present in the light path at all times or may be mechanically moved in and out of the light path by an attached motor and drive circuit under electrical control from components 595r and 595l. Configuration of lens systems 560r and 560 to be moveable can enable imaging at different depths in an eye tissue by introducing and removing vergence in the optical system.

Light from lens systems 560r and 560l can travel to lens systems 555r and 555l. In some embodiments, lens systems 555r and 555l can be located in their respective optical paths at all times. In other embodiments, lens systems 555r and 551 may be moved in and out of the optical paths based on electrical signals from components 595r and 595l.

Light from lens systems 555r and 555l can travel to movable mirrors 550r and 550l. Movable mirrors 550r and 550l may be comprised of MEMS mirrors, controlled by galvanometers, or moved by other means. Movable mirrors 550r and 550l can be comprised of a single mirror that reflects light across 2 axes, such as X and Y, can be comprised of a single mirror that reflects light across one axis only, or can be comprised of two mirrors that each reflect light across one axis only said axes being substantially perpendicular to each other.

Electrical control of mirrors 550r and 550l, which can control each axis of reflection independently, can be provided by components 595r and 595l. Mirrors 550r and 550l may have one axis of fast resonant movement, one axis of slow resonant movement, two slow axes of movement, one fast resonant axis and one slow axis of movement, or two fast resonant axes of movement.

The electronic control of mirrors 530r and 530l may be configured to enable variable amplitude deflections of mirrors 530r and 530l. For example, for a given drive frequency in a given axis, the current or voltage applied to mirrors 530r and 530l may enable larger or smaller amplitude deflections of the mirror surface, thus creating a zoom effect where the created image can be made smaller or larger.

Light from movable mirrors 550r and 550l can travel to lens systems 545r and 545l. Lens systems 545r and 545l may be configured to introduce variable amounts of optical cylinder power into the optical light paths. In one embodiment, the magnitude and axis of the cylindrical optical power introduced into the optical paths by lens systems 545r and 545l can be configured to correct an astigmatism present in an eye interfacing with this system.

Lens systems 545r and 545l can comprised of two cylindrical lenses configured to counter-rotate and co-rotate with each other, an electrically controlled variable focus, liquid filled lens, or other method of introducing cylindrical optical power into a light path. Although not illustrated here, lens systems 545r and 545l can also be located between mirrors 530r and 530l and optics 540r and 540l in the OCT light path.

Light from lens systems 545r and 545l can travel to optics 540r and 540l where it may be reflected to combine with light originating at light source 502. In one embodiment, an exit pupil expander can be disposed between moveable mirrors 550r and 550l and the eye tissues to increase the size of the exit pupil created at the eye tissue by mirrors 550r and 550l.

Light from lens systems 545r and 545l may be transmitted through eyepieces 542r and 542l after which it may enter the right and left eyes of a subject. Light transmitted through eyepieces 542r and 542l can be configured to be seen by the subject as organized light, such as in a retinal scanning display system, can be configured to be seen by the subject as video-rate imaging through modulation of light sources 585r-588r and 585l-588l by components 595r and 595l, or can be configured to broadly stimulate the eye with light such as for measurements of pupillary reactions to light stimuli.

Light from lens systems 545r and 545l can also be configured to reflect back out of the eye and through eyepieces 542r and 542l, off optics 540r and 540l, through lenses systems 545r and 545l, off moveable mirrors 550r and 550l, through lens systems 555r, 555l, 560r, and 560l and then through optics 561r and 561l. Light transmitted through optics 561r and 561l can be detected by sensors 567r-570r and 567l-570l which may, for example, be comprised of photodiodes.

In various embodiments, this light is split into predefined wavelength bands, such as 440 nm-460 nm, 510 nm-580 nm, 625 nm-635 nm, or 930 nm, by dichroic mirrors 562r-565r and 562l-565l. In other embodiments, separation of light from optics 561r and 561l into bands can be achieved by the use of filters that selectively transmit or reflect wavelength bands of interest.

In still other embodiments, separation of light from optics 561r and 561l into bands can be achieved by configuring the system with sensors 567r-570r and 567l-570l that only produce electrical signals in specifically targeted bands, such as 400-500 nm, 600-800 nm or >900 nm. Electrical signals from sensors 567r-570r and 567l-570l can travel to components 595r and 595l across electrical connections to enable imaging of tissues in the eye by sensing the light originating at light sources 585r-588r and 585l-588l back-reflected in desired wavelength bands.

Figure 13:
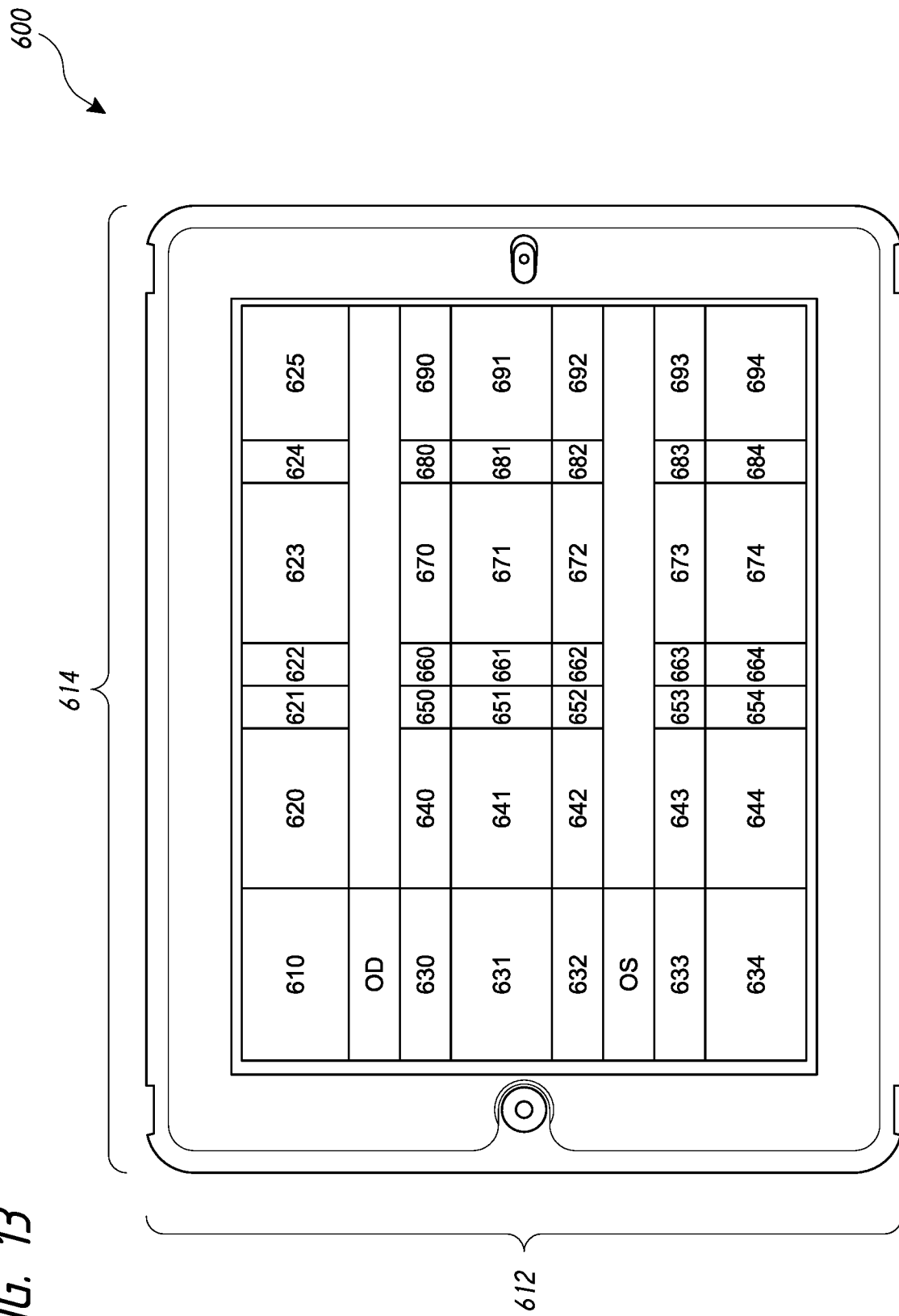
FIG. 13 schematically illustrates a display of eye examination data.

FIG. 13 shows an example of a display of eye examination data on an electronic device 600. In some embodiments, the display system enables viewing and comparing of data from two eyes of one patient across multiple tests and dates in a minimal amount of space. Accordingly, some embodiments enable the user to collapse undesirable test or date fields so as to maximize the display area of desired measurements.

Device 600 may be a portable computing platform, such as a smartphone or a tablet, or be a stationary computing platform with a display screen. Device 600 may allow touch screen operation, eye tracking operation where eye movements are interpreted as cursor movements on the device 600 itself or operation with standard computing peripherals such as a mouse and keyboard.

Data in the illustrated grid can be populated by software from a database of examination data that may, for example, include exams from many patients on many days. Accordingly, software running on device 600 can be configured to enable searching or selection of the patient whose exam data is to be displayed in the illustrated display configuration.

Software on device 600 can be configured to output exam data in a substantially tabular format comprised mainly of rows 612 and columns 614. In various embodiments, the software can be configured to include all exam data for a given date in one column 614 while all measurements from a given test can be included in a single row 612. The software can also enable preferences that allow transformation of this rule such that dates are in rows 612 and tests are in columns 614. In some embodiments, each box in the table representing an intersection of a row 612 and a column 614 can be represented as a field populated with, for example, a numerical measurement, a text value or an image. Although the fields are labeled generically in FIG. 6, it will be appreciated that a variety of data, such as numbers, text or images, can be displayed in each field.

Field 610 can be configured to contain information on the patient, such as name, date of birth, medical record number, age, gender. Although not illustrated here, field 610 may also be used to open pop-up windows that can be used to search or configure the exam display system.

Fields 620-625 can be configured to contain dates of exams for a given patient. In one embodiment, clicking of a column heading 620-625 toggles the column between collapsed and expanded configurations where data is not displayed in the collapsed configuration but data is displayed in the expanded configuration. In FIG. 6, columns 620, 623 and 625 demonstrate expanded fields while columns 621, 622 and 624 represent collapsed fields. Thus, the fields in the collapsed columns 621, 622, 624 may be collapsed. For example, fields 650, 651, 652, 653, 654 may be collapsed when column 621 is collapsed. The software can be configured to allow users to toggle this display setting with, for example, a simple click of a column heading or other selection process.

Fields 630-634 can be configured to contain individual tests conducted on a given patient. In one embodiment, clicking of a row heading 630-634 toggles the row between collapsed and expanded configurations where data is not displayed in the collapsed configuration but data is displayed in the expanded configuration. In FIG. 6, rows 63l and 634 demonstrate expanded fields while rows 630, 632 and 633 represent collapsed fields. Thus, the fields in the collapsed rows 630, 632, 633 may be collapsed. For example, fields 640, 650, 660, 670, 680, and 690 may be collapsed when row 630 is collapsed. The software can be configured to allow users to toggle this display setting with, for example, a simple click of a row heading or other selection process.

In FIG. 13, it can be appreciated that two special rows can exist corresponding to the right (OD) and left (OS) eye headings. The software can be configured to collapse or expand all tests for a given eye when that row heading, such as OD or OS, is clicked or otherwise selected.

Referring to FIG. 13, fields 641, 644, 671, 674, 691, and 694 can be configured to display data, such as numbers, text or images. In one embodiment, display of images in these fields enables the user to click on the images to bring up a larger window in which to view the images. In another embodiment, display of numbers in these fields enables the user to click on the numbers to bring up a graph of the numbers, such as graph over time with the dates in the column headers as the x-axis and the values in the rows as the y values.

The software can be configured to show collapsed fields (e.g. field 640, 650, 660, 651, 661) in a different color or in a different size. The software can also be configured to display scroll bars when fields extend off the display screen. For example, if more tests exist in the vertical direction than can be displayed on a single screen, the software can be configured to allow panning with finger movements or scrolling with, for example, vertical scroll bars. The software can be configured to enable similar capabilities in the horizontal direction as well.

As described above, in some embodiments, a mask 100 is configured to be interfaced with an ophthalmic device for performing an eye exam on a patient. In some embodiments, the ophthalmic device comprises an optical coherence tomography (OCT) device such as described above. An OCT device is operable to direct an incident light beam onto a patient's eye and receive a reflected or scattered light beam from the patient's retina. Three-dimensional images of eye tissue, such as the cornea, iris, lens, vitreous or retina may be obtained by measuring reflected or scattered light from the tissue for example using Optical Coherence Tomography or other instruments. Many OCT devices employ beam-steering mirrors, such as mirror galvanometers or MEMS mirrors, to direct the light beam to an object of interest. Various OCT instruments comprise interferometers including light sources and optical detectors or sensors that receive light reflected or scattered from the eye and produce a signal useful for imaging the eye. One example of an OCT device is described above with reference to FIG. 12.

When the mask 100 is interfaced with an OCT device for performing an eye exam, an incident light beam is transmitted through at least one of the optically transparent sections 124 of the mask 100 before impinging on the retina of the eye. A portion of the incident light beam may be reflected by the optically transparent sections 124 of the mask. Such reflection is undesirable as it decreases the amount of light transmitted to the retina of the eye and the reflected portion of the incident light beam may also reach the OCT device (e.g., the optical detector 518 therein) and may obscure the signal of interest, namely the reflected or scattered light from the retina. In some embodiments, to ameliorate this problem, the optically transparent sections 124 of the mask 100 are coated with an anti-reflective coating configured to reduce reflection of the incident light beam by the optically transparent sections 124. In various embodiments, the optical transparent sections 124 of the mask are configured to increase or maximize transmission of light, such as from an OCT device, and the proximal portions 154 and concaved rear surface 122 is configured to reduce or minimize transmission of light, such as ambient light or light not emanating from an OCT machine and may be opaque and include opaque sides. For example, the proximal portions 154 may have sides that are substantially non-transmissive to visible wavelengths. These sides may for example block 80-90%, 90-95%, 95-99%, and/or 99-100% of ambient visible light. Reduction of ambient light may for example assist in keeping the patients pupils dilated. Conversely, the optically transparent sections may have a transmittance of 70-80%, 80-90%, 90-95%, 95-99%, and/or 99-99.5%, or 99.5%-100% or any combination of these ranges in the wavelength range at which the ophthalmic device operates such as at 450 nm, 515 nm, 532 nm, 630 nm, 840 nm, 930 nm, 1060 nm, 1310 nm or any combination thereof or across the visible wavelength range, near IR wavelength range, or both these ranges or at least 10%, 20%, 30%, 40%, 50%, 60%, 70%, 80%, or 90% of the visible range, near IR range, or both. In some embodiments, material (treated or untreated) such as plastic that is not substantially transparent to visible light or to many visible wavelengths but is transparent to infrared light may be employed, for example, as the window to the mask and possibly for at least part of the proximal portion (e.g., the sides). The window would thus potentially be able to transmit an IR probe beam from the ophthalmic device (e.g., OCT or SLO instrument) yet could block ambient visible light or a significant portion thereof thereby allowing the user's pupils when wearing the mask to be more dilated. In various embodiments, however, having a window having at least some wavelengths in the visible be transmitted through is useful for the wearer. In certain embodiments, the ophthalmic device operates at one or more near infrared wavelength. For example, the probe beam is in the near infrared. The window may therefore be transparent in at least at the NIR wavelength(s) at which the ophthalmic device operate, for example, at the probe wavelength. Optical coatings may be employed to impart these spectral characteristics on the mask (e.g., on the window).

In some embodiments, the anti-reflective coating is configured to reduce reflection of the incident light beam in a wavelength range that is comparable to the wavelength range of the light source used in the OCT device. For example, wide-spectrum sources such as superluminescent diodes, ultrashort pulsed lasers, swept source lasers, very short external cavity lasers, vertical cavity surface emitting lasers, and supercontinuum lasers can be used in OCT devices and could be used in other ophthalmic diagnostic and/or treatment devices. These light sources may operate in the visible and/or near infrared. For example, light sources that emit light in visible wavelengths such as blue, green, red, near infrared or 400-1500 nm may be used to image the eye. Accordingly, in some embodiments, the anti-reflective coating is configured to reduce reflection of the incident light beam in a wavelength range that is comparable to a visible spectrum. In some embodiments, the anti-reflective coating spans both a visible and invisible wavelength spectrum, operating at wavelengths such as 400 nm to 1500 nm, 450 nm to 1150 nm, 515 nm to 1100 nm or other regions. The anti-reflective coating may be strongly wavelength dependent or may be largely wavelength independent. Likewise, the anti-reflective coating may reduce reflection over a wide or narrow band. In some embodiments, the anti-reflective coating is configured to reduce reflection of the incident light beam in a wavelength band having a bandwidth ranging from about 5 nm to about 200 nm. In some embodiments, for example, this bandwidth may be between about 5 and 50 nm, 50 and 100 nm, 100 and 150 nm, 150 and 200 nm, 200 and 250 nm or larger. In some embodiments, the AR coating may operate across multiple bands that are separated from each other. Each of these bands may, for example, have a bandwidth, for example, as described above. The antireflective coating may reduce reflections at a normal incident angle to between about 5-10%, 3-5%, 1-3% or less. For example, with the anti-reflective coating, reflections at a normal incident angle may be reduced to 1 to 2% reflection, 0.5% to 1% reflection or 0.1% to 0.5% reflection, or 0.05% to 0.5% reflection, or 0.1% to 0.5% reflection, 0.1% to 0.01% reflection, or combinations thereof. In some embodiments, the amount of reflection may be higher or lower. In various embodiments, the anti-reflective coating operates on light from normal incidence up to oblique angles of incidence such as ±15 degrees, ±30 degrees or ±45 degrees.

The anti-reflective coating may comprise a multi-stack optical structure and, in particular, may comprise an interference coating such as a quarter-wave stack. The anti-reflective coating may comprise, for example, one or more layers having a thickness of a quarter or half wavelength of the light and accomplish reflection reduction through destructive interference. Other types of anti-reflection coatings may be employed.

FIGS. 14A-14D a mask 200 for performing an eye exam according to an embodiment. The mask 200 includes a distal sheet member (distal portion) 218 and a proximal member (proximal portion) 254 coupled to the distal portion 218. The distal portion 218 has one or more substantially optically transparent sections 224. The proximal portion 254 has a rear surface 222 that faces the patient's face when in use, and is configured to conform to contours of the patient's face and align the one or more substantially optically transparent sections 224 of the distal portion 218 with the patient's eyes. The distal portion 218 can be configured to be optically interfaced with a docking portion of an ophthalmic device such as an OCT instrument. The ophthalmic device is operable to direct an incident light beam such as a probe beam onto and/or into a patient's eye and receive a reflected or scattered light beam from the patient's eye. The docking portion of the ophthalmic device includes an optical interface such an optically transparent window or plate for transmitting the incident light beam therethrough and incident on the optically transparent sections 224 of the distal portion 218. The docking portion may also include a slot in which a flange on the mask fits into. In some embodiments, the ophthalmic device comprises an optical coherence tomography device although the ophthalmic device may comprise other diagnostic instruments or devices such as a scanning laser ophthalmoscope (SLO).

In some embodiments, to reduce retro-reflection back into the ophthalmic device, at least one of the optically transparent sections 224 of the mask has at least a portion thereof that is tilted or sloped with respect to the incident light beam when the distal sheet member 218 is optically interfaced with the docking portion of the ophthalmic device. In such embodiments the incident light beam forms a finite (non-zero) angle of incidence with respect to the corresponding portion of the mask. If the finite angle of incidence is sufficiently large, a retro-reflected light beam may be prevented from being retro-reflected back into the oculars of the ophthalmic device. In some embodiments, the magnitude of the tilt or slope angle is in a range from about 1 degree to about 30 degrees. In some embodiments, the magnitude of the tilt or slope angle is greater than about 1 degrees, 2 degrees, 4 degrees, 5 degrees, 6 degrees, 8 degrees, 10 degrees, 15 degrees, 20 degrees, 25 degrees, 30 degrees, 35 degrees, 40 degrees, 45 degrees, 50 degrees, or 55 degrees, and less than 60 degrees, 55 degrees, 50 degrees, 45 degrees, 40 degrees, 35 degrees, 30 degrees, 25 degrees, 20 degrees, 15 degrees, 10 degrees, or 5 degrees or any combination thereof. For example, the magnitude of the slope may be greater in magnitude than 30° and less than 35° or greater than 1° in certain portions and less than 35° or 40°. This tilt or slope angle may be measured between a central axis through the optical path from the ophthalmic device (e.g., OCT instrument) to the mask and the normal to the surface of the optically transparent section 224 of the mask where that central axis or probe beam is incident. In some embodiments, this angle may be measured, for example, with respect to the optical path from the ophthalmic device (e.g., OCT or SLO instrument) or optical axis of the ophthalmic devices, for example, from the exit pupil of left or right channel of the OCT or SLO instrument, an optical axis of an optical element (e.g., left and/or right ocular lens, eyepiece, or channel) associated with an ophthalmic device through which the beam passes prior to output from the ophthalmic devices, as well as from a normal to a transparent interface (e.g., a window or ocular lens) on the ophthalmic device. Also this angle may be measured with respect to the normal to the surface on the optically transparent section 224 of the mask where the beam or center thereof or central axis therethrough from the ophthalmic instrument would be incident on the optically transparent section 224. Similarly, this angle may be measured with respect to the mask's forward line of sight when worn or the line of sight of a wearer of the mask. A standard anatomical headform such as an Alderson headform may be used to determine the line-of-sight through the mask. Accordingly, the angular ranges described above may be measured between the line-of-sight of a Alderson headform when the mask is placed on the headform as would be worn by a wearer (in the as worn position) and the normal to the surface of the optically transparent section 224 of the mask at the location that the normal line-of-sight of the headform intersects or passes. Other approaches to measuring the angle may also be used.

In various embodiments, the shape of the rear surface 222 is determined from measurements taken from at least one magnetic resonance imaging (MRI) scan of a human head. Segmentation of the surface of one or more faces (e.g., at least 10, 20, 30, 100, to 200, 500, 1000, or more faces) obtained from MRI images can be used to determine a contour that is substantially conformed to by the rear surface 222. Statistical processes can be applied to these sets of MRI images to produce average face contours, median face contours, or face contours that match a certain percentage of the population, such as 95%, 99%, or 99.5%. These MRI images can also be used to define the line-of-sight through the mask. Standard lines defined by MRI images of the human head, such as the eye-ear line extending from the center of the ear canal to the lateral canthus where the eyelids join or a line in the Frankfurt plane extending from the center of the ear to the lowest portion of the eye socket, can be used to define the direction of the line-of-sight through the mask with a rear surface 222 defined by these same MRI images. Other lines, such as a line that connects the pupillary center and macular center as seen by MRI could also be used. The placement of the line-of-sight on the optical transparent section 224 may also be defined by measuring the distance between the pupils, the interpupillary distance (IPD), on the MRI images.

Figure 15A:
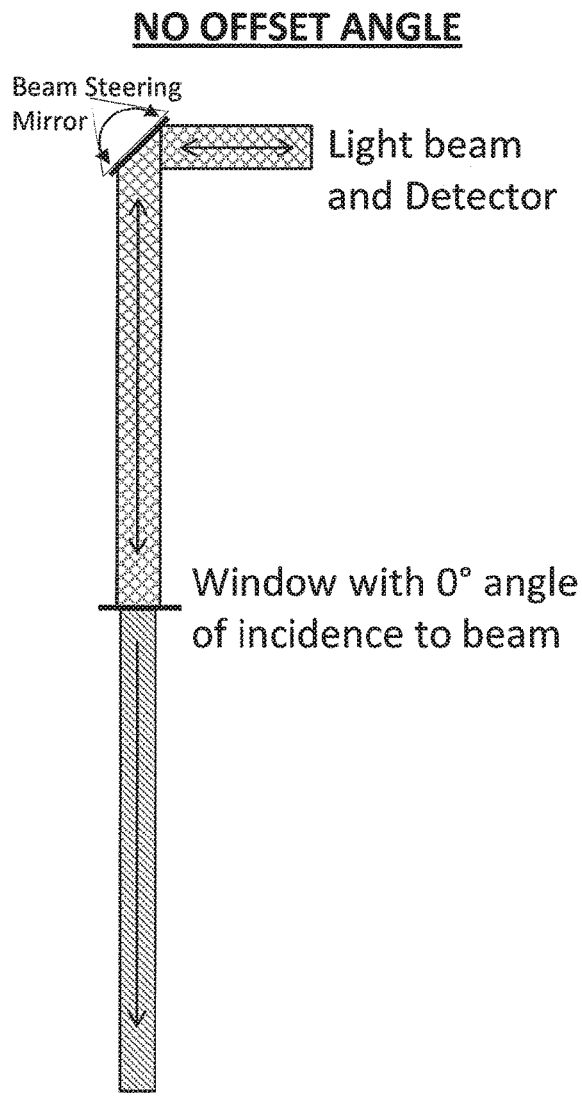
FIGS. 15A and 15B schematically illustrate the effect of a tilted or sloped window on a probe beam from the OCT instrument which reduces retro-reflection into the optical coherence tomography instrument.

In various embodiments, the probe beam raster scanned across the tissue to obtain OCT signals over a region of the eye. As described above, to accomplish such raster scanning, the direction of the probe beam may be swept using, for example, a MEMS mirror. FIG. 15A illustrate an arrangement where a probe beam is reflected off a beam steering mirror through the mask window into the eye. The beam steering mirror can be rotate back an forth to sweep the beam through a range of angles and through a range of positions in and/or on the tissue being images or evaluated. FIG. 15A show both the optical path of the probe beam as well for light scattered from the tissue that returns back through the OCT instrument. As discussed above, in some instances, reflections from the mask window are retro-reflected and thus also return to the sensors used in the OCT instrument. With the normal to the window oriented at 0° with respect to the incident probe beam, light is reflected from the window back into the OCT instrument as shown in FIG. 15A. This retro-reflected light introduces noise into the signal comprising scatters light from the tissue which could be a weak signal. The back reflection thus decreases the signal to noise ratio and makes obtaining an image more difficult.

Figure 15B:
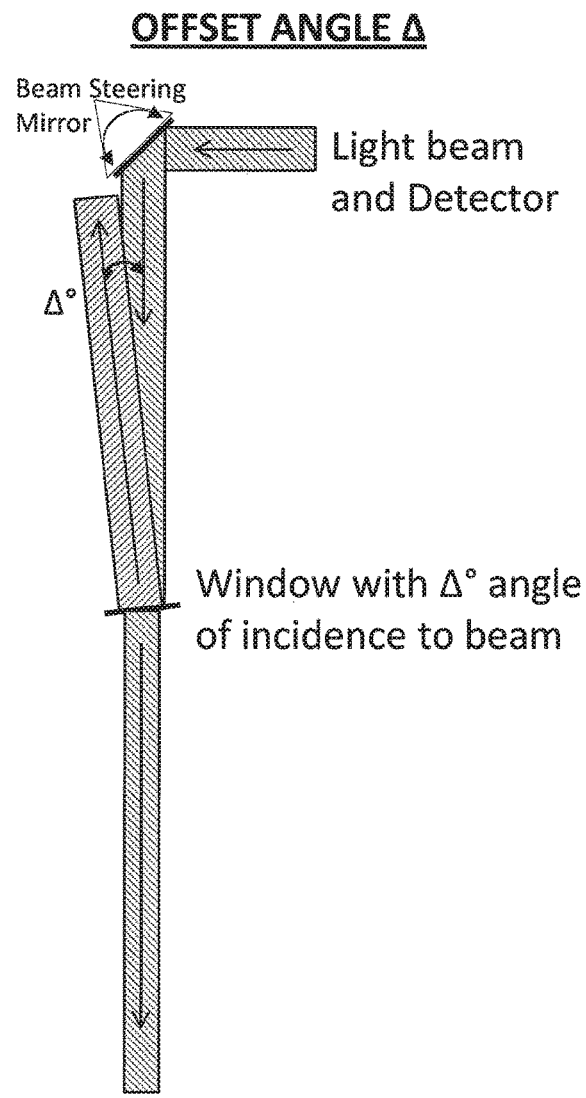
Figure 16A:
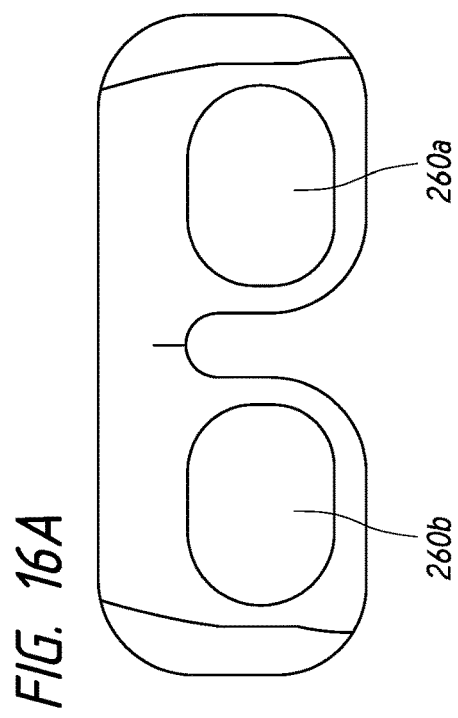
FIGS. 16A-D schematically illustrate a mask having optically transparent sections that are tilted or sloped nasally or temporally to reduce retro-reflection of light from an incident probe beam back into the optical coherence tomography instrument.
Figure 16C:
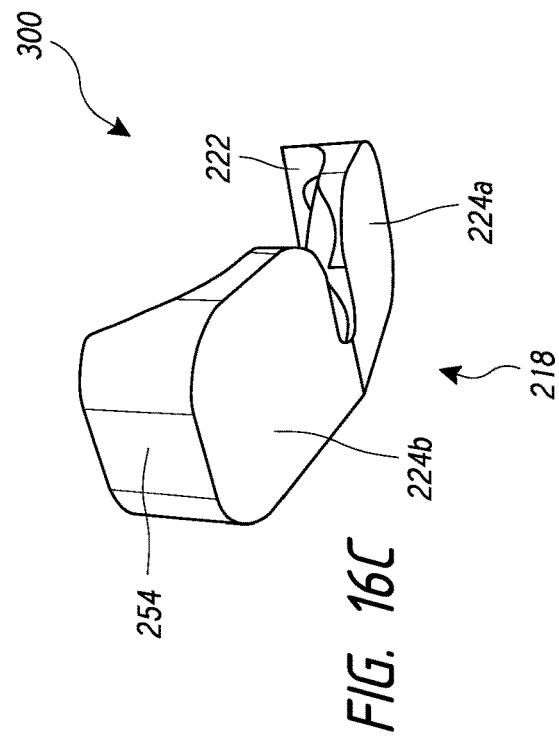
Figure 16B:
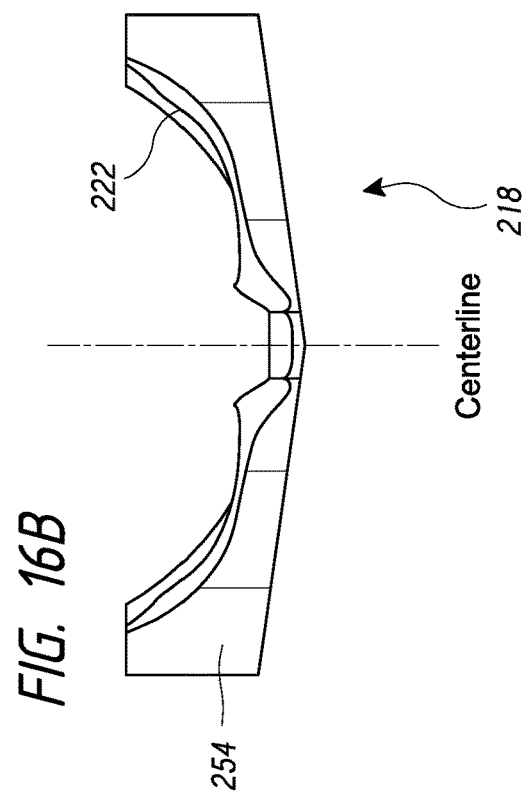
Figure 16D:
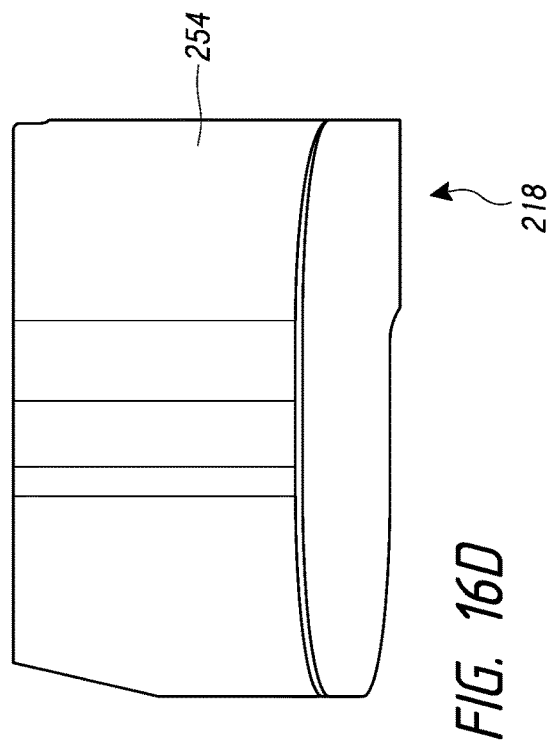

To improve the signal to noise ratio, the window can be tilted an angle with respect to the beam. This tilt angle may be β degrees. The result is that the retro-reflected beam will be tilted such that the beam cannot enter back into the OCT instrument disrupting the signal. As illustrated in FIG. 15B, for a given ophthalmic instrument such as an OCT instrument, there is an angle, Δ, of the retro-reflected beam (measured with respect to the incident beam or the incident optical path) at which the reflected beam is unlikely to enter back into the OCT instrument and introduce noise onto the OCT signal. This angle Δ may depend in part on the beam size, the size of the optics in the OCT instrument, e.g., the beam steering mirror, as well as the relative location of the optics longitudinally along the optical path. This angle may be for example, 0.5° to 1°, 1° to 2°, 2° to 3°, or combinations thereof.

In various embodiments, as illustrated in FIG. 15C, the optics in the ophthalmic instrument are configured such that rays of light from the probe beam exiting the exit pupil or ocular of the ophthalmic instrument are generally converging. For example, the probe beam may substantially fill the exit pupil of the ophthalmic instrument and be focused down. Such approach may be referred to as a flood illumination. Also, as described above, in some embodiments, a beam having a beamwidth narrower than the aperture of the ocular or exit pupil of the ophthalmic instrument is swept through a range of angles. This approach may be referred to as beam steering. In both cases light rays may be incident on the mask at a range of angles, for example, defined by a cone angle (α). This range of angles may be determined, for example, by the F-number or numerical aperture of the output of ophthalmic device such as the ocular lens or focusing lens of the ophthalmic device and/or by the movable mirror (MEMS mirror). This range of angles may also correspond to the range of angles that the ophthalmic device will collect light. For example, rays of light reflected back into this range of angles, may be collected by the ophthalmic instrument and contribute to the signal received. This collection angle may also be determined by the F-number or numerical aperture of the ocular of the ophthalmic device (e.g., OCT instrument).

In some embodiments, the tilt or slope angle of the optically transparent section 224 of the mask is configured to be greater than the largest angle of incident light produced by the OCT or other imaging or ophthalmic device. For example, if an accompanying ophthalmic (e.g., OCT) device, because of beam steering or flood illumination, produces light rays between −30 degrees and +30 degrees with respect to the optical axis of the ophthalmic device or with respect to the central axis of the optical path from the ophthalmic device to the mask (e.g., a cone angle α of 30°), the magnitude of the tilt or slope angle (β) of the optically transparent section 224 of the mask can in various embodiments be greater than the cone angle, for example, more negative than −30 degrees or more positive than +30 degrees. For example, the tilt or slope angle, β, may be less than −30° (e.g., −31°, −32° etc.) or greater than +30° (e.g., 31° or more).

FIGS. 15C-15E show how tilting the optically transparent section 224 reduces the likelihood that light exiting the ophthalmic device will be retro-reflected back into the ophthalmic device.

FIG. 15C, for example schematically illustrates a planar window 224 on the mask corresponding to the optically transparent section 224 that does not have an AR coating. The window 224 is shown receiving a bundle of rays 265 of light that are focused down by a focusing lens 270 at the output of the ophthalmic device. This focusing element 270 may be a lens (e.g., in an ocular) that outputs a focused beam of light from the ophthalmic device (e.g., OCT instrument). The focused bundle of rays 265 is show centered about a central axis 267 of the optical path from the ophthalmic device to the mask that corresponds to an optical axis 267 of the ophthalmic device (e.g., the optical axis of the focusing lens 270). The focused bundle of rays 265 may correspond to rays of light simultaneously provided with flood illumination or rays of light sweep through the range of angles over a period of time by the beam steering optics (e.g., movable mirror). FIG. 15C illustrate how, in either case, the bundle of rays 265 propagating along the optical path from the ophthalmic instrument to the eye can be reflected back toward the ophthalmic device at an angle within the collection angle defined by the numerical aperture of the lens 270 such that this light would propagate back along the same path to the ophthalmic device and re-enter the ophthalmic device possibly interfering with the signal.

FIG. 15D, for example schematically illustrates a planar window 224 on the mask having an AR coating thereon. Accordingly, the rays of light reflected from the mask window 224 are shown attenuated as back reflection is reduced by the AR coating.

FIG. 15E, for example schematically illustrates a planar window 224 on the mask without an AR coating that is tilted or sloped such that the normal (shown by dotted line) to the window is disposed at an angle, β, with respect to the central axis 267 of the optical axis from the exit pupil or ocular/eyepiece of the ophthalmic device to the window. The mask window receives a bundle of rays 265 of light (either simultaneously during flood illumination or more sequentially in a beam steering approach) focused down by a focusing lens 270 at the output of the ophthalmic device. The maximum ray angle or cone angle of the focused bundle of rays 265 is shown as a. In this example, |β|α, where α is the cone angle measured as a half angle as shown. In various embodiments, |β|−Δ>α. As discussed above, A is the angle at which the probe beam can be offset with respect to the probe optical path so as not to be coupled back into the OCT instrument via retro-reflection and thereby disrupt the OCT signal by introducing noise. (See FIG. 15B.) Accordingly, rays in the bundle of rays 265 propagating along the optical path from the ophthalmic instrument to the eye are not reflected back toward the ophthalmic device at an angle within the collection angle defined by the numerical aperture of the lens 270 such that this light does not re-enter the ophthalmic device. Tilting or sloping the window 224 sufficiently beyond the angle of the steepest ray of light from the probe beam can reduce retro-reflection. As discussed above, in various embodiments, the magnitude of the tilt or slope angle β is larger than the cone angle α, where α is the cone angle measured as a half angle as shown and is a positive value, or the magnitude of the tilt or slope exceeds the angle of the ray 268 exiting the ophthalmic device (e.g., exiting the ocular lens 270 shown in FIG. 15E) that is incident onto the mask window at the largest angle providing greater deflection away from the optical axis 267 for that ray 268. Accordingly in various embodiments, $|\beta|>\alpha$ thereby increasing the amount of rays that are not retro-reflected back through the lens 270 and into the ophthalmic device. As discussed above, in various embodiments, $|\beta|$ exceeds $\alpha$ by at least $\Delta$. The magnitude of the tilt or slope angle $\beta$ of the optically transparent section 224 may thus be greater than the cone angle $\alpha$ established by the f-number or numerical aperture of the ophthalmic device. In some embodiments, one or more of these relationships are true for 50-60%, 60-70%, 70-80%, 80-90%, 90-95%, 95-98%, 98-99%, or 99-100% of the light from the probe beam (e.g., as rays are swept through the range of angles to provide raster scanning). Combinations of these ranges are also possible.

In addition to being tilted or sloped, the optically transparent sections 224 may also be coated with an anti-reflective coating as described above. In some embodiments, the respective portion of the optically transparent sections 224 is tilted or sloping upward or downward, as illustrated in FIGS. 14A-D. In other embodiments, the respective portion of the optically transparent sections 224 is tilted or sloped temporally or nasally, or in a combination of upward/downward and nasal/temporal directions.

FIGS. 16A-D illustrate a mask 300 for performing an eye exam according to an embodiment. The mask 300 is similar to the mask 200 shown in FIGS. 14A-14D, except that two of the one or more substantially optically transparent sections 224a and 224b are tilted or sloped temporally or nasally in opposite directions with respect to each other. In an embodiment, the two substantially optically transparent sections 224a and 224b are tilted or sloped symmetrically away from the nose and nasal lines or centerline. In other embodiments, combinations of tilt directions are possible. For example, according to some embodiments, one optically transparent section 224a is tilted or sloped upward or downward, and the other optically transparent section 224b is tilted or sloped nasally or temporally. In some embodiments, a portion of the optically transparent sections 224 that intersect the incident light beam is planar, as illustrated in FIGS. 14A-14D and 15A-15E. In other embodiments, a portion of the optically transparent sections 224 is curved, as discussed below.

Figure 17C:
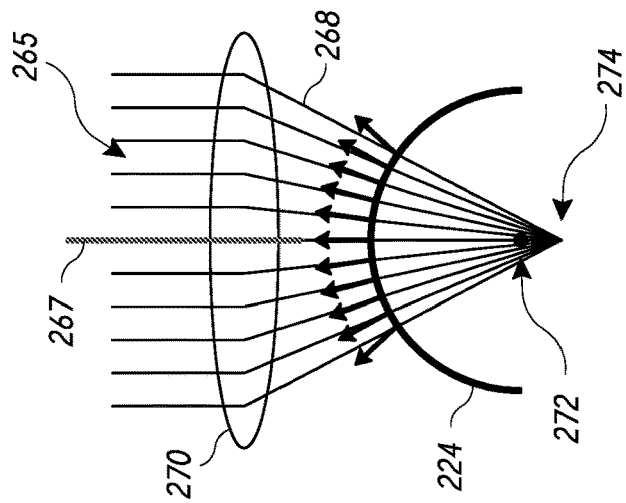
FIGS. 17A-E schematically illustrate a curved window on a mask and demonstrates how the location of the window with respect to the focus of the OCT instrument (e.g., oculars or eyepieces) can vary the amount of retro-reflection of light from the optical coherence tomography instrument back into the OCT instrument.
Figure 17B:
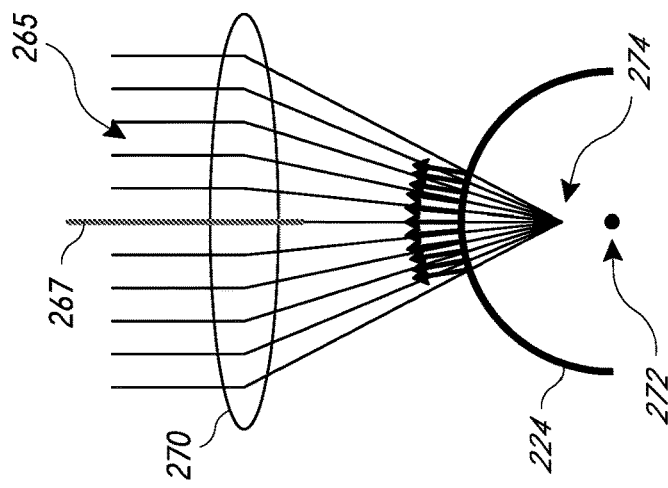
Figure 17A:
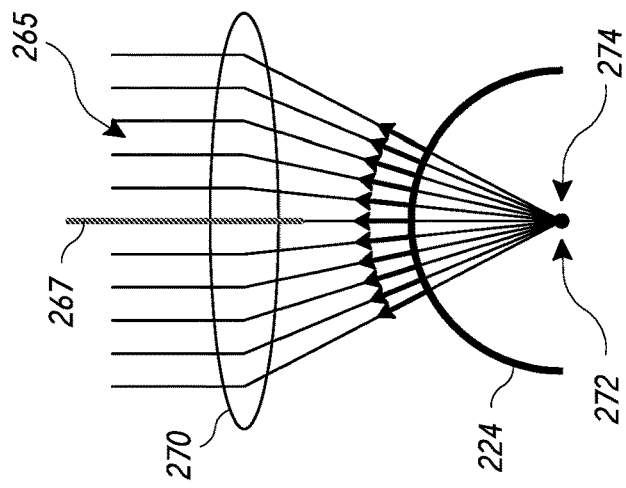

FIGS. 17A-17C, for example, illustrate how curved windows 224 can be used as the optically transparent sections 224 of a mask and the effect of such curved windows on an incident probe beam 265. In certain embodiments, depending on the placement of the incident beam 265 with respect to the mask window 224, the window may provide a perpendicular surface for many of the rays of light in the beam thereby causing retro-reflection back into the channels of the ophthalmic instrument thereby contributing to noise in the signal.

FIG. 17A, for example, shows a curved window 224 without an AR coating having a center of curvature 272 that is located at the focus point 274 of the optics 270 of the ophthalmic device. Such alignment can cause a significant portion of the light to be retro-reflected back into the ophthalmic device. The focus point 274 of the optics 270 in the ophthalmic device may comprise the focal point of the lens or optics in the ophthalmic system (e.g., in the ocular or eyepiece or left or right output channel).

FIG. 17B shows a curved window 224 without AR coating having a center of curvature of the window that is behind or beyond the focus point of the lens 270. This positioning may be determined in part by the mask and the interconnection between the mask and the ophthalmic device that establishes the spacing between the ophthalmic device and the eye of the subject wearing the mask. In FIG. 17B, rays of light are retro-reflected back toward the ophthalmic device at an angle within the collection angle defined by the numerical aperture of the lens 270 such that this light re-enters the ophthalmic device.

In contrast, FIG. 17C shows a curved window 224 without AR coating having the center of curvature that is in front of the focal point 274 of the optics. As discussed above, this positioning may be determined in part by the mask and the interconnection between the mask and the ophthalmic device that establishes the spacing between the ophthalmic device and the eye of the subject wearing the mask. Some of the rays on the outer parts of the cone of rays 265, including the ray 268 directed at the largest angle are not retro-reflected back toward the ophthalmic device at an angle within the collection angle defined by the numerical aperture of the optics 270 such that this light does not re-enter the ophthalmic device. However, rays closer to the optical axis 267 are closer to being perpendicular with the normal of the window such that those rays are retro-reflected back toward the ophthalmic device at an angle within the collection angle defined by the numerical aperture of the optic 270 and thus re-enter the ophthalmic device. In various embodiments where the ophthalmic device is a beam-scanning device such as an OCT device or a scanning laser ophthalmoscope, a small offset angle between the cone of rays 265 and the slope of the curved window 224 is sufficient to sufficiently reduce or prevent retro-reflection of light into the ophthalmic device.

Figure 17E:
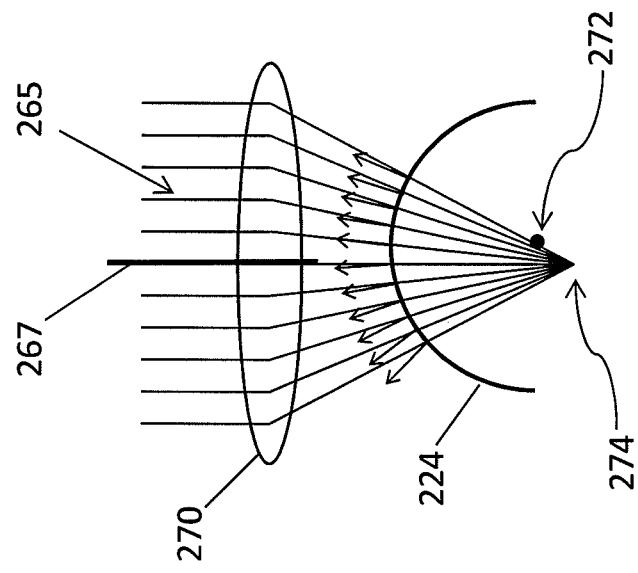
Figure 17D:
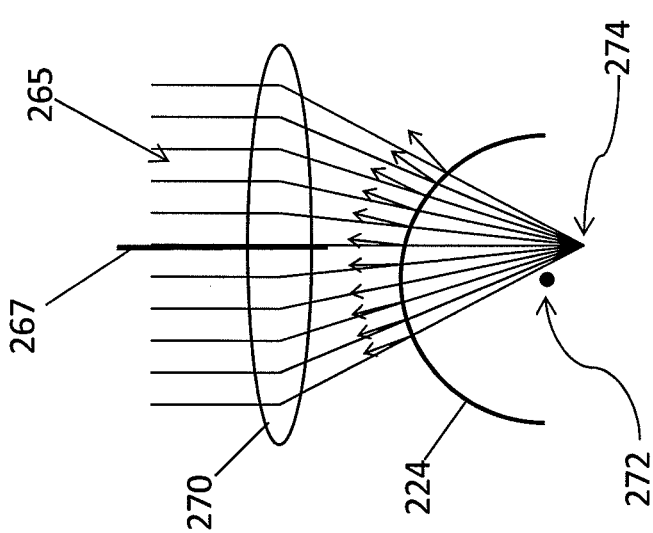
Figure 18C:
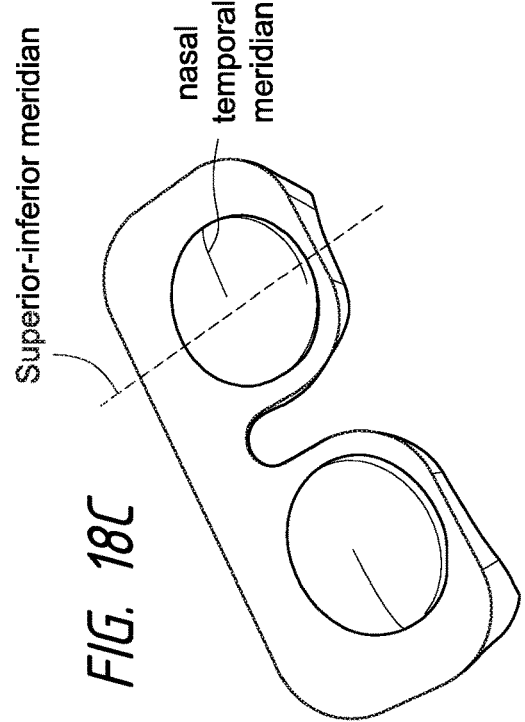
FIGS. 18A-D schematically illustrate a mask having optically transparent sections that are curved to reduce retro-reflection of light from the optical coherence tomography instrument back into the OCT instrument.
Figure 18D:
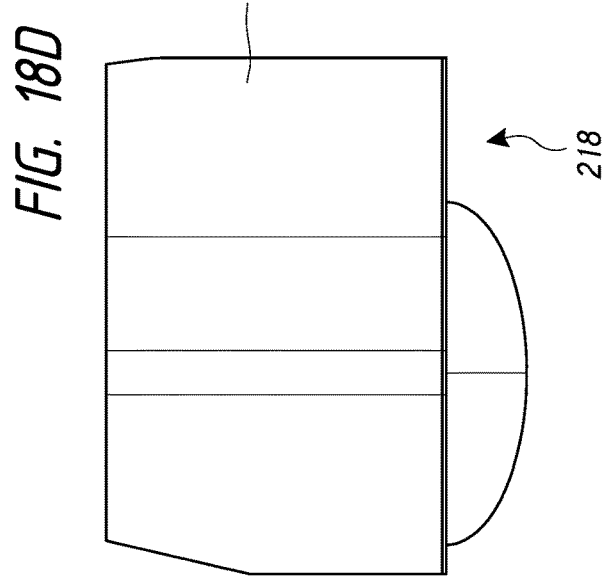
Figure 18A:
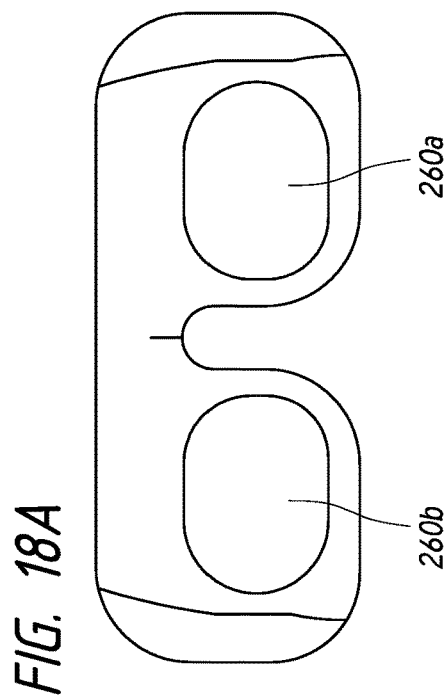
Figure 18B:
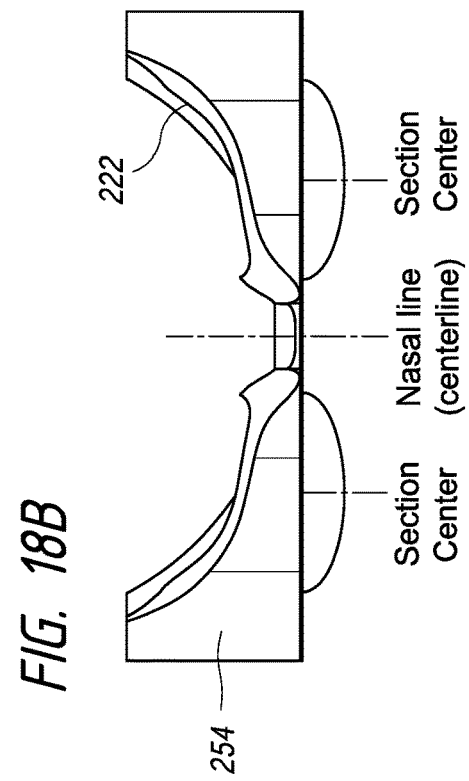

FIGS. 17D and 17E schematically illustrate shifts of the center of curvature of the window to the left and the right. FIG. 17D shows a curved window 224 without AR coating having a center of curvature of the window that is to the left of the focus point and optical axis 267 of the lens 270. This positioning may be determined in part by the mask and the interconnection between the mask and the ophthalmic device that establishes the spacing and positioning between the ophthalmic device and the mask as well as the eye of the subject wearing the mask. In FIG. 17D, rays of light that intersect the curved window 224 to the right of its center of curvature are retro-reflected at an angle that is substantially directed away from the lens 270 and the optical axis 267. Light that intersects the window 224 to the left of its center of curvature is retro-reflected back toward the ophthalmic device at an angle within the collection angle defined by the numerical aperture of the lens 270 such that this light re-enters the ophthalmic device.

Similarly FIG. 17E shows a curved window 224 without AR coating having a center of curvature of the window that is to the right of the focus point and optical axis 267 of the lens 270. As discussed above, this positioning may be determined in part by the mask and the interconnection between the mask and the ophthalmic device that establishes the spacing and positioning between the ophthalmic device and the mask as well as the eye of the subject wearing the mask. In FIG. 17E, rays of light that intersect the curved window 224 to the left of its center of curvature are retro-reflected at an angle that is substantially directed away from the lens 270 and the optical axis 267. Light that intersects the window 224 to the right of its center of curvature is retro-reflected back toward the ophthalmic device at an angle within the collection angle defined by the numerical aperture of the lens 270 such that this light re-enters the ophthalmic device.

In these examples the windows 224 are spherical. In other embodiments, however, the window 224 may have a curved surface other than spherical, e.g., aspheric surface curvature. In addition to being tilted or sloped, the curved optically transparent sections 224 may also be coated with an anti-reflective coating as described above.

FIGS. 18A-D illustrate a mask 300 for performing an eye exam similar to the mask 200 shown in FIGS. 14A-14D, except that two of the one or more substantially optically transparent sections 224*a* and 224*b* are curved. In particular, the substantially optically transparent sections 224*a* and 224*b* have outer surfaces as seen from the front of the mask having a convex shape. These curved surfaces may be spherical in shape or may be aspherical. For example, the curved surfaces may be an ellipsoidal surface or an oblate spheroid surface, or have a shape characterized by a higher order polynomial or be combinations thereof. Other shapes are possible. In various embodiments, the surface is more flat at the center of the substantially optically transparent section and curves or slopes more steeply away from the center of the substantially optically transparent section as shown by FIG. 18A-D. In some embodiments, the mask has a size and the substantially optically transparent sections are disposed such that the flatter central portions of the substantially optically transparent section are along the line of sight of the wearer. Accordingly, in various embodiments, the surface is flatter closer to the normal line of sight and slopes more steeply away from the normal line of sight.

Various embodiments of masks having optically transparent sections 224*a* and 224*b* that are curve and may be plano and have negligible optical power. Not having optical power will likely contribute to the comfort and viewing experience of the wear. Accordingly optically transparent sections 224*a* and 224*b* may have anterior and posterior surfaces having shapes that together provide that the optically transparent sections 224*a* and 224*b* have substantially zero diopters of optical power. In some embodiments, however, the optically transparent sections 224*a* and 224*b* may have optical power such as to accommodate individuals who need refractive correction.

In some embodiments, the angle of incidence varies across transparent section 224. A curved window 224 depending on the shape and/or position with respect to the focus of the probe beam may cause the angle of incidence to vary across the transparent section 224.

Figure 19:
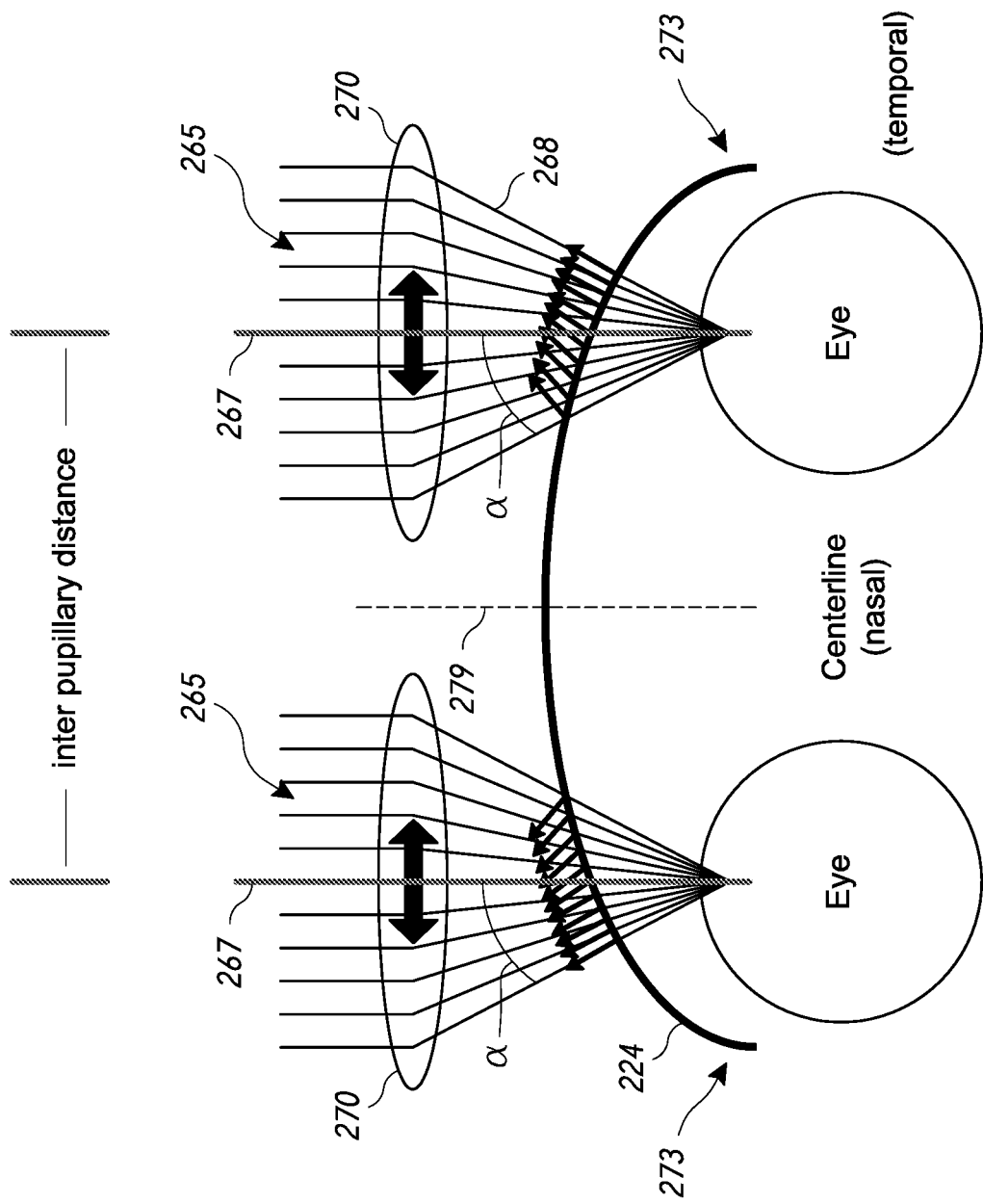
FIG. 19 schematically illustrate a curved window on a mask disposed forward of a pair of eyes separated by an interpupilary distance wherein the window is increasing sloped more temporal from a center line through the window thereby exhibiting wrap that reduces retro-reflection of light from the optical coherence tomography instrument back into the OCT instrument.
Figure 21B:
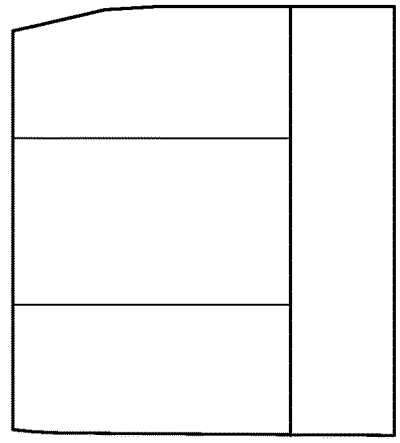
FIGS. 21A-21D, 22, 23, 24, 25A-25D, 26, and 27 schematically illustrate differently shaped mask windows.
Figure 21D:
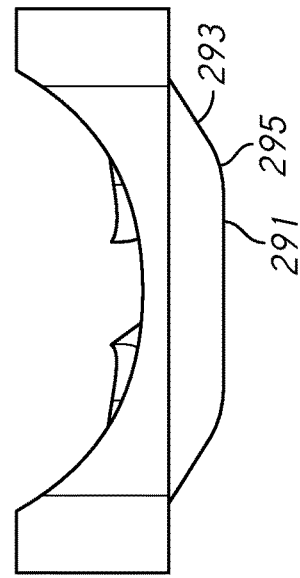
Figure 21A:
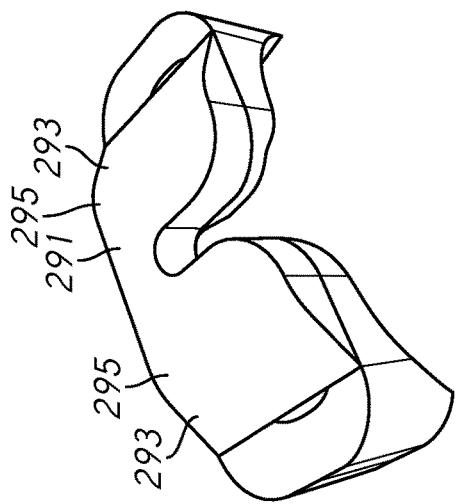
Figure 21C:
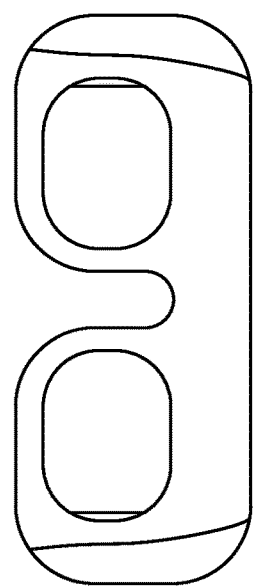

FIG. 19 schematically illustrates a window 224 of a mask disposed in front of a pair of eyes such that most of the rays of light from the incident beam are reflected at angles beyond the collection angle within the numerical aperture of the optics 270 or exceeds an offset angle Δ described above for beam-scanning devices. Accordingly, most of the light does not re-enter the ophthalmic device. In particular, the window 224 is sloped except for at the centerline where the nose of the wearer is located. Additionally, the window has a slope that increases in magnitude temporally. Moreover, the window is sloping such that all the rays in the cone of rays 265 of the incident beam are directed temporally upon reflection (unlike in the examples shown in FIGS. 17A-C).

In the example shown in FIG. 19, the window 224 has a slope and curvature that increases in magnitude temporally such that the slope or curvature is maximum at the periphery or edges 273 of the window 224. This slope or curvature at the location of the line of sight (e.g., within a range of interpupilliary distances between 50-80 mm or 25-40 mm from the centerline) is sufficiently high in magnitude to exceed the angle of the ray 268 exiting the ophthalmic device (e.g., exiting the ocular lens 270) at the largest angle that is incident onto the mask window 224. Additionally, the slope or curvature of the window 224 is sufficently high in magnitude to deflect all or substantially all or at least most of the other rays away from the optical axes 267 of the output channels of the ophthalmic device. At each point where rays from the probe beam intersect the window 224, the normal to the window surface is oriented with respect to the cone of rays 265 to deflect the ray outwards or to retro-reflect the probe beam at an angle Δ described previously for beam-scanning devices. Moreover, the rays are deflected sufficiently so as not to be retro-reflected at an angle within the collection angle defined by the numerical aperture of the output channel of the ophthalmic device such that this light is not coupled back into the ophthalmic device so as to interfere with the signal (e.g., the OCT signal).

Additionally, in various embodiments, the width of this curved window 224 may be sufficient to account for the lateral position and movement of the oculars or output channels of the ophthalmic device. Increasing the interpupillary distance of the pair of output channels of the ophthalmic device effectively pushes the outermost ray 268 more temporally. Accordingly, the width and curvature of the window 224 on the mask can be established to ensure that half, or most, or substantially all, or all the rays of light from the left and right output channels of the ophthalmic instrument are at a given instant in time or over the range of angles swept during a raster scan not incident on the mask window at an angle where the rays are retro-reflected back at an angle within the collection angle defined by the numerical aperture of the channels such that the light is collected by the channels and introduces noise to the signal. For example, if the angle of the ray 268 exiting the left and right channels of the ophthalmic device at the largest angle is 35 degrees (e.g., if the cone angle α is ±35°, and the maximum lateral position of those rays is 40 mm from the centerline 279 or nose line on the window of the mask, a shape can be configured for the window that ensures that none or substantially none of the rays are incident on the transparent window in a perpendicular orientation and instead cause most, all, or substantially all the incident light to deflect outside the collection angle defined by numerical aperture of the left and right channels of the ophthalmic devices.

As discussed above, the substantially optically transparent sections 224*a* and 224*b* have outer surfaces as seen from the front of the mask having a convex shape and are aspherical. For example, the curved surfaces may be ellipsoidal, toroidal, or have a shape characterized by a higher order polynomial or combinations thereof.

Additionally, in various embodiments the optically transparent sections 224*a* and 224*b* are plano and have negligible optical power. The optically transparent sections 224*a* and 224*b* may have anterior and posterior surfaces having shapes that together provide that the optically transparent sections 224*a* and 224*b* has substantially zero diopters of optical power. In some embodiments, however, the optically transparent sections 224*a* and 224*b* may have optical power to accommodate individuals who need refractive correction.

Moreover, the transparent section 224 can be comprised of a curved transparent outer surface sufficiently sloped such that the angle of incidence of the rays of light output by an accompanying OCT machine when interfaced with the mask is not normal to the transparent section 224 at most or substantially all the points of incidence on transparent section 224 and the slope or tilt is configured to deflect the rays away from the optical axis and outside the collection angle of the OCT machine (e.g. |β|>α). In some embodiments, such as beam-steering optical devices, the difference between angle |β| and angle α is be greater than an angle Δ such that |β|—Δ≥α to prevent any retro-reflected beam from impinging on the beam-steering device, such as a galvanometric mirror or MEMS mirror, and being sensed by the device. In some embodiments, this relationship is true for 50-60%, 60-70%, 70-80%, 80-90%, 90-95%, 95-98%, 98-99%, or 99-100% of the light from the probe beam as used (e.g., flood illumination or swept) to generate images by the ophthalmic device or combinations of these ranges.

Accordingly, in various embodiments, only 3-5% or 2-4%, or 1-3% or 0.5-1% or 0.1-0.5% or 0.05-0.1% or 0.01-0.05% of the light is reflected back into the ophthalmic device.

FIGS. 20A-D schematically illustrate a mask 300 for performing an eye exam having transparent sections 224 with curvatures such as shown in FIG. 19. Accordingly, the transparent sections 224, sometimes referred to herein as a mask window or curved transparent section, has wrap and sweeps back progressively with distance from a centerline of the mask (nasal line) 273 where the nose of the wearer would be positioned. Additionally, the mask window also has curvature in the superior-inferior meridian. Accordingly, this mask may reduce retro-reflection of light from the optical coherence tomography instrument back into the instrument.

In some embodiments, the curved transparent section 224 extends across all of distal portion 218. In some embodiments, curved transparent section 224 is only a portion of distal portion 218 (e.g., see FIGS. 21A-21D in which the optically transparent section does not extend to or is displaced from the lateral edges of the mask). As shown, the mask has a front sheet that sweeps backward (e.g., posterior) and outward (e.g., lateral) from the centerline 279 and provides suitable curvature to reduce reflection back into the OCT instrument and thereby reduce noise on the OCT signal.

In certain embodiments for example, the mask includes left and right substantially optically transparent sections 224a, 224b disposed on left and right sides of the centerline 273. The left and right substantially optically transparent sections 224a, 224b may be disposed with respect to each other to accommodate interpupilary distances (see FIG. 19) between about 50-80 mm, for example, for adults. Accordingly, the distance between the normal line of sight and the centerline (which can be centered on the nose of the patent) is about 25-40 mm. In some embodiments, at least the right substantially optically transparent section 224a (or the left section 224b or both) has at least a portion thereof that is sloped such that at a location on the right substantially optically transparent section 224a (left section 224b or both) that is 30 mm from the centerline (e.g., lateral of the superior inferior meridian), the right substantially optically transparent sections is sloped by at least 10° or more, at least 20° or more, at least 30° or more, at least 40° or more, at least 50° or more up to 70° or 80° or 90°, with respect to a line through that location that is parallel to the centerline. This angle may be established by the cone angle α discussed above and can have a magnitude greater than 10° such as more than 15°, 20°, 25°, 30°, 35°, 40°, 45°, 50°, 55°, 60°, up to 70° or 80° or 90° etc. The right substantially optically transparent section (or left section or both) may have the same slope magnitude or be increasingly sloped (for example, have a magnitude greater than for example 10° 15°, 20°, 25°, 30°, 35°, 40°, 45°, 50°, 55°, or) 60° at locations progressively more temporal from the location (e.g., greater than 30 mm in distance from the centerline) at least to about 35 mm or 40 mm etc. from said centerline. In some embodiment, the location can be 20 mm, 22.5 mm, 25, mm, 27 mm, 29 mm, 31 mm, 33 mm, 35 mm, 37 mm, or 39 mm, or any range therebetween. In some embodiments, at 25 mm from the centerline, the magnitude of the slope may be greater than for example 10° 15°, 20°, 25°, 30°, 35°, 40°, 45°, 50°, 55°, or 60° and/or the slope may exceed the cone angle such that the outermost ray of light from the ocular in the ophthalmic instrument is deflected away from the optical axis of the ocular. Likewise, for locations progressively more temporal, the optically transparent section may be sloped (for example, may have a slope with magnitude greater than for example 10° 15°, 20°, 25°, 30°, 35°, 40°, 45°, 50°, 55°, 60°), may have constant slope, or varying slope, e.g., increasingly sloped. Additionally, in some embodiments, the right (left or both) substantially optically transparent section(s) is sloped by at least 15°, 17°, 19°, 21°, 23°, 25°, 27°, 29°, 31°, 33°, 35°, 37°, 39°, 41°, 43°, 45°, 47°, 49°, 51°, 53° or 55°, in magnitude at said location or ranges therebetween. Accordingly, in some embodiments the substantially optically transparent section sweeps back as illustrated in FIG. 19.

Likewise, the window exhibits wrap. In some embodiments, the window wraps at least partially around the side of the face or at least begins to wrap around the side of the face. This curvature is desirable where the rays of light from the ophthalmic instrument might intersect the optically transparent window. Since different subjects will have different interpupilary distances, and the ophthalmic instrument may be adjusted accordingly to direct the probe beam through the pupil of the eye, the rays from the probe beam may be incident over a range of locations on the substantially optically transparent sections. A window that exhibits wrap over a region thereof may thus be desirable to reduce retro-reflection back into the instrument. In various embodiments, windows that sweep rearward with distance progressively more temporal of the centerline 273 of the mask 300 are useful in deflecting light temporally and outside the collection angle of the ophthalmic device. The slopes may be substantially constant in the temporal region or may be varying.

Although FIG. 19 is a useful reference for the discussion above where curvature is shown along a nasal-temporal meridian, in considering the superior-inferior meridian, reference to FIGS. 17A-E may be beneficial. In various embodiments, the window is curved along the superior-inferior meridian. This curvature as well as the distance of mask from the ocular on the ophthalmic instrument (as established by the mechanical interface between the mask and the ophthalmic device) may be such that a plurality of, many, possibly most, or substantially all rays in the bundle of rays from the ocular are deflected upward or downward and outside the collection angle of the ocular.

Figure 26:
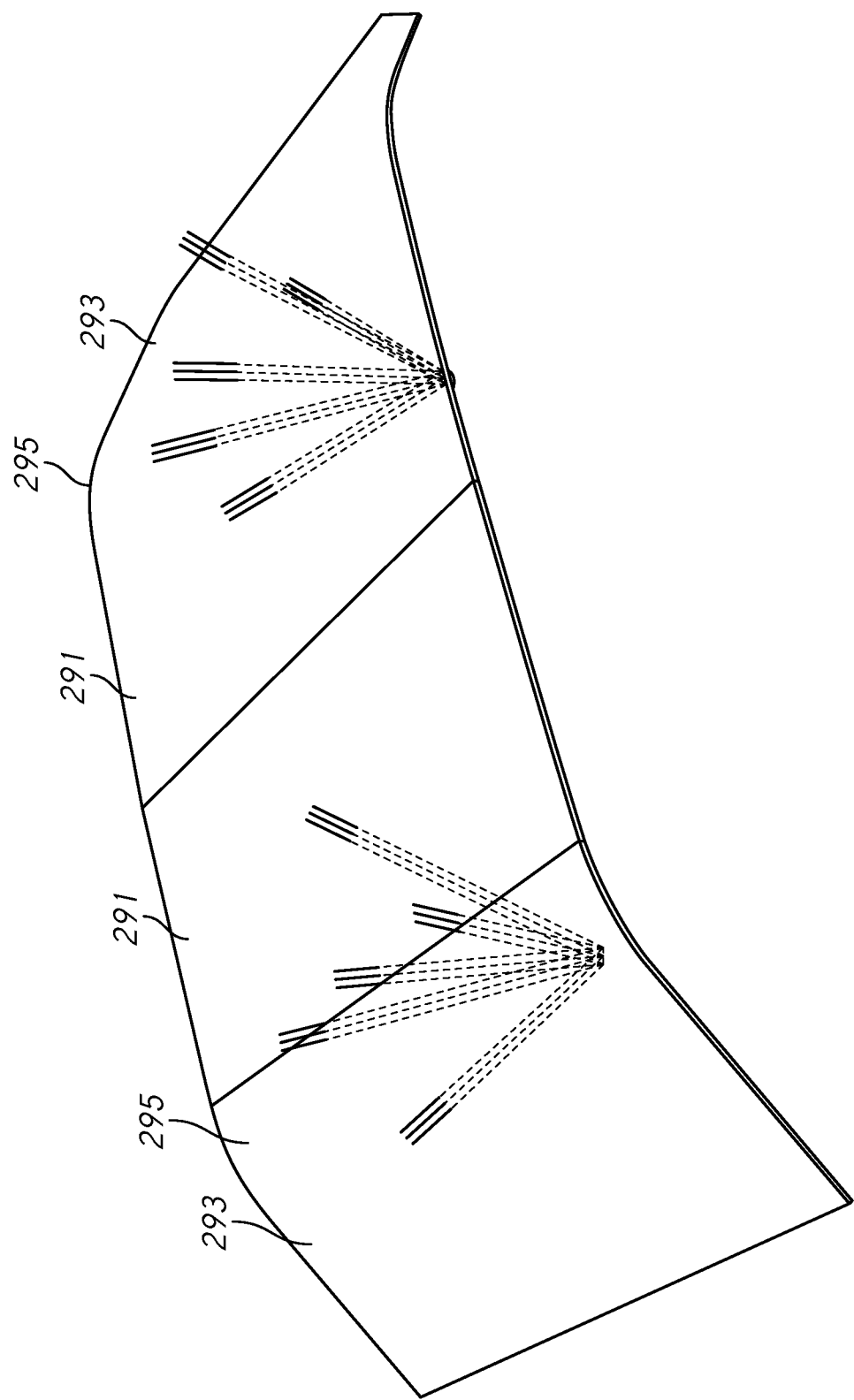
Figure 27:
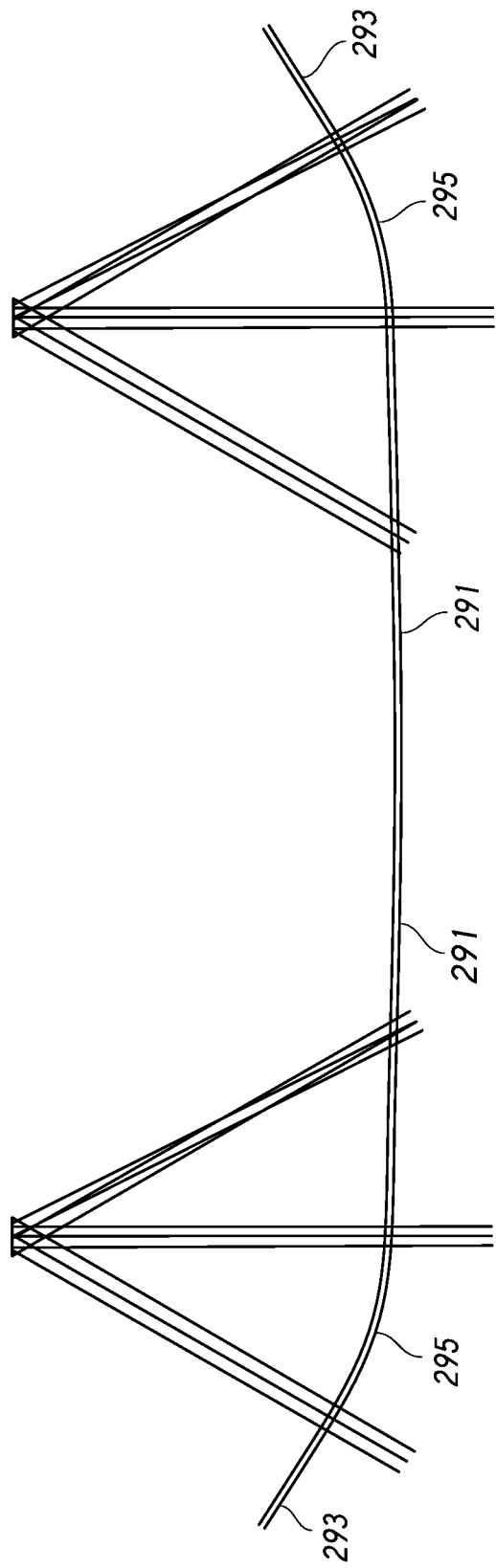

In various embodiments, combinations of tilt directions and curvature of transparent sections are possible. FIGS. 21A-21D, 22, 23, 24, 25A-25D, 26, and 27 show additional designs having differently shaped windows. FIGS. 21A-D as well FIGS. 26 and 27 schematically illustrate a design having a planar portion 291 of the substantially transparent section that is located more nasally and an adjacent planar sloping portions 293 located temporally. A transition 295 between these portions 291, 293 is curved. In certain embodiments, this transition 295 has a curvature of a circular arc having a center and radius of curvature. The sloping portions may slope along a nasal-temporal direction. Curvature or slope in the superior-inferior direction is negligible. Additional discussion regarding this design is provided below in connection with FIGS. 28A-D.

Figure 22:
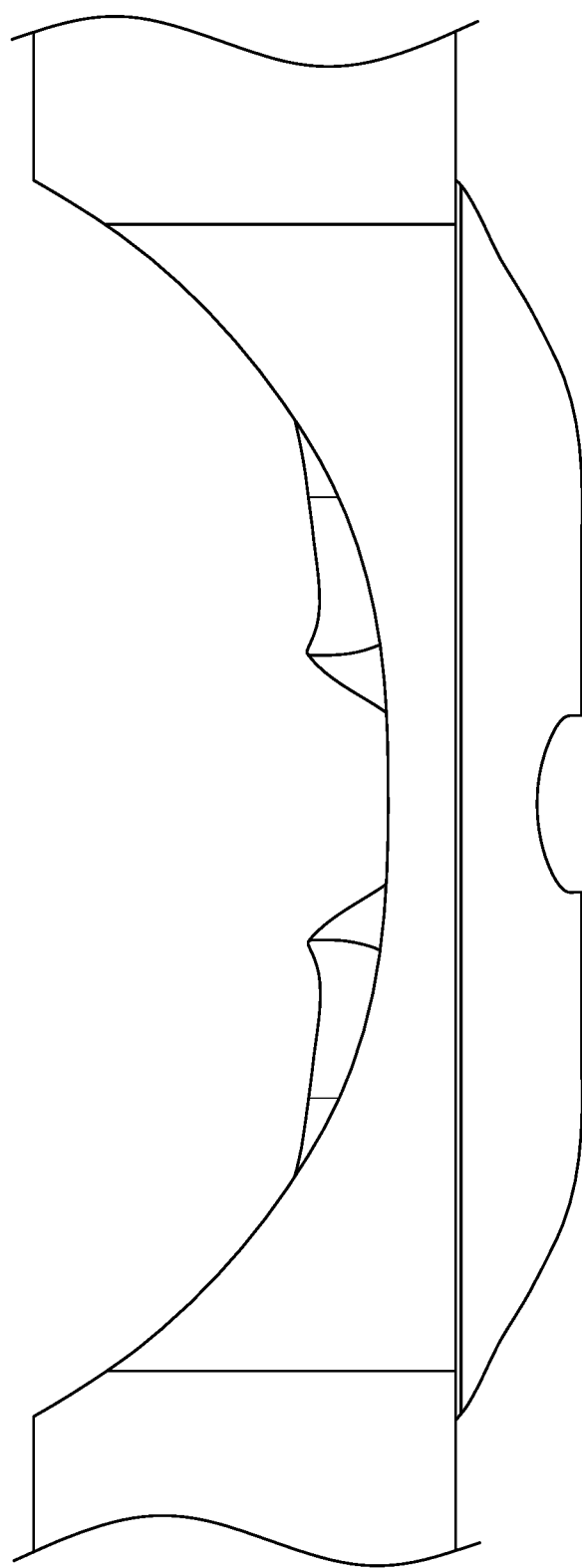
Figure 23:
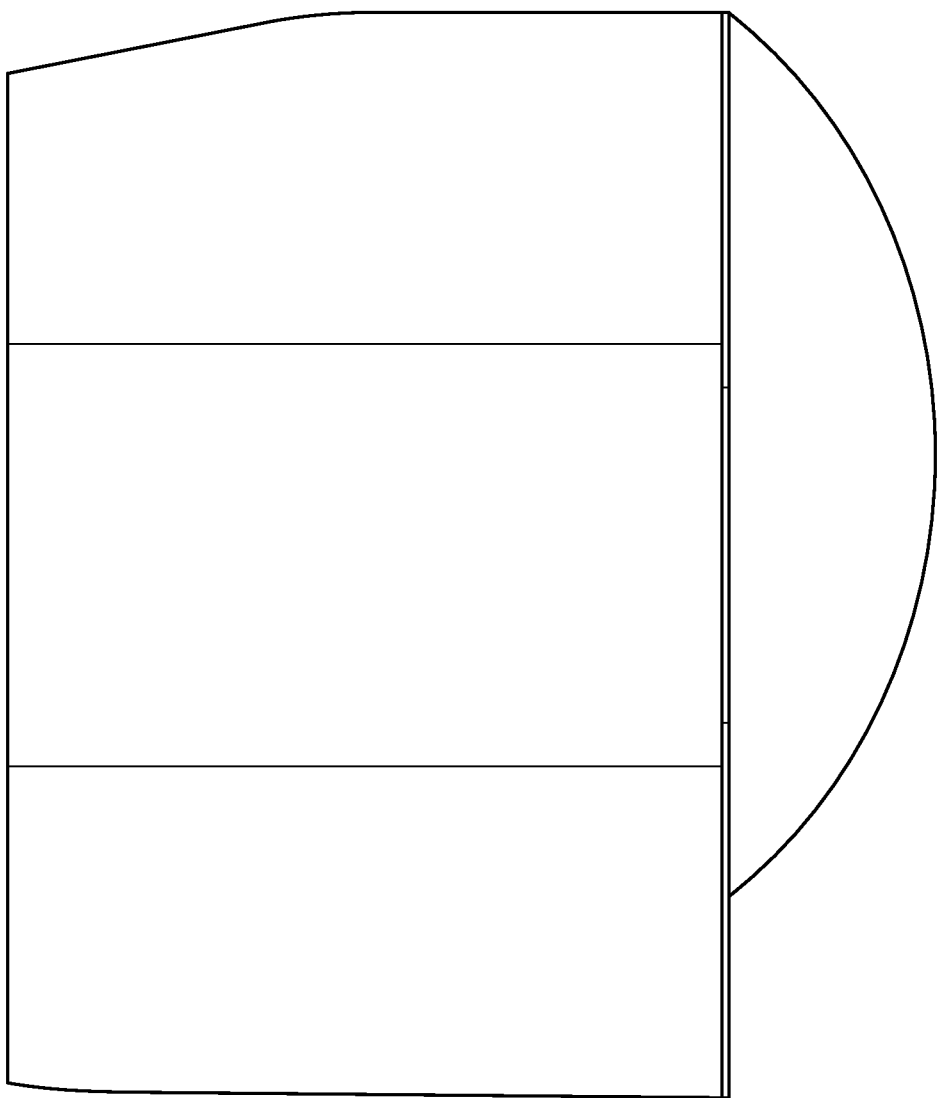
Figure 24:
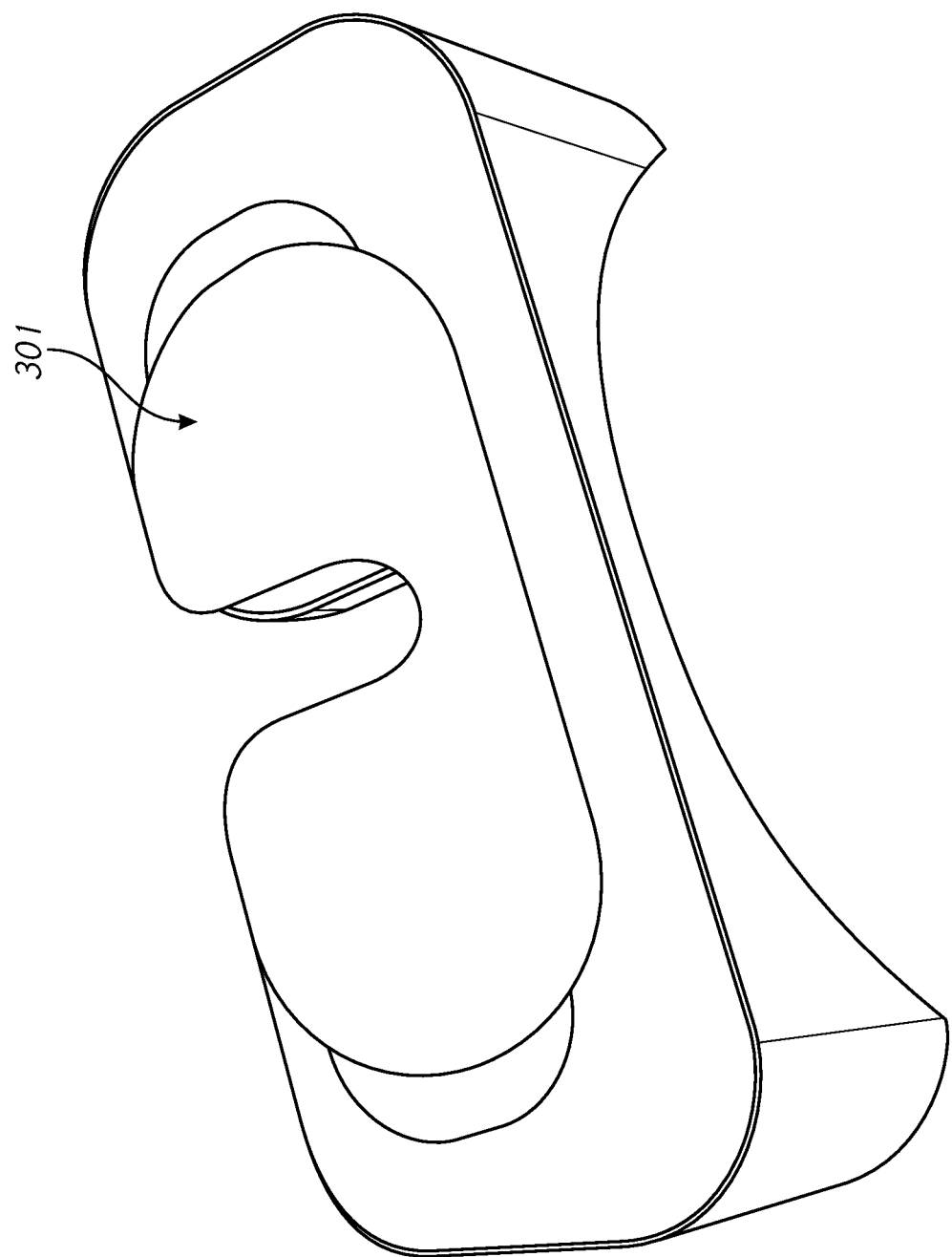
Figure 25B:
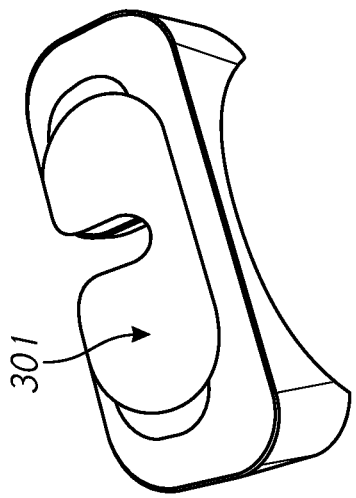
Figure 25D:
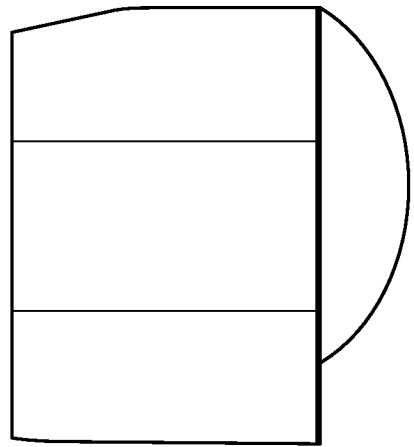
Figure 25A:
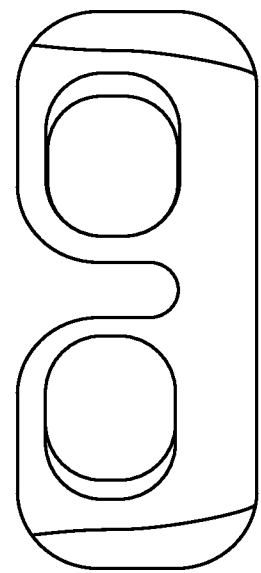
Figure 25C:
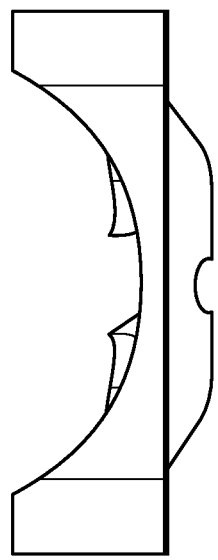

FIGS. 22-24 and 25A-D show transparent sections that are curved in both nasal-temporal meridian and superior-inferior meridian. (FIGS. 22 and 23 show the same compound curved surface as in FIG. 24.) In various embodiments such as shown in FIG. 25B, the curvature or slope of the substantially transparent section 301 in the nasal-temporal direction is negligible closer to the centerline until reaching a temporal location where the magnitude of the slope increases temporally to generate a curved temporal section that sweeps backward. The curvature or the magnitude of the slope of the substantially transparent section 301 along the superior-inferior meridian starts out high in magnitude at the inferior location, reduces in magnitude to a negligible amount halfway between the inferior and superior extent of the convex shaped substantially transparent section 301 and increases again at the superior locations. The curvature is such that the magnitude of slope increases with increasing distance superiorly and inferiorly beyond the central flat non-sloping region. The curvatures do not slope or the slope is substantially negligible along the nasal temporal meridian in this central flat non-sloping region as well. In various embodiments this central flat non-sloping region can be ⅓ or ½ to ¾ the extent of the convex shaped substantially transparent section along the nasal temporal meridian, the superior inferior meridian, or both.

FIGS. 28A-D illustrate some of the design considerations entailed in various embodiments of the mask window. For certain ophthalmic instruments, different modes of operation may involve use of probe beams with different characteristics.

FIG. 28A for example, illustrates a mode of operation where an OCT instrument is configured to output a planar non-focused wavefront. Optics in the OCT instrument are configured to be telecentric. FIG. 28A therefore shows on a plot of angle of incidence (in degree) versus distance (in mm) from the centerline, the output from the ocular or eyepieces for the left and right channels of the ophthalmic device (e.g., OCT instrument). The plot shows an angle of 0° for each of the rays across the aperture of the ocular for both the left and right channels.

FIG. 28B illustrates a mode of operation where an OCT instrument is configured to output beam that sweeps across a range of angles α as discussed above. A plot of angle of incidence (in degree) versus distance (in mm) from the centerline shows the output of the ocular or eyepieces for the left and right channels of the ophthalmic device (e.g., OCT instrument). These plots show the change in angle for the different rays across the aperture of the ocular for both the left and right channels.

The OCT instrument is configured to provide modes of operation using probe beams characterized by the plots shown in FIGS. 28A and 28B. Accordingly, in various embodiments, a mask that can reduce retro-reflection back into the OCT system for both of these modes is beneficial. The signal-to-noise ratio can thereby be increased by curtailing introduction of noise into the signal by retro-reflection off the mask. Accordingly, FIG. 28C shows the combination of angles of incidence in the probe beam for the two modes on a single plot.

Figure 28D:
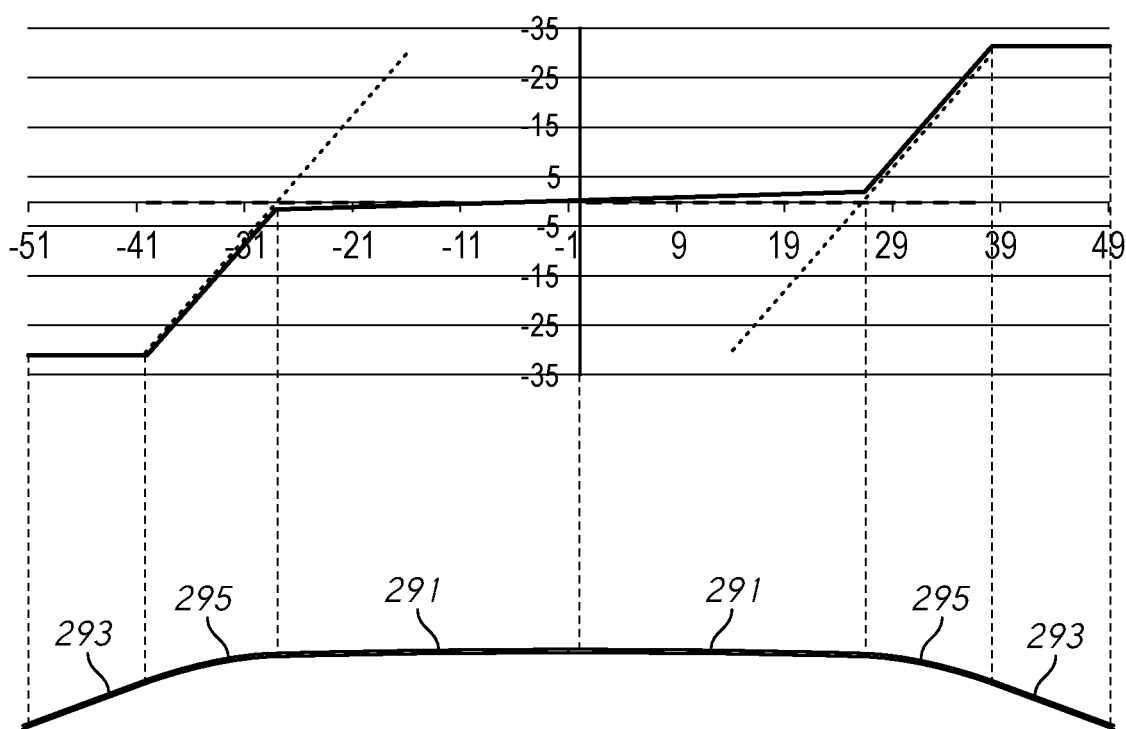

FIG. 28D presents a solution for reducing retro-reflection. As discussed above, rays perpendicularly incident on the mask will be retro-reflected back into the OCT instrument and introduce noise to the OCT signal. However, by adding a slight offset Δ to the reflected beam such that the beam is not incident perpendicular on the mask and does not reflect directly back in the same direction the amount of rays that return back into the OCT instrument can be reduced. The plot in FIG. 28D, shows the addition of this offset. In particular, an offset of 1° has been provided.

In this example, the inter-optical distance, the distance between the centers or optical axes of the oculars or eyepieces, which is related to the interpupillary distance of the subject, was 54°. Accordingly, a line of sight for wearers would be expected to be at 27° in both directions from the centerline for each of the left and right eyes. The magnitude of the slope of the mask is therefore set to increase continuously in the regions between 27 mm and about 38 mm where the magnitude of the slope reaches a maximum (just beyond the angle of the outermost ray in the bundle shown in FIGS. 28A and 28B). This curvature is to address the mode of operation represented by FIG. 28B. The small 1° in the region between 0 mm and 27 mm is to address the mode of operation represented by FIG. 28A where the rays are each at an angle of incidence of 0° without the offset. FIG. 28D shows a cross-section of the mask. The cross-section shows a wide central region 291 between for the right eye between 0 and 27 mm without a large amount of slope, a transition region 295 between 27 mm and 38 mm where the magnitude of the slope is increasing, and a region 293 from 38 to 49 mm where the slope magnitude remains constant. A similar shape could be used for the left eye thereby providing a symmetrical configuration.

Other variations are possible. For example, in one embodiment, for the right eye, the magnitude of the slope at 27 mm could be set to be so large as to account for α+Δ, namely, β≥α+Δ at 27 mm. The transition region 295 could thus start around 13 or 14 mm and be complete by 27 mm where the magnitude of the slope could remain constant for distances beyond 27 mm (e.g., in region 293). In the region 291 between 0 to 13 or 14 mm, the small slope offset of 1° or so could be introduced. A similar shape could be used for the left eye thereby providing a symmetrical configuration.

The various shaped windows may further include an AR coating as discussed above.

As illustrated in FIGS. 15B, 26, and 27, rays of light corresponding to the probe beam may be swept. For example, the probe beam (for OCT or SLO) may comprise a beam having a small beam width (e.g., 5 to 10 times or more smaller than the exit pupil of the ocular) that is swept across the focusing lens and/or exit pupil in the ocular of the ophthalmic device. Accordingly, only portions of the rays in the bundle of rays described above will be present at a given time. Nevertheless, in various embodiments, the beam sweeps through the different angles within the cone of angles, α, referred to above. Accordingly, as discussed above, the shape of the mask window can be configured to be sufficiently sloped such that these rays, and in particular, this small beam, is not retro-reflected back into the instrument to introduce noise into the signal as the beam is swept through the range of angles defined by the cone angle, α.

In some embodiments, similar to the mask 100 illustrated in FIG. 1, the proximal portion 254 of the mask 200 is inflatable or deflatable, and the rear surface 222 is configured to conform to contours of the patient's face and align the one or more substantially optically transparent sections 224 of the distal portion 218 with the patient's eyes when the proximal portion 254 is inflated or deflated. In some embodiments, the mask 200 includes an inflation port (not shown) providing access to inflate or deflate the proximal portion 254. In some embodiments, the proximal portion 254 has two cavities 260a and 260b extending from the rear surface 222 toward the distal portion 218. The two cavities 260a and 260b are aligned with the one or more substantially optically transparent sections 224 and defining two openings on the rear surface 222 to be aligned with the patient's eyes. The rear surface 222 is configured to seal against the patient's face so as to inhibit flow of fluid into and out of the two cavities 260a and 260b through the rear surface 222. In some embodiments, the mask 200 includes an ocular port (not shown) providing access to at least one of the two cavities for gas or fluid flow into the at least one of the two cavities 260a and 260b.

In some embodiments the mask is reusable. In other embodiments, the mask is single use or disposable and intended to be used by one patient, subject, or user, and subsequently disposed of and replaced with another mask for use for another person.

In various embodiments, the optical transparent sections 124 of the mask are configured to increase or maximize transmission of light, such as from an OCT device, and the proximal portions 154 and concaved rear surface 122 is configured to reduce or minimize transmission of light, such as ambient light or light not emanating from an OCT machine and may be opaque and include opaque sides. For example, the proximal portions 154 may have sides that are substantially non-transmissive to visible wavelengths. These sides may for example block 80-90%, 90-95%, 95-99%, and/or 99-100% of ambient visible light. Reduction of ambient light may for example assist in keeping the patient's pupils dilated. Conversely, the optically transparent sections may have a transmittance of 70-80%, 80-90%, 90-95%, 95-99%, and/or 99-99.5%, or 99.5%-100% or any combination of these ranges in the wavelength range at which the ophthalmic device operates such as at 450 nm, 515 nm, 532 nm, 630 nm, 840 nm, 930 nm, 1060 nm, 1310 nm, or any combination thereof or across the visible and/or near IR wavelength range or at least 10%, 20%, 30%, 40%, 50%, 60%, 70%, 80%, or 90% of that range.

Other methods and configurations for reducing retro-reflection back into the instrument can be used including any combination of the foregoing such as a combination of tilt and anti-reflective coatings.

Additionally, although various embodiments of the mask have been discussed above in connection with an optical coherence tomography device the mask may be used with other diagnostic instruments or devices and in particular other ophthalmic devices such as a scanning laser ophthalmoscope (SLO). One use for the AR coating on these goggles could be to increase transmission of emitted light into the eye. Optical instruments that sense back-reflected light (e.g. imaging instruments) often benefit from or require very sensitive instrumentation (e.g. avalanche photodiodes, interferometers, etc.) if the level of back-reflected light is low. Additionally, since the tissues in the eye are not very reflective, the low signal level of light back-reflected from the eye tissue to be imaged or evaluated by the ophthalmic imaging or diagnostic systems may be lost in noise if the ghost back-reflections are sufficiently high. As discussed above, reducing the optical interfaces that will be perpendicular to the incident beam at any point may advantageously reduce back-reflection that introduced noise. Various embodiments, therefore, employ tilting or curving the surface of the window. Additionally, signal can potentially be strengthened by increasing transmission of light (and consequently by reducing reflections) at every surface to increase or maximize power going both to and coming from the eye. This goal can be accomplished, for example, with AR coatings. Advantageously, in various embodiments, this increased transmission is accompanied by reduced reflections which improve the signal-to-noise ratio (SNR) and contrast in the images or data produced and reduce ghost artifacts that can appear as real objects, for example, in an OCT or other image. Other instruments may benefit for similar or different reasons.

While the invention has been discussed in terms of certain embodiments, it should be appreciated that the invention is not so limited. The embodiments are explained herein by way of example, and there are numerous modifications, variations and other embodiments that may be employed that would still be within the scope of the present invention.

For purposes of this disclosure, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

As used herein, the relative terms "temporal" and "nasal" shall be defined from the perspective of the person wearing the mask. Thus, temporal refers to the direction of the temples and nasal refers to the direction of the nose.

As used herein, the relative terms "superior" and "inferior" shall be defined from the perspective of the person wearing the mask. Thus, superior refers to the direction of the vertex of the head and inferior refers to the direction of the feet.

What is claimed is:

1. A disposable mask for performing an eye exam using an ophthalmic instrument, the mask comprising:
    a disposable distal portion having one or more substantially optically transparent sections, the substantially optically transparent sections being plano with negligible optical power;
    a disposable proximal portion coupled to the distal portion and having a rear surface that faces the subject's face when in use, wherein the rear surface of the proximal portion is configured to conform to contours of the subject's face and align the one or more substantially optically transparent sections of the distal portion with the subject's eyes; and
    means for removably attaching the disposable mask to the ophthalmic instrument without attachment to the subject such that at least one of the one or more substantially optically transparent sections has at least a portion thereof that is sloped with respect to an incident light beam from the ophthalmic instrument.

2. The mask of claim 1, wherein the portion of the at least one of the one or more substantially optically transparent sections is tilted with respect to the incident light beam at a slope angle having a magnitude ranging from about 1 degree to about 40 degrees.

3. The mask of claim 2, wherein the magnitude of the slope angle is greater than about 4 degrees.

4. The mask of claim 1, wherein at least one of the one or more substantially optically transparent sections has a planar optical surface for transmitting light to the subject's eye.

5. The mask of claim 1, wherein the portion of the at least one of the one or more substantially optically transparent sections of the distal portion is sloped upward or downward.

6. The mask of claim 1, wherein the portion of the at least one of the one or more substantially optically transparent sections of the distal portion is sloped temporally or nasally.

7. The mask of claim 1, wherein a first portion of a first of the one or more substantially optically transparent sections and a second portion of a second of the one or more substantially optically transparent sections are sloped temporally or nasally in opposite directions with respect to each other.

8. A system comprising: the mask of claim 1, and an ophthalmic instrument, wherein the ophthalmic instrument comprises an optical coherence tomography instrument.

9. A system comprising: the mask of claim 1, and an ophthalmic instrument, wherein said ophthalmic instrument comprises a scanning laser ophthalmoscope.

10. The mask of claim 1, wherein the proximal portion is inflatable or deflatable, and the rear surface is configured to conform to contours of the subject's face and align the one or more substantially optically transparent sections of the distal portion with the subject's eyes when the proximal portion is inflated or deflated; wherein the mask further comprises an inflation/deflation port providing access to inflate or deflate the proximal portion.

11. The mask of claim 1, wherein the proximal portion has two cavities extending from the rear surface toward the distal portion, the two cavities being aligned with the one or more substantially optically transparent sections and defining two openings on the rear surface to be aligned with the subject's eyes.

12. The mask of claim 11, wherein the rear surface is configured to seal against the subject's face so as to inhibit flow of fluid into and out of the two cavities through the rear surface.

13. The mask of claim 12, further comprising an ocular port providing access to at least one of the two cavities for gas or fluid flow into the at least one of the two cavities.

14. The mask of claim 1, wherein said means for removably attaching the disposable mask to the ophthalmic instrument is configured such that the sloped portion is sloped by more than the cone angle of the incident light beam established by the f-number or numerical aperture of the ophthalmic instrument.

15. The mask of claim 1, wherein at least one of the one or more substantially optically transparent sections is coated with an anti-reflective coating configured to reduce reflection of the incident light beam by the at least one of the one or more substantially optically transparent section.

16. The mask of claim 1, wherein the one or more substantially optically transparent sections comprises a left substantially optically transparent section and a right substantially optically transparent section disposed on left and right sides of a centerline for transmitting the incident light beam.

17. The mask of claim 1, wherein said distal portion and proximal portion are configured such that said mask is single use.

18. The mask of claim 1, wherein the one or more substantially optically transparent sections comprise plastic.

19. The mask of claim 1, wherein the distal portion has a thickness of less than 0.5 mm.

* * * * *

UNITED STATES PATENT AND TRADEMARK OFFICE
CERTIFICATE OF CORRECTION

PATENT NO. : 10,772,497 B2
APPLICATION NO. : 14/852379
DATED : September 15, 2020
INVENTOR(S) : Alexander C. Walsh et al.

It is certified that error appears in the above-identified patent and that said Letters Patent is hereby corrected as shown below:

In the Specification

In Column 16, Line 35, delete "exemplary" and insert --example by--.

In Column 28, Line 57, delete "63 land" and insert --631 and--.

In Column 34, Line 51, delete "A s" and insert --$\Delta$ is--.

In Column 38, Line 34, delete "35°," and insert --35°),--.

In Column 39, Line 65, delete "or) 60°" and insert --or 60°)--.

In Column 41, Line 66, delete "A" and insert --$\Delta$--.

In the Claims

In Column 46, Line 22, Claim 17, after "and" insert --said--.

Signed and Sealed this
Seventeenth Day of November, 2020

Andrei Iancu
*Director of the United States Patent and Trademark Office*